US011938127B2

United States Patent
Ratnam

(10) Patent No.: US 11,938,127 B2
(45) Date of Patent: Mar. 26, 2024

(54) METHODS AND COMPOSITIONS RELATING TO STEROID HORMONE RECEPTOR-DEPENDENT PROLIFERATIVE DISORDERS

(71) Applicant: Wayne State University, Detroit, MI (US)

(72) Inventor: Manohar Ratnam, Toledo, OH (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 17/954,686

(22) Filed: Sep. 28, 2022

(65) Prior Publication Data

US 2023/0102174 A1      Mar. 30, 2023

Related U.S. Application Data

(60) Provisional application No. 63/249,326, filed on Sep. 28, 2021.

(51) Int. Cl.
*A61K 31/4704* (2006.01)
*A61P 35/00* (2006.01)

(52) U.S. Cl.
CPC .......... *A61K 31/4704* (2013.01); *A61P 35/00* (2018.01)

(58) Field of Classification Search
CPC .............................. A61K 31/4704; A61P 35/00
See application file for complete search history.

(56) References Cited

U.S. PATENT DOCUMENTS

| 4,711,898 A | 12/1987 | Enomoto et al. |
| 2016/0354361 A1 | 12/2016 | Chu et al. |
| 2020/0330449 A1 | 10/2020 | Chein et al. |

FOREIGN PATENT DOCUMENTS

| WO | 2009/018350 A1 | 2/2009 |
| WO | 2009/026166 A2 | 2/2009 |

(Continued)

OTHER PUBLICATIONS

Sato et al. (1999), Direct conversion to 2-phenyl-4-quinolones via a 4-alkoxyflavylium salt from a naturally occurring flavanone. Journal of Heterocyclic Chemistry, 36: 1345-1347. (Year: 1999).*

*Primary Examiner* — Matthew P Coughlin
*Assistant Examiner* — Ashli Ariana Chicks
(74) *Attorney, Agent, or Firm* — Julie K. Staple; Dinsmore & Shohl LLP

(57) ABSTRACT

Pharmaceutical compositions are provided according to aspects of the present disclosure which include a compound having chemical structural formula I:

where $R_1$ is selected from the group consisting of: an alkyl group, a heteroalkyl group, an aryl group, a heteroaryl group, an alkenyl group, a heteroalkenyl group, an alkynyl group, a heteroalkynyl group, a cycloalkyl group, a heterocycloalkyl group, an alkylcycloalkyl group, a heteroalkyl cycloalkyl group, an aralkyl group, a heteroaralkyl group, an alkoxy group, a polar group, an ester and a charged group; a pharmaceutically acceptable hydrolysable, or enzymatically cleavable, prodrug form thereof; and/or a pharmaceutically acceptable salt thereof; where $R_4'$ is H or an alkoxy group; where both $R_5$ and $R_3'$ are OH, or where one or both (Continued)

OH groups is optionally modified as a pharmaceutically acceptable hydrolysable, or enzymatically cleavable, prodrug form thereof; and/or a deuterated form thereof; and/or a pharmaceutically acceptable salt thereof; and a pharmaceutically acceptable carrier.

20 Claims, 34 Drawing Sheets

(56) References Cited

FOREIGN PATENT DOCUMENTS

| | | | |
|---|---|---|---|
| WO | 2009/102498 A1 | 8/2009 | |
| WO | WO-2009129372 A1 * | 10/2009 | ............. A61K 31/35 |
| WO | 2017/136774 A1 | 8/2017 | |
| WO | 2019/028456 A1 | 2/2019 | |
| WO | 2019/089940 A1 | 5/2019 | |
| WO | 2019/178527 A1 | 9/2019 | |
| WO | 2019/246343 A1 | 12/2019 | |

* cited by examiner

FIG. 9A
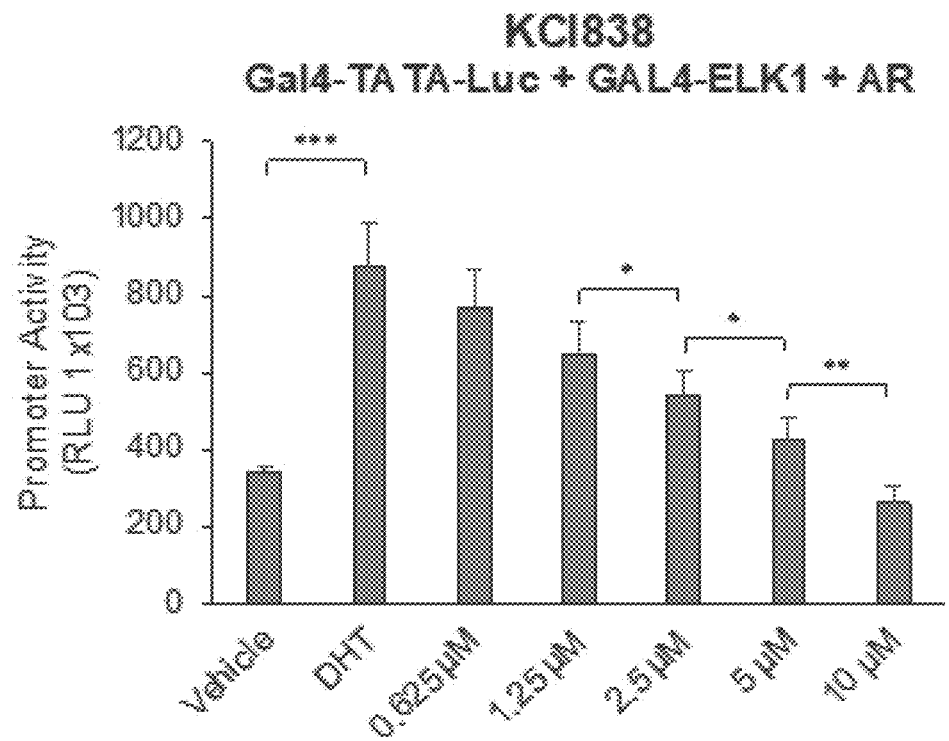
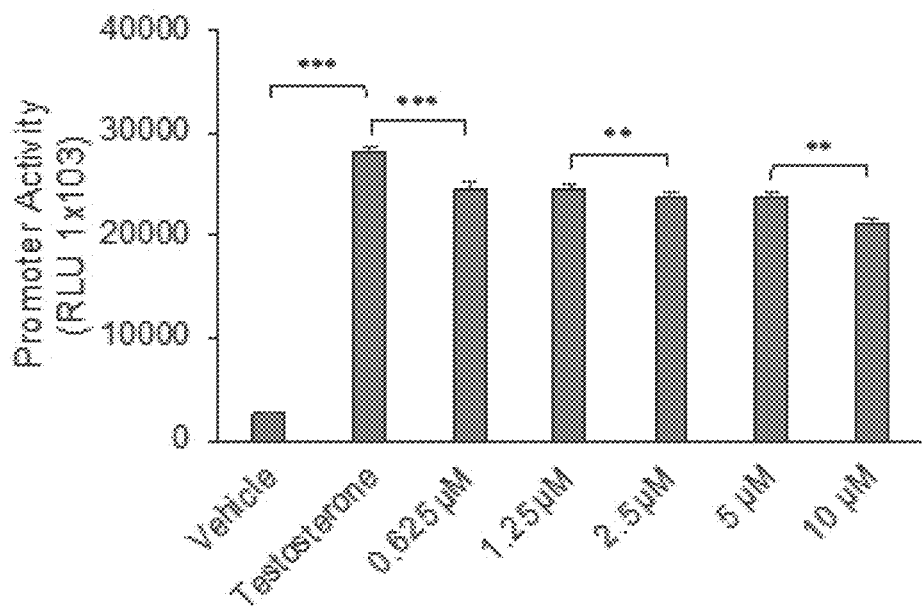
FIG. 9B

METHODS AND COMPOSITIONS RELATING TO STEROID HORMONE RECEPTOR-DEPENDENT PROLIFERATIVE DISORDERS

REFERENCE TO RELATED APPLICATION

This application claims priority to U.S. Provisional Patent Application Ser. No. 63/249,326, filed Sep. 28, 2021, the entire content of which is incorporated herein by reference.

FIELD OF THE INVENTION

According to general aspects described herein, compositions and methods are provided relating to steroid hormone receptor-dependent proliferative disorders including both steroid hormone receptor-dependent cancers and steroid hormone receptor-dependent non-cancer proliferative disorders. According to specific aspects, compositions and methods are provided relating to structural formulas I and II, a derivative of any thereof, and/or a pharmaceutically acceptable prodrug form of any thereof; and/or a deuterated form thereof; and/or a pharmaceutically acceptable salt of any thereof.

BACKGROUND OF THE INVENTION

There is a continuing need for methods and compositions relating to steroid hormone-receptor-dependent proliferative disorders, including pharmaceutical compositions including one or more compounds having activity against steroid hormone-receptor-dependent proliferative disorders and methods of treatment of a steroid hormone-receptor-dependent proliferative disorders in a subject using said pharmaceutical compositions.

SUMMARY OF THE INVENTION

Pharmaceutical compositions are provided according to aspects of the present disclosure which include a compound having chemical structural formula I:

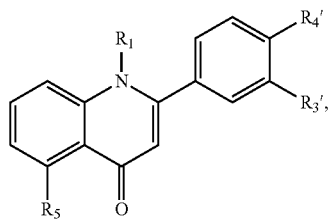

where $R_1$ is selected from the group consisting of: an alkyl group, a heteroalkyl group, an aryl group, a heteroaryl group, an alkenyl group, a heteroalkenyl group, an alkynyl group, a heteroalkynyl group, a cycloalkyl group, a heterocycloalkyl group, an alkylcycloalkyl group, a heteroalkyl cycloalkyl group, an aralkyl group, a heteroaralkyl group, an alkoxy group, a polar group, an ester and a charged group; a pharmaceutically acceptable hydrolysable, or enzymatically cleavable, prodrug form thereof; and/or a pharmaceutically acceptable salt thereof; where $R_4'$ is H or an alkoxy group; where both $R_5$ and $R_3'$ are OH, or where one or both of the OH groups is optionally modified as a pharmaceutically acceptable hydrolysable, or enzymatically cleavable, prodrug form thereof; and/or a deuterated form thereof; and/or a pharmaceutically acceptable salt thereof; and a pharmaceutically acceptable carrier. According to aspects of the present disclosure, the pharmaceutically acceptable hydrolysable, or enzymatically cleavable, prodrug form thereof is or includes an ester, a carbamate, or an ether. According to aspects of the present disclosure, $R_1$ is substituted with one or more halogen atoms. According to aspects of the present disclosure, $R_1$ is substituted with one or more of: fluorine, chlorine, bromine, and iodine. According to aspects of the present disclosure, one or both of $R_5$ and $R_3'$ of structure I is a pharmaceutically acceptable ester of an amino acid or dipeptide. According to aspects of the present disclosure, the amino acid is selected from the group consisting of: glycine, alanine, valine, leucine, isoleucine, tryptophan, phenylalanine and lysine. According to aspects of the present disclosure, the dipeptide is selected from the group consisting of: phenylalanine-glycine, valine-glycine, valine-alanine, serine-glutamic acid and proline-isoleucine.

Pharmaceutical compositions are provided according to aspects of the present disclosure which include a compound having structural formula II:

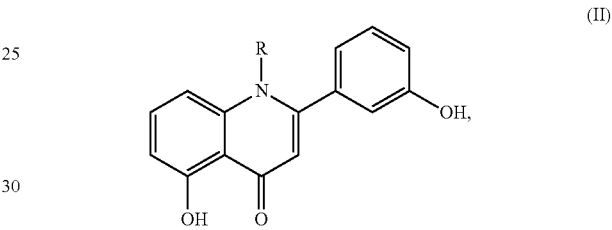

where R is methyl, propargyl, ethyl, propyl, isopropyl, isobutyl, tert-butyl, difluoroethyl, or trifluoroethyl; a derivative thereof, and/or a pharmaceutically acceptable hydrolysable, or enzymatically cleavable, prodrug form thereof, and/or a pharmaceutically acceptable salt thereof; and/or a deuterated form thereof; and a pharmaceutically acceptable carrier. According to aspects of the present disclosure, R is trifluoroethyl. According to aspects of the present disclosure, one or both OH groups is a pharmaceutically acceptable ester of an amino acid or dipeptide. According to aspects of the present disclosure, the amino acid is selected from the group consisting of: glycine, alanine, valine, leucine, isoleucine, tryptophan, phenylalanine and lysine. According to aspects of the present disclosure, the dipeptide is selected from the group consisting of: phenylalanine-glycine, valine-glycine, valine-alanine, serine-glutamic acid and proline-isoleucine.

Pharmaceutical compositions are provided according to aspects of the present disclosure which include a compound having structural formula:

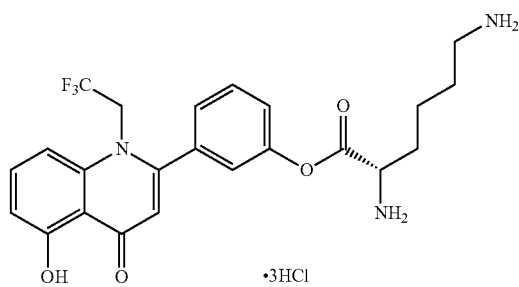 [SMILES: NCCCC[C@H](N)C(=O)Oc1cccc(-c2cc(=O)c3c(O)cccc3n2CC(F)(F)F)c1]

Pharmaceutical compositions are provided according to aspects of the present disclosure which include a compound having chemical structural formula I, or a compound having chemical structural formula II, and which further include an additional therapeutic agent.

Methods of treating a steroid hormone receptor-dependent proliferative disorder in a subject in need thereof are provided according to aspects of the present disclosure which include: administering a therapeutically effective dose of a pharmaceutical composition according to the present disclosure to the subject in need thereof. According to aspects of the present disclosure, the subject has an androgen receptor-dependent cancer. According to aspects of the present disclosure, the androgen receptor-dependent cancer is an androgen receptor-dependent prostate cancer or androgen receptor-dependent breast cancer. According to aspects of the present disclosure, the subject has an estrogen receptor-dependent cancer. According to aspects of the present disclosure, the estrogen receptor-dependent cancer is an estrogen receptor-dependent breast cancer. According to aspects of the present disclosure, the subject has a steroid hormone receptor-dependent bladder cancer. According to aspects of the present disclosure, the subject has a benign prostate hyperplasia Methods of treating a steroid hormone receptor-dependent proliferative disorder in a subject in need thereof are provided according to aspects of the present disclosure which include: administering a therapeutically effective dose of a pharmaceutical composition according to the present disclosure and further include an adjunct anti-cancer treatment.

Methods of treating a steroid hormone receptor-dependent proliferative disorder in a subject in need thereof are provided according to aspects of the present disclosure which include: administering a therapeutically effective dose of a pharmaceutical composition according to the present disclosure and further include administering an additional therapeutic agent.

Compounds are provided according to aspects of the present disclosure having chemical structural formula I:

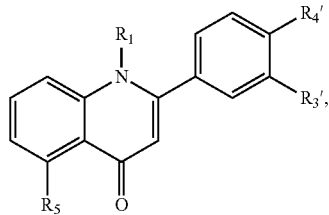

where $R_1$ is selected from the group consisting of: an alkyl group, a heteroalkyl group, an aryl group, a heteroaryl group, an alkenyl group, a heteroalkenyl group, an alkynyl group, a heteroalkynyl group, a cycloalkyl group, a heterocycloalkyl group, an alkylcycloalkyl group, a heteroalkyl cycloalkyl group, an aralkyl group, a heteroaralkyl group, an alkoxy group, a polar group, an ester and a charged group; a pharmaceutically acceptable hydrolysable, or enzymatically cleavable, prodrug form thereof; and/or a pharmaceutically acceptable salt thereof; where $R_4'$ is H or an alkoxy group; and where both $R_5$ and $R_3'$ are OH, or where one or both of the OH groups is optionally modified as a pharmaceutically acceptable hydrolysable, or enzymatically cleavable, prodrug form thereof; and/or a deuterated form thereof; and/or a pharmaceutically acceptable salt thereof. According to aspects of the present disclosure, the pharmaceutically acceptable hydrolysable, or enzymatically cleavable, prodrug form thereof comprises an ester, a carbamate, or an ether. According to aspects of the present disclosure, one or both of $R_5$ and $R_3'$ of structure I is a pharmaceutically acceptable ester of an amino acid or dipeptide. According to aspects of the present disclosure, the amino acid is selected from the group consisting of: glycine, alanine, valine, leucine, isoleucine, tryptophan, phenylalanine and lysine. According to aspects of the present disclosure, the dipeptide is selected from the group consisting of: phenylalanine-glycine, valine-glycine, valine-alanine, serine-glutamic acid and proline-isoleucine. According to aspects of the present disclosure, $R_1$ is substituted with one or more halogen atoms. According to aspects of the present disclosure, $R_1$ is substituted with one or more of: fluorine, chlorine, bromine, and iodine.

Compounds are provided according to aspects of the present disclosure having chemical structural formula II:

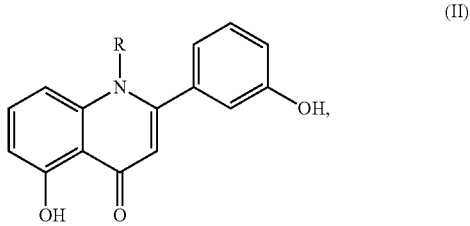

where R is methyl, propargyl, ethyl, propyl, isopropyl, isobutyl, tert-butyl, difluoroethyl, or trifluoroethyl; a derivative thereof, and/or a pharmaceutically acceptable hydrolysable, or enzymatically cleavable, prodrug form thereof; and/or a deuterated form thereof; and/or a pharmaceutically acceptable salt thereof. According to aspects of the present disclosure, one or both OH groups is a pharmaceutically acceptable ester of an amino acid or dipeptide. According to aspects of the present disclosure, the amino acid is selected from the group consisting of: glycine, alanine, valine, leucine, isoleucine, tryptophan, phenylalanine and lysine. According to aspects of the present disclosure, the dipeptide is selected from the group consisting of: phenylalanine-glycine, valine-glycine, valine-alanine, serine-glutamic acid and proline-isoleucine.

Commercial packages are provided according to aspects of the present disclosure which include a pharmaceutical composition and/or a compound of the present disclosure.

Methods of synthesizing a 4-quinolone compound are provided according to aspects of the present disclosure which include: contacting a flavone with a strong acid in a ratio of molar equivalents in the range of 1:2 to 1:100 in a closed system at a temperature in the range of 0° C. to 60° C. for a time period in the range of 2 hours to 10 days, producing a precipitate containing a corresponding flavylium salt; reacting the flavylium salt with an amine, wherein the flavylium salt and amine are present a ratio of molar equivalents in the range of 1:3 to 1:5, in an aprotic solvent for a second time period in the range of 2 hours to 2 days, producing a mixture comprising a 4-quinolone compound in the aprotic solvent; and purifying the 4-quinolone compound from the mixture. According to aspects of the present disclosure, purifying the 4-quinolone compound from the mixture includes at least one of: a) precipitation from an aprotic solvent such as hexane, acetone, ethyl acetate and mixtures in various proportions; b) recrystallization with a protic solvent such as ethanol or isopropanol; and c) using preparative plate chromatography method or column chromatography methods with material such as alumina (neutral or basic), producing purified 4-quinolone compound at purities of 90-98%, with yields in the range of 10-90%. According to aspects of the present disclosure, hydroxyl groups of the flavone are not protected. According to aspects of the present disclosure, the strong acid is not perchloric acid.

BRIEF DESCRIPTION OF THE DRAWINGS

FIG. 1A is a graph showing results of a time course of growth inhibition of 22Rv1 cells by enzalutamide;

FIG. 1B is a graph showing results of a time course of growth inhibition of 22Rv1 cells by KCI830;

FIG. 1C is a graph showing results of a time course of growth inhibition of 22Rv1 cells by KCI831;

FIG. 1D is a graph showing results of a time course of growth inhibition of 22Rv1 cells by KCI832;

FIG. 1E is a graph showing results of a time course of growth inhibition of 22Rv1 cells by KCI833;

FIG. 1F is a graph showing results of a time course of growth inhibition of 22Rv1 cells by KCI834;

FIG. 1G is a graph showing results of a time course of growth inhibition of 22Rv1 cells by KCI835;

FIG. 1H is a graph showing results of a time course of growth inhibition of 22Rv1 cells by KCI836;

FIG. 1I is a graph showing results of a time course of growth inhibition of 22Rv1 cells by KCI837;

FIG. 1J is a graph showing results of a time course of growth inhibition of 22Rv1 cells by KCI838;

FIG. 2A is a graph showing dose-dependent inhibition of 4-day growth of 22Rv1 cells by KCI830;

FIG. 2B is a graph showing dose-dependent inhibition of 4-day growth of 22Rv1 cells by KCI831;

FIG. 2C is a graph showing dose-dependent inhibition of 4-day growth of 22Rv1 cells by KCI832;

FIG. 2D is a graph showing dose-dependent inhibition of 4-day growth of 22Rv1 cells by KCI833;

FIG. 2E is a graph showing dose-dependent inhibition of 4-day growth of 22Rv1 cells by KCI834;

FIG. 2F is a graph showing dose-dependent inhibition of 4-day growth of 22Rv1 cells by KCI835;

FIG. 2G is a graph showing dose-dependent inhibition of 4-day growth of 22Rv1 cells by KCI836;

FIG. 2H is a graph showing dose-dependent inhibition of 4-day growth of 22Rv1 cells by KCI837;

FIG. 2I is a graph showing dose-dependent inhibition of 4-day growth of 22Rv1 cells by KCI838;

FIG. 6A is a graph showing the effects of compounds according to aspects of the present disclosure on production in primary human hepatocytes of CYP1A2, a monooxygenase;

FIG. 6B is a graph showing the effects of compounds according to aspects of the present disclosure on production in primary human hepatocytes of CYP2B6, a monooxygenase;

FIG. 6C is a graph showing the effects of compounds according to aspects of the present disclosure on production in primary human hepatocytes of SULT1A1, a sulfotransferase;

FIG. 6D is a graph showing the effects of compounds according to aspects of the present disclosure on production in primary human hepatocytes of SULT2A1, a sulfotransferase;

FIG. 6E is a graph showing the effects of compounds according to aspects of the present disclosure on production in primary human hepatocytes of UGT1A1, a UDP-glucuronyltransferase;

FIG. 6F is a graph showing the effects of compounds according to aspects of the present disclosure on production in primary human hepatocytes of UGT1A4, a UDP-glucuronyltransferase;

FIG. 7A is a graph showing inhibition of CYP1A2 by a-naphthoflavone;

FIG. 7B is a graph showing inhibition of CYP1A2 by KCI838;

FIG. 8A is a graph showing inhibition of UGT1A1 by atazanavir;

FIG. 8B is a graph showing inhibition of UGT1A1 by KCI838;

FIG. 9A is a graph showing that KCI838 inhibits ELK1-dependent promoter activation by AR;

FIG. 9B is a graph showing that KCI838 does not inhibit ARE-dependent promoter activation by AR;

FIG. 11A is a western blot showing a 2.1-fold higher expression of total AR in recombinant 22Rv1 cells transduced with lentiviral AR expression plasmid, compared with control cells transduced with the vector alone;

FIG. 11B shows the KCI838 dose response for inhibition of colony growth in the control 22Rv1 cells transduced with lentiviral vector alone FIG. 11C shows the KCI838 dose response for inhibition of colony growth in 22Rv1 cells transduced with lentiviral plasmid expressing AR;

FIG. 11D shows a plot to calculate the IC50 and IC75 values for inhibition of colony formation by KCI838 using GraphPad Prism 5 software in the control 22Rv1 cells transduced with lentiviral vector alone;

FIG. 11E shows a plot to calculate the IC50 and IC75 values for inhibition of colony formation by KCI838 using GraphPad Prism 5 software in 22Rv1 cells transduced with lentiviral plasmid expressing AR;

DETAILED DESCRIPTION OF THE INVENTION

Figure 1A:
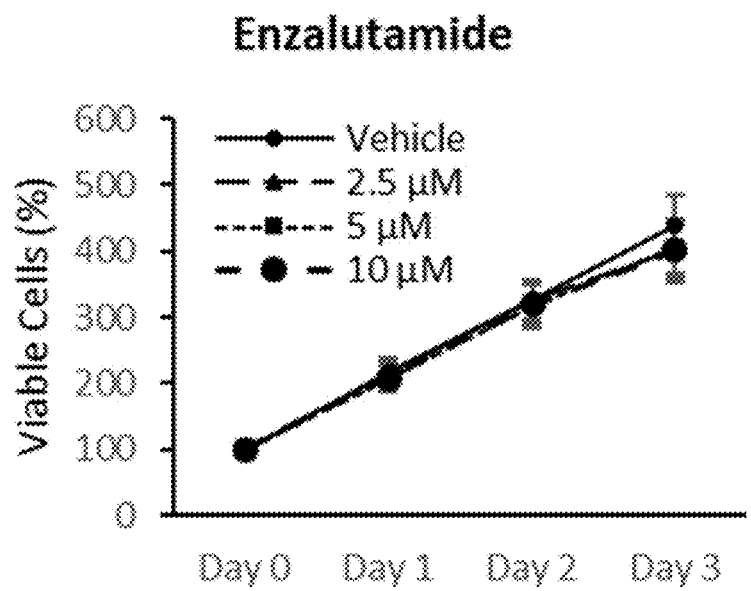
FIGS. 1A, 1B, 1C, 1D, 1E, 1F, 1G, 1H, 1I, and 1J, are graphs showing results of a time course of growth inhibition of 22Rv1 cells by individual compounds according to aspects of the present invention.
Figure 1B:
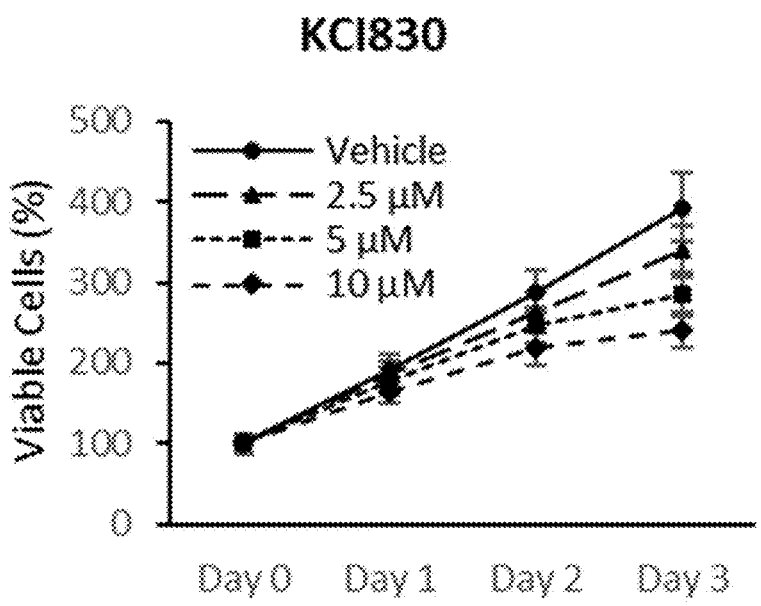
Figure 1C:
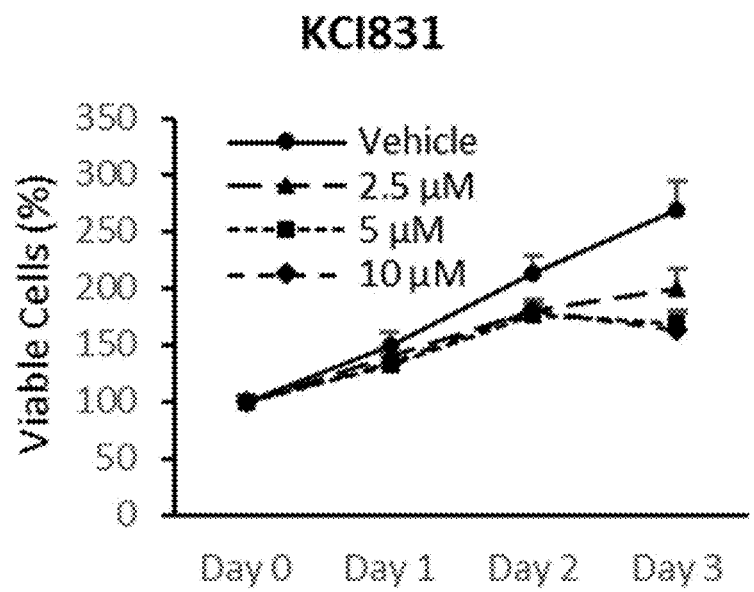
Figure 1D:
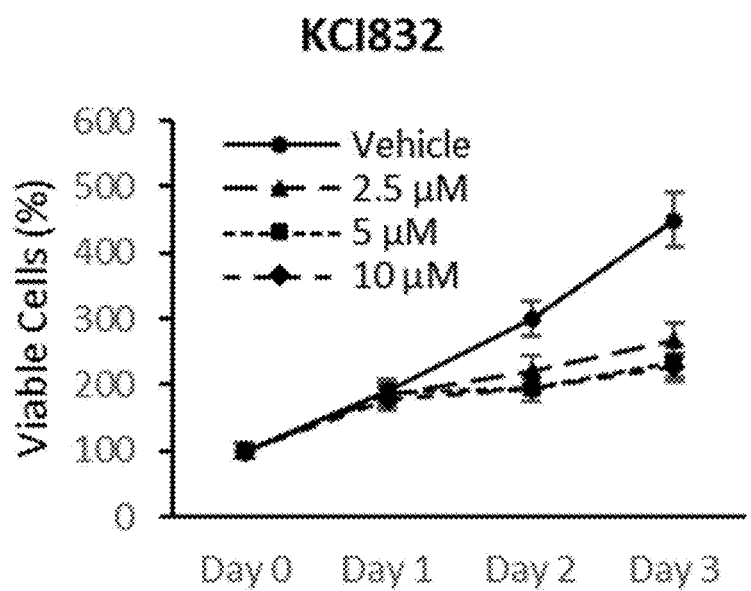
Figure 1E:
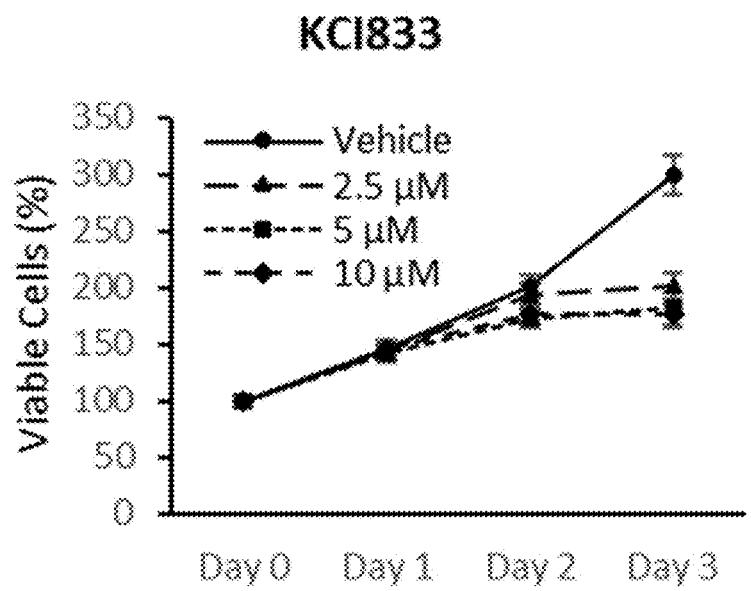
Figure 1F:
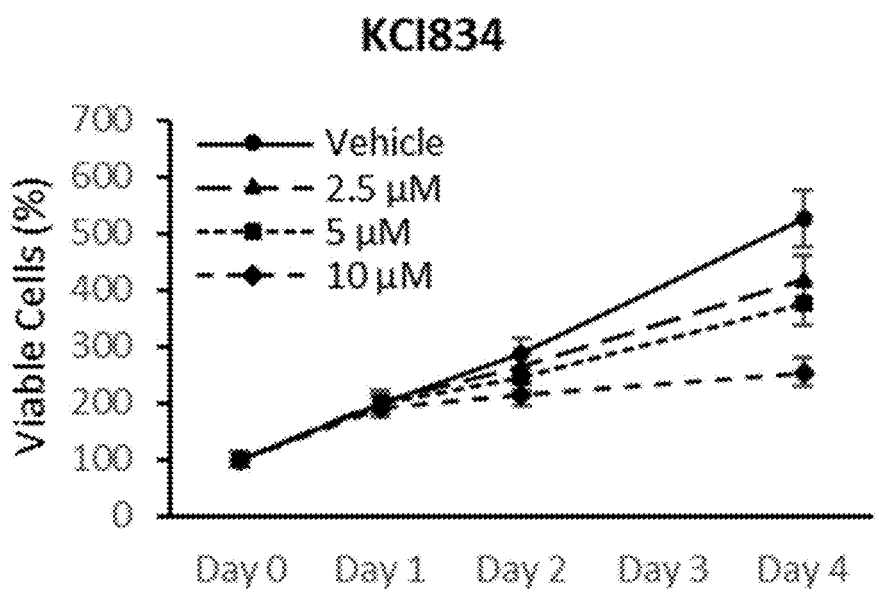
Figure 1G:
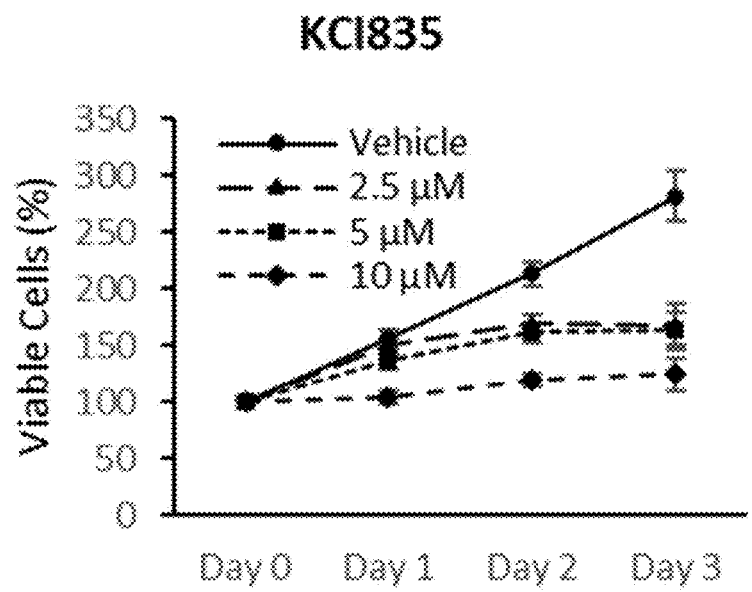
Figure 1H:
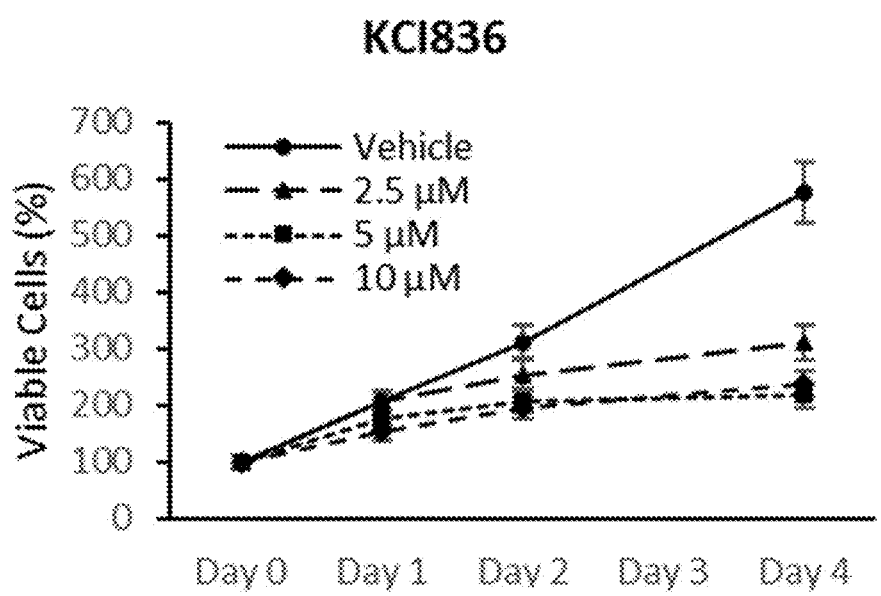
Figure 1I:
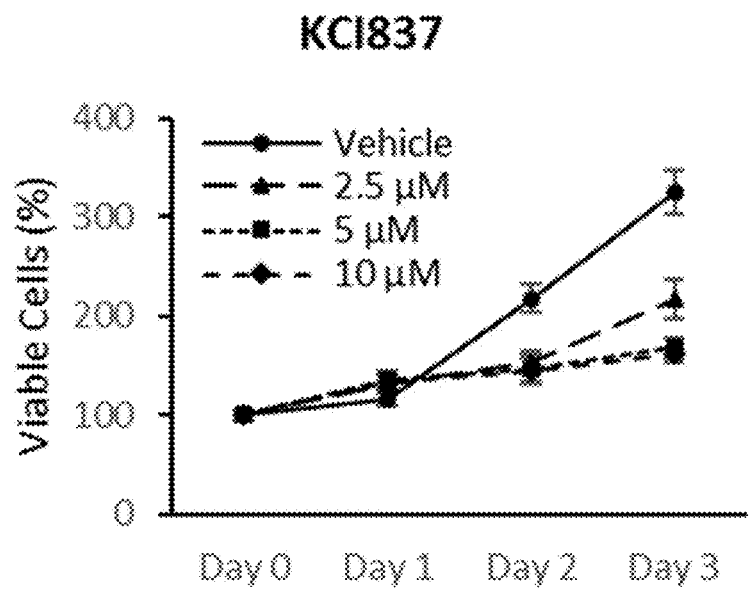
Figure 1J:
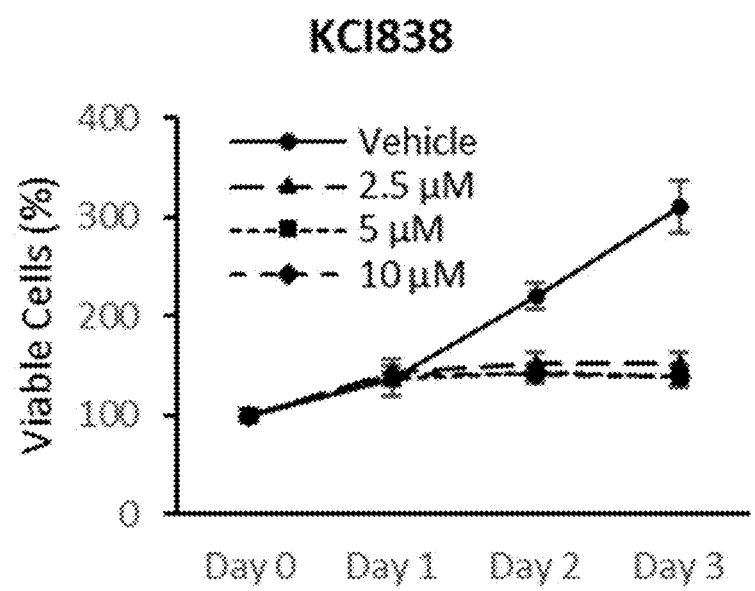
Figure 2A:
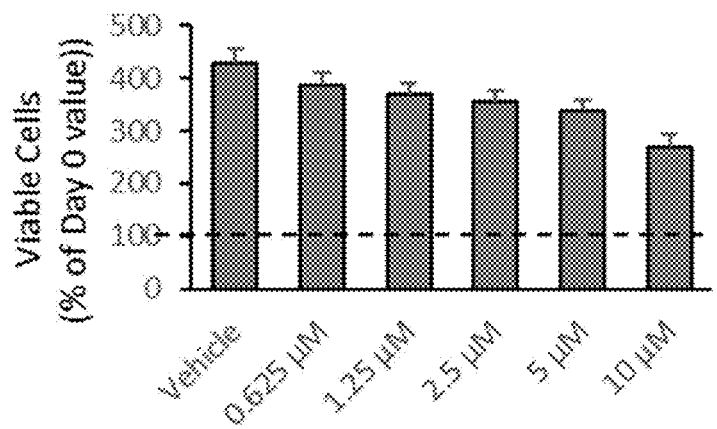
FIGS. 2A, 2B, 2C, 2D, 2E, 2F, 2G, 2H, and 2I, are graphs showing dose-dependent inhibition of 4-day growth of 22Rv1 cells by individual compounds according to aspects of the present invention.
Figure 2B:
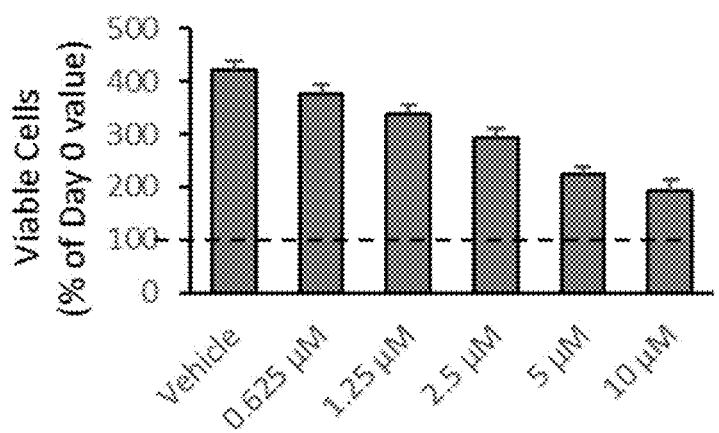
Figure 2C:
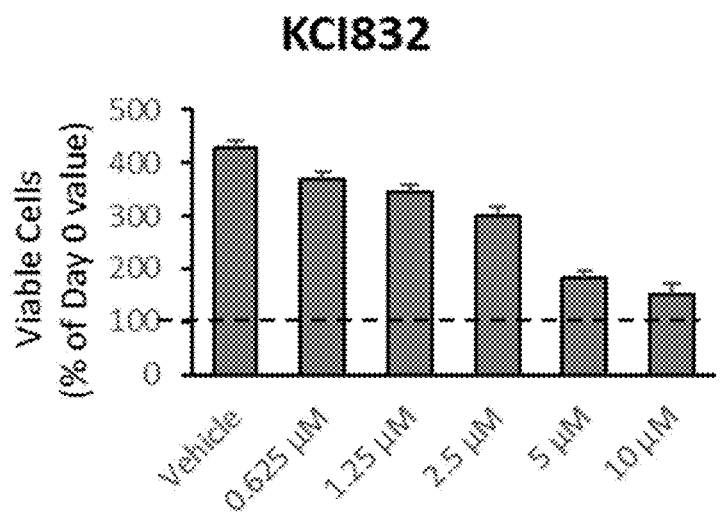
Figure 2D:
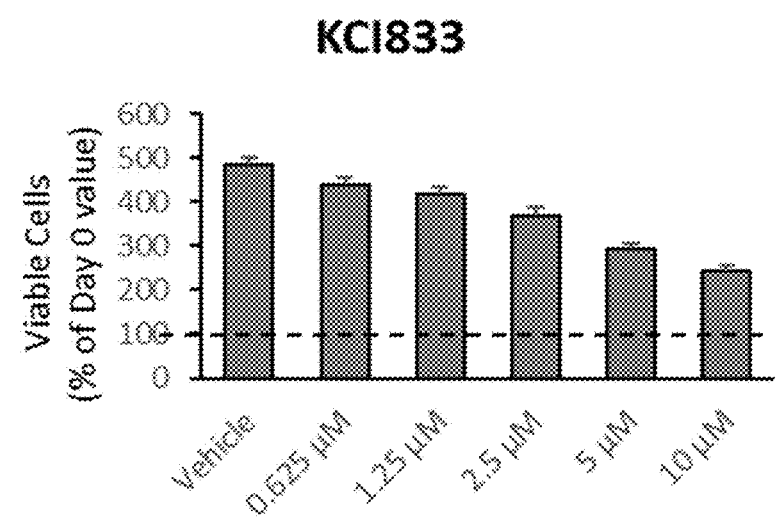
Figure 2E:
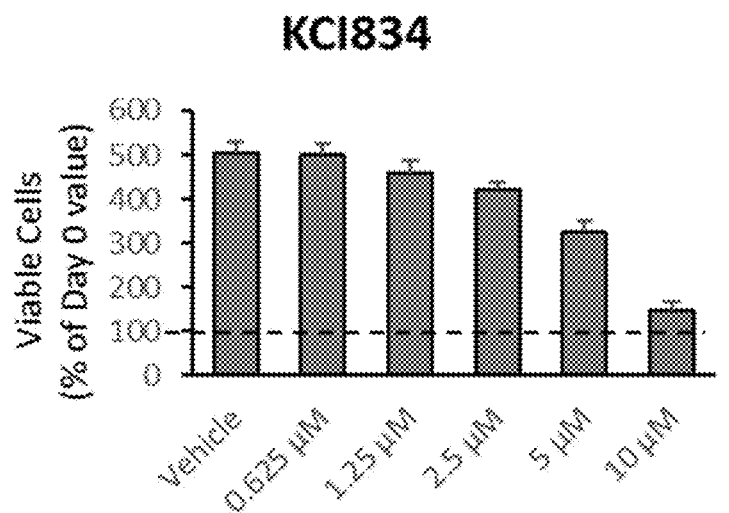
Figure 2F:
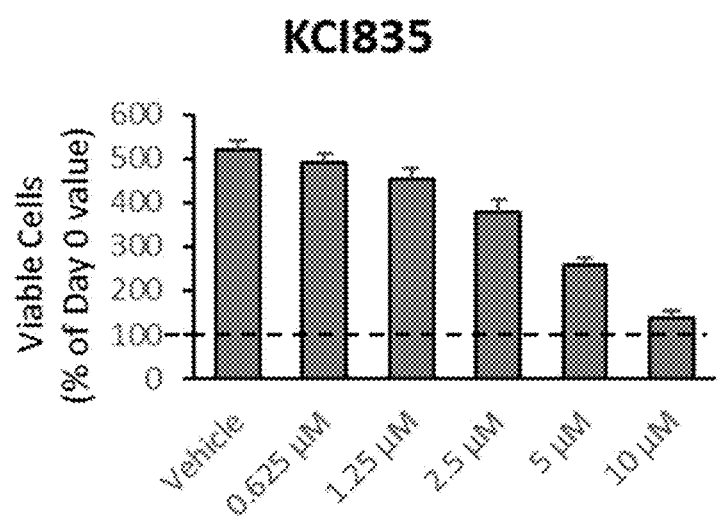
Figure 2G:
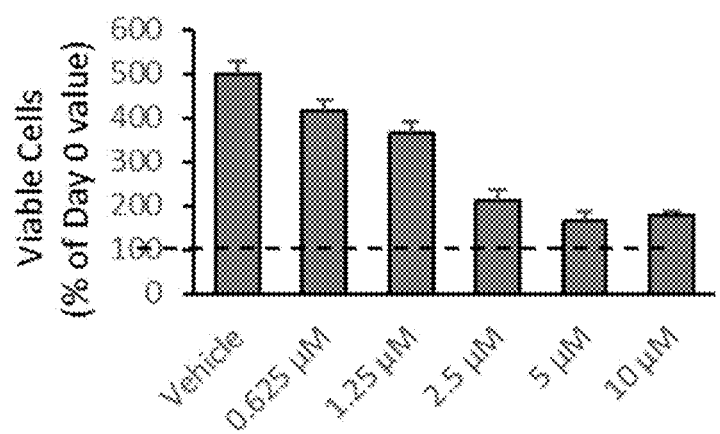
Figure 2H:
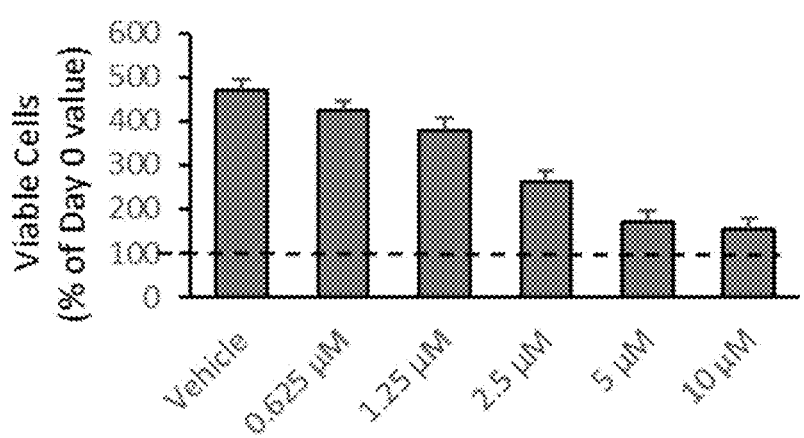
Figure 2I:
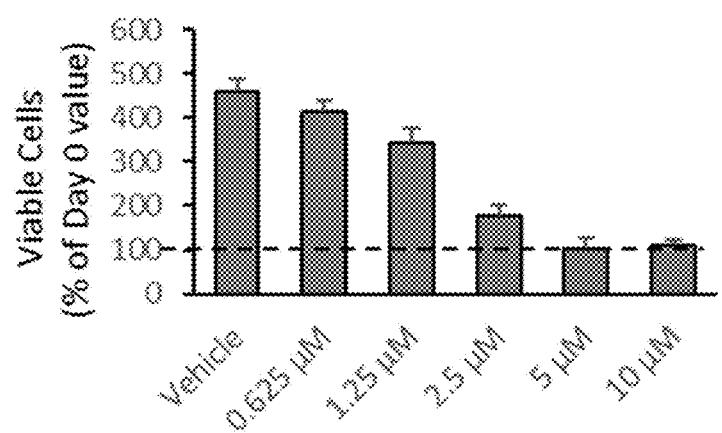

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Chu, E. and Devita, V. T., Eds., Physicians' Cancer Chemotherapy Drug Manual, Jones & Bartlett Publishers, 2021; J. M. Kirkwood et al., Eds., Current Cancer Therapeutics, 4th Ed., Current Medicine Group, 2001; Remington: The Science and Practice of Pharmacy, Elsevier, 23rd Ed., 2021; L. V. Allen, Jr. et al., Ansel's Pharmaceutical Dosage Forms and Drug Delivery Systems, 11th Ed., Wolters Kluwer, 2016; and L. Brunton et al., Goodman & Gilman's The Pharmacological Basis of Therapeutics, McGraw-Hill Education, 13th Ed., 2018.

The singular terms "a," "an," and "the" are not intended to be limiting and include plural referents unless explicitly stated otherwise or the context clearly indicates otherwise.

The terms "includes," "comprises," "including," "comprising," "has," "having," and grammatical variations thereof, when used in this specification, are not intended to be limiting, and specify the presence of stated features, elements, and/or components, but do not preclude the presence or addition of one or more other features, elements, components, and/or groups thereof.

The term "about" as used herein in reference to a number is used herein to include numbers which are greater, or less than, a stated or implied value by 1%, 5%, 10%, or 20%.

Particular combinations of features are recited in the claims and/or disclosed in the specification, and these combinations of features are not intended to limit the disclosure of various aspects. Combinations of such features not specifically recited in the claims and/or disclosed in the specification. Although each dependent claim listed below may directly depend on only one claim, the disclosure of various aspects includes each dependent claim in combination with every other claim in the claim set. As used herein, a phrase referring to "at least one of" a list of items refers to any combination of those items, including single members. As an example, "at least one of: a, b, or c" is intended to cover a alone; b alone; c alone, a and b, a, b, and c, b and c, a and c, as well as any combination with multiples of the same element, such as a and a; a, a, and a; a, a, and b; a, a, and c; a, b, and b; a, c, and c; and any other combination or ordering of a, b, and c).

Pharmaceutical Compositions and Methods of Treatment

Proliferative disorders treated using methods and compositions described herein are characterized by abnormal cell proliferation and are steroid hormone-receptor-dependent, including, but not limited to, benign hyperplasias, pre-neoplastic hyperproliferation, cancer in-situ, neoplasms and metastases.

The term "steroid hormone-receptor-dependent proliferative disorders" as used herein refers to both cancers and non-cancer disorders characterized by abnormal cell proliferation that is dependent on a steroid hormone receptor for growth and/or survival. The term "steroid hormone-receptor-dependent cancer" as used herein includes steroid hormone-sensitive cancer as well as cancers that depend on a steroid receptor for a steroid hormone acting independent of the steroid hormone or that depend on variant forms of the steroid hormone receptor that cannot bind steroid hormone. The term "steroid hormone-receptor-dependent cancer" includes, but is not limited to, estrogen-sensitive cancers or otherwise estrogen receptor-dependent cancers and androgen-sensitive cancers or otherwise androgen receptor-dependent cancers. Non-limiting examples of androgen-sensitive cancers and otherwise androgen-receptor-dependent cancers include testosterone-sensitive prostate cancer and testosterone-independent but androgen receptor-dependent prostate cancer including castration resistant prostate cancer (CRPC). Further examples include estrogen-sensitive breast cancer and estrogen-independent but estrogen receptor-dependent breast cancer. Further examples include steroid hormone-receptor-sensitive bladder cancer and steroid hormone-independent but steroid hormone-receptor-dependent bladder cancer. Further examples include testosterone-dependent breast cancer and testosterone-independent but androgen receptor-dependent breast cancer. The term "steroid hormone-independent receptor-dependent non-cancer proliferative disorder" includes, but is not limited to, benign prostatic hyperplasia, and benign proliferative breast disease.

Pharmaceutical compositions for use in treating a steroid hormone-receptor-dependent proliferative disorder are provided which include one or more anti-steroid hormone-receptor-dependent proliferative disorder compounds according to chemical structural formula I, a derivative thereof, and/or a pharmaceutically acceptable prodrug form thereof, and/or a deuterated form thereof, and/or a pharmaceutically acceptable salt thereof.

Chemical Structural Formula I:

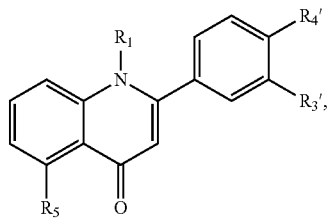

where $R_1$ is selected from: unhalogenated, fluorinated, chlorinated, brominated, or iodinated forms of the following: an alkyl group, a heteroalkyl group, an aryl group, a heteroaryl group, an alkenyl group, a heteroalkenyl group, an alkynyl group, a heteroalkynyl group, a cycloalkyl group, a heterocycloalkyl group, an alkylcycloalkyl group, a heteroalkyl cycloalkyl group, an aralkyl group, a heteroaralkyl group, an alkoxy group, a polar group, an ester and a charged group; and/or a pharmaceutically acceptable hydrolysable prodrug group such as an ester, carbamate or ether thereof and/or a deuterated form thereof and/or a pharmaceutically acceptable salt thereof where $R_4'$ is H or an alkoxy group; where both $R_5$ and $R_3'$ are OH, and where optionally one or both of the OH groups is modified to produce a pharmaceutically acceptable hydrolysable prodrug group such as an ester, carbamate, or ether; and/or a deuterated form thereof; and/or a pharmaceutically acceptable salt thereof.

Pharmaceutical compositions for use in treating a steroid hormone-receptor-dependent proliferative disorder are provided which include one or more anti-steroid hormone-receptor-dependent proliferative disorder compounds according to chemical structural formula II, a derivative thereof, and/or a pharmaceutically acceptable prodrug form thereof, and/or a deuterated form thereof; and/or a pharmaceutically acceptable salt thereof.

Chemical Structural Formula II:

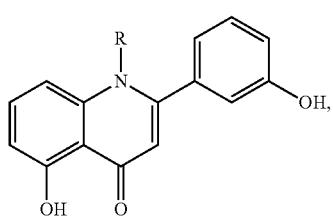

where R is methyl, propargyl, ethyl, propyl, isopropyl, isobutyl, tert-butyl, difluoroethyl, or trifluoroethyl.

According to particular aspects of the present disclosure, a compound of structural formula II is compound 1, also called KCI838 herein, which corresponds to structural formula II where R is trifluoroethyl:

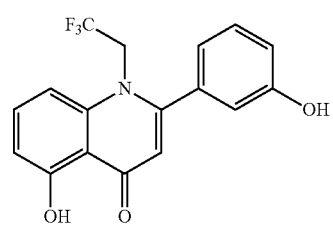 [SMILES: CCn1c(-c2cccc(O)c2)cc(=O)c2c(O)cccc21]

According to particular aspects of the present disclosure, a compound of structural formula II is called KCI837 herein, which corresponds to structural formula II where R is a difluoro-ethyl:

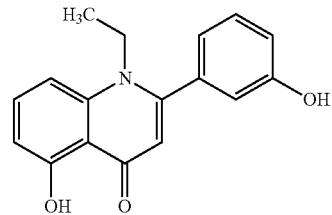

The term "alkyl group" as used herein refers to a straight or branched chain, or cyclic hydrocarbon, having the number of carbon atoms indicated. An included alkyl group can have, but is not limited to, one to 20 carbon atoms. Examples of alkyl groups include, but are not limited to, methyl, ethyl, n-propyl, isopropyl, n-butyl, t-butyl, isobutyl, sec-butyl, n-pentyl, n-hexyl, n-heptyl, n-octyl, and the like. According to aspects, an included alkyl group includes 1 to six carbon atoms, i.e. $C_1$-$C_6$. According to aspects, an included alkyl group includes 1 to three carbon atoms, i.e. $C_1$-$C_3$. According to aspects, an included alkyl group is a methyl group or ethyl group. One or more heteroatoms may be included in an alkyl group, replacing a carbon atom of the carbon backbone of the alkyl group, i.e. a heteroalkyl group.

According to aspects, an included alkyl group is a haloalkyl group. The term "haloalkyl" as used herein, refers to an alkyl group, as defined herein, which further includes 1 or more, e.g., 1, 2, 3, or 4, halogen atoms, e.g., fluorine, chlorine, bromine, or iodine, wherein the alkyl group is substituted with one or more halogen atoms. According to aspects, an included alkyl group is a fluorinated alkyl group, such as, but not limited to, trifluoroethyl (—$CH_2$—$CF_3$).

The term "alkoxy group" as used herein refers to an oxygen atom connected to an alkyl group. An alkoxy group can be attached to the remainder of the molecule through the oxygen atom. Examples of linear alkoxy groups include, but are not limited to, methoxy, ethoxy, propoxy, butoxy, pentyloxy, hexyloxy, and the like. Examples of branched alkoxy groups include, but are not limited to, isopropoxy, sec-butoxy, tert-butoxy, isopentyloxy, isohexyloxy, and the like. Examples of cyclic alkoxy include, but are not limited to, cyclopropyloxy, cyclobutyloxy, cyclopentyloxy, cyclohexyloxy, and the like. An included alkoxy group can have, but is not limited to, one to 20 carbon atoms. According to aspects, an included alkoxy group includes 1 to six carbon atoms, i.e. $C_1$-$C_6$. According to aspects, an included alkoxy group includes 1 to three carbon atoms, i.e. $C_1$-$C_4$. According to aspects, an included alkoxy group is a methoxy group, ethoxy group, methyltrimethoxy group, methyltriethoxy group, propoxy group, isopropoxy group, butoxy group, t-butoxy group, or any two or more thereof. One or more heteroatoms may be included in an alkoxy group, replacing a carbon atom of the carbon backbone of the alkoxy group, i.e. a heteroalkoxy group. According to aspects, an included alkoxy group is a haloalkoxy group. The terms "haloalkoxy" or "haloalkoxyl" as used herein, refer to an alkoxy group, as defined herein, which further includes 1 or more, e.g., 1, 2, 3, or 4, halogen atoms, e.g., fluorine, chlorine, bromine, or iodine, wherein the alkoxy group is substituted with one or more halogen atoms. According to aspects, an included alkoxy group is a fluorinated alkoxy group, such as, but not limited to, trifluoroethoxy (—O—$CH_2$—$CF_3$).

The term "aryl" as used herein refers to a polyunsaturated, aromatic, hydrocarbon substituent that includes a single ring or multiple rings, preferably from 1 to 3 rings, wherein the two or more of the multiple rings may be fused and wherein each ring contains 3-7 carbon atoms, preferably wherein each ring contains 5 or 6 carbon atoms. An aryl group can be attached to the remainder of the molecule through a heteroatom, such as N, O, or S, e.g. an aryloxy, such as a phenoxy group. One or more heteroatoms may be included in an aryl group, i.e. a heteroaryl group, wherein one or more of the 3-7 carbon atoms of each ring, independently, is a heteroatom or wherein one or more of the 5-6 carbon atoms of each ring, independently, is a heteroatom. Non-limiting examples of aryl groups are phenyl, biphenyl, naphthyl indacenyl, azulenyl, heptalenyl, fluorenyl, phenanthrenyl, and the like. One or more heteroatoms may be included in a aryl group, replacing a carbon atom of the carbon backbone of the aryl group, i.e. a heteroaryl group. A "heteroaryl" refers to an aryl group that contains one or more heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Aryl groups can be unsubstituted or substituted. Exemplary aryl groups include substituted or unsubstituted phenyl and substituted or unsubstituted naphthyl.

The term "alkenyl" refers to a straight or branched hydrocarbon chain having one or more double bonds. One or more heteroatoms may be included in an alkenyl group, i.e. a heteroalkenyl group.

The terms "cycloalkyl" and "heterocycloalkyl" refer to cyclic versions of "alkyl" and "heteroalkyl," respectively. A heteroatom of a heterocycloalky group can occupy the position at which the heterocycloalky group is attached to the remainder of structure I or II. Examples of cycloalkyl include, but are not limited to, cyclopropyl, cyclobutyl, cyclopentyl, cyclohexyl, 1-cyclohexenyl, 3-cyclohexenyl, cycloheptyl, cyclooctanyl, and the like. Examples of heterocycloalky include, but are not limited to, 1-piperidinyl, 2-piperidinyl, 3-piperidinyl, 1-piperazinyl, 2-piperazinyl, 3-morpholinyl, 4-morpholinyl, tetrahydrofuran-2-yl, tetrahydrofuran-3-yl, tetrahydrothien-2-yl, tetrahydrothien-3-yl, and the like.

The term "alkylcycloalkyl" refers to a monovalent saturated hydrocarbon ring system, typically monocyclic, bicyclic, or tricyclic, linked to an alkyl group. Specific examples of an alkylcycloalkyl group include a cyclopropylmethyl group, a cyclopropylethyl group, and a cyclohexylethyl group. One or more heteroatoms may be included in an alkylcycloalkyl group, replacing a carbon atom of the carbon backbone of the alkylcycloalkyl group, i.e. a heteroalkyl cycloalkyl or alkylcyclo heteroalkyl group.

The term "aralkyl" also known as "arylalkyl" refers to an alkyl group with an aryl substituent. One or more heteroatoms may be included in an aralkyl group, replacing a carbon atom of the carbon backbone of the aralkyl group, i.e. a heteroaralkyl.

The term "alkynyl," as used herein, refers to a straight or branched chain group, typically from 2 to 20 carbon atoms (e.g., from 2 to 4, from 2 to 6, or from 2 to 10 carbons) containing a carbon-carbon triple bond. Alkynyls are exemplified by ethynyl, 1-propynyl, and the like. One or more heteroatoms may be included in an alkynyl group, replacing a carbon atom of the carbon backbone of the alkynyl group, i.e. a heteroalkynyl.

Unless otherwise specified, each instance of an alkyl group, heteroalkyl group, alkoxy, heteroalkoxy, aryl group, heteroaryl group, alkenyl group, heteroalkenyl group, alkynyl group, heteroalkynyl group, cycloalkyl group, heterocycloalkyl group, alkylcycloalkyl group, heteroalkyl cycloalkyl group, aralkyl group, and heteroaralkyl group is independently optionally substituted with one or more substituents. The term "substituted" means that at least one hydrogen present on an alkyl group, heteroalkyl group, aryl group, and/or heteroaryl group is replaced with a permissible substituent. A permissible substituent is one which upon substitution results in a stable compound which does not spontaneously undergo an undesired transformation such as by rearrangement, cyclization, elimination, or other reaction. Such substituents include, for example, amino, hydroxy, cyano, carboxy, nitro, thio, alkoxy, and halogen, such as fluoro, iodo, bromo, chloro, trihaloalkyl, such as trihalomethyl, trihaloalkoxy, such as trihalomethoxy. Such substituents include, for example, alkyl, alkenyl, alkynyl, aryl, aralkyl, aryloxy, aralkoxy, carboxy, aroyl, alkoxycarbonyl, aryloxycarbonyl, aralkoxycarbonyl, acyloxy, acylamino, aroylamino, carbamoyl, alkylcarbamoyl, dialkylcarbamoyl, arylthio, alkylthio, and alkylene.

The term "polar group" can include uncharged and charged (both positively and negatively) polar groups. Typical examples of such polar groups include, but are not limited to, halogen, amine groups, hydroxyl groups, phosphate groups, phosphonate groups, sulfate groups, sulfhydryl groups, sulfonate groups, e.g. sulfonic acid, sulfonic salts and sulfonic esters, sulfonyl groups such as sulfonamides, carbonyl groups such as carboxylic acids and carboxylic amides, alkylamine groups, alkylammonium groups, and arylammonium groups. A charged group containing an amino group(s) or a carboxylic acid group(s) can be included.

Compositions are provided according to aspects of the present invention in prodrug form. The term "prodrug" refers to a pharmaceutical agent that is converted into a therapeutically active agent, typically from a less active form into a corresponding more active form, such as from a less bioavailable form to a more bioavailable form, under physiological conditions, such as in vivo. According to aspects of the present invention, a pharmaceutically acceptable prodrug form includes one or more moieties that are hydrolyzed under physiological conditions, such as in vivo, to produce a desired therapeutically active molecule. According to aspects of the present invention, a pharmaceutically acceptable prodrug is converted by an enzymatic activity under physiological conditions, such as in vivo. Such prodrugs may be pharmaceutically acceptable esters, carbamates, or ethers, of compositions provided according to aspects of the present invention. According to aspects, any one of $R_1$, $R_5$, $R_4'$, and $R_3'$ of structure I and one or more of the C3'-OH group, C5-OH group and R of structure II is modified to include a moiety such that the compound is a prodrug, i.e. in prodrug form. Pharmaceutically acceptable prodrugs of the compounds of this invention include, without limitation, ethers, carbamates, esters, amino acid esters, phosphate esters, and sulfonate esters. Examples of prodrug forms are described in Sloan, K. B., Prodrugs, M. Dekker, New York, 1992; and Testa, B. and Mayer, J. M., Hydrolysis in drug and prodrug metabolism: chemistry, biochemistry, and enzymology, Wiley-VCH, Zurich, 2003.

According to aspects, $R_3'$ of structure I is hydroxyl or a hydrolysable or enzymatically cleavable prodrug form and/or $R_5$ of structure I is hydroxyl or a hydrolysable or enzymatically cleavable prodrug form.

According to aspects, the 3'-hydroxyl of structure II is a hydrolysable or enzymatically cleavable prodrug form and/or the 5-hydroxyl of structure II is a hydrolysable or enzymatically cleavable prodrug form.

The term "pharmaceutically acceptable ester", as used herein, refers to esters that hydrolyze, or are enzymatically cleaved, in vivo and include those that break down readily in the human body to leave the parent compound or a salt thereof. The term "pharmaceutically acceptable ester" includes compounds or moieties which contain a carbon or a heteroatom bound to an oxygen atom which is bonded to the carbon of a carbonyl group. Suitable pharmaceutically acceptable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular pharmaceutically acceptable esters include formates, acetates, propionates, butyrates, acrylates and ethylsuccinates. Pharmaceutically acceptable esters include, in a non-limiting example L-amino acid or D-amino acid esters of amino acids such as glycine, alanine, valine, leucine, isoleucine, tryptophan, phenylalanine and lysine and esters of dipeptides such as phenylalanine-glycine, valine-glycine, valine-alanine, serine-glutamic acid and proline-isoleucine. Pharmaceutically acceptable amino acid esters and peptide esters as prodrug forms are described in Vale et al., Molecules, 2018 Sep. 11; 23(9):2318.

According to aspects, any one or more of $R_1$, $R_5$, $R_4'$, and $R_3'$ of structure I is a hydrolysable pharmaceutically acceptable ester or enzymatically cleavable pharmaceutically acceptable ester. According to aspects, any one or more of $R_1$, $R_5$, $R_4'$, and $R_3'$ of structure I is a pharmaceutically acceptable ester selected from: an amino acid ester, phosphate ester, sulfonate ester, an ester derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms, a propionate, a butyrate, an acrylate or an ethylsuccinate. According to aspects, any one or more of $R_1$, $R_5$, $R_4'$, and $R_3'$ of structure I is a pharmaceutically acceptable ester selected from L-amino acid or D-amino acid esters of amino acids such as glycine, alanine, valine, leucine, isoleucine, tryptophan, phenylalanine and lysine and esters of dipeptides such as phenylalanine-glycine, valine-glycine, valine-alanine, serine-glutamic acid and proline-isoleucine or a pharmaceutically acceptable salt of any thereof.

According to aspects, the 3'-hydroxyl of structure II is a hydrolysable or enzymatically cleavable prodrug form and/or the 5-hydroxyl of structure II is a hydrolysable or enzymatically cleavable prodrug form.

According to aspects, one or both of the 3' hydroxyl and the 5-hydroxyl of structure II is a hydrolysable pharmaceutically acceptable ester or enzymatically cleavable pharmaceutically acceptable ester. According to aspects, one or both of the 3' hydroxyl and the 5-hydroxyl of structure II is a pharmaceutically acceptable ester selected from: an amino acid ester, phosphate ester, sulfonate ester, an ester derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms, a formate, an acetate, a propionate, a butyrate, an acrylate or an ethylsuccinate. According to aspects, one or both of the 3' hydroxyl and the 5-hydroxyl of structure II is a pharmaceutically acceptable ester selected from L-amino acid or D-amino acid esters of amino acids such as glycine, alanine, valine, leucine, isoleucine, tryptophan, phenylalanine and lysine and esters of dipeptides such as phenylalanine-glycine, valine-glycine, valine-alanine, serine-glutamic acid and proline-isoleucineor a pharmaceutically acceptable salt of any thereof.

According to aspects of the present invention, the pharmaceutically acceptable ester is a lysyl ester (ester of the amino acid lysine) of a 3'-hydroxyl and/or of a 5-hydroxyl in structure I or II, or a pharmaceutically acceptable salt thereof.

According to aspects of the present invention, the pharmaceutically acceptable ester is a valinyl ester (ester of the amino acid valine) of a 3'-hydroxyl and/or of a 5-hydroxyl in structure I or II, or a pharmaceutically acceptable salt thereof.

According to aspects of the present invention, the pharmaceutically acceptable ester is a leucyl ester (ester of the amino acid leucine) of a 3'-hydroxyl and/or of a 5-hydroxyl in structure I or II, or a pharmaceutically acceptable salt thereof.

According to aspects of the present invention, the pharmaceutically acceptable ester is an isoleucyl ester (ester of the amino acid isoleucine) of a 3'-hydroxyl and/or of a 5-hydroxyl in structure I or II, or a pharmaceutically acceptable salt thereof.

Pharmaceutical compositions of compounds according to structural formula I and II, and derivatives of any thereof having anti-steroid hormone-receptor-dependent proliferative disorder activity, can be provided as pharmaceutically acceptable salts of any thereof, and/or pharmaceutically acceptable esters, carbamates, or ethers of any thereof and/or a deuterated form of any thereof.

As used herein, the term "derivative" is used to refer to a compound whose structure is sufficiently similar to those disclosed herein such that, based upon that similarity, it would be expected, by one skilled in the art, to exhibit the same or similar activities and utilities as the disclosed compounds.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J. Pharmaceutical Sciences, 66: 1-19 (1977), incorporated herein by reference. The salts can be prepared in situ during the final isolation and purification of the compounds of the invention, or separately by reacting a free base or free acid function with a suitable reagent, as described generally below.

For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Compounds of structural formula I and/or II, derivatives of any thereof, pharmaceutically acceptable salts of any thereof, and/or esters, carbamates, or ethers, of any thereof; and/or a deuterated form thereof; can be synthesized using chemical synthetic methodology described herein.

Compounds and pharmaceutical compositions of compounds according to structural formula I and II, and derivatives of any thereof having anti-steroid hormone-receptor-dependent proliferative disorder activity are characterized by ability to disrupt the association of AR with ELK1. ELK1 is a downstream effector of the MAPK signaling pathway and belongs to the ternary complex factor (TCF) sub-family of the ETS family of transcription factors. ELK1 characteristically binds to purine-rich GGA core sequences and is in a repressive or passive association with many cell proliferation genes. Phosphorylation by ERK transiently hyperstimulates ELK1 to activate its target genes including association of ELK1 with serum response factor (SRF) for activation of immediate early genes. Chromatin sites of AR binding are highly enriched for ELK1 binding DNA cis-elements. ELK1 is fully or partially required for a substantial proportion (~27 percent) of all gene activation by androgen in PCa cells and this gene subset is primarily enriched for growth functions. Anchoring of AR to a set of chromatin sites by ELK1 in PCa/CRPC cells enables constitutive activation of a crucial set of growth genes by AR. This is not associated with ELK1 phosphorylation or MAPK signaling and does not require the transactivation domain of ELK1. AR binds to ELK1 (Kd=$2 \times 10^{-8}$ M) by utilizing the two ERK docking sites in ELK1, largely through the amino-terminal A/B domain of AR which lacks the ligand binding site. The AR docking was essential for growth as demonstrated by the dominant-negative effect of a AR docking site mutant of ELK1 on growth of PCa cells that are insensitive to MEK inhibition. The major splice variants of AR also supported ELK1-dependent gene activation. Only AR-dependent tumor cells, (including enzalutamide-resistant CRPC expressing AR splice variants) are addicted to ELK1 for cell growth, colony formation and tumor formation. The interaction of AR with ELK1 is only required to activate a critical set of AR target genes that are exclusively enriched for genes supporting cell cycle progression and mitosis. ELK1 is not required for regulation of non-growth related genes by AR. ELK1 is also a strong and independent prognosticator of PCa recurrence. Therefore, disruption of the ELK1-AR complex using compounds and pharmaceutical compositions of compounds according to structural formula I and II, and derivatives of any thereof having anti-steroid hormone-receptor-dependent cancer activity selectively suppress growth of PCa/CRPC tumors including tumors dependent on AR splice variants, without significant effects on other functions of testosterone/AR and without affecting the normal functions of ELK1.

Methods of treatment of a subject having, or at risk of having steroid hormone receptor-dependent proliferative disorder are provided according to aspects of the present invention which include administering one or more compounds of structural formula I and/or II, and/or a derivative of any thereof, and/or one or more pharmaceutically acceptable esters, carbamates, or ethers thereof; and/or a deuterated form thereof; and/or pharmaceutically acceptable salts of any thereof.

Methods and compositions of the present invention can be used for prophylaxis as well as amelioration of signs and/or symptoms of steroid hormone receptor-dependent proliferative disorder. The terms "treating" and "treatment" used to refer to treatment of a steroid hormone receptor-dependent proliferative disorder in a subject include: preventing, inhibiting or ameliorating the steroid hormone receptor-dependent proliferative disorder in the subject, such as slowing progression of the steroid hormone receptor-dependent proliferative disorder and/or reducing or ameliorating a sign or symptom of the steroid hormone receptor-dependent proliferative disorder.

A therapeutically effective amount of one or more compounds of structural formula I or II, a derivative of any thereof, and/or one or more pharmaceutically acceptable esters, carbamates, or ethers of any thereof, and/or a deuterated form of any thereof, and/or salts of any thereof is an amount which has a beneficial effect in a subject being treated. In subjects having steroid hormone receptor-dependent proliferative disorder or at risk for having steroid hormone receptor-dependent proliferative disorder, such as a condition characterized by abnormal steroid hormone receptor-dependent cell proliferation including, but not limited to, benign prostate hyperplasia, pre-neoplastic hyperproliferation of steroid hormone receptor-dependent cells, steroid hormone receptor-dependent cancer, cancer in-situ, steroid hormone receptor-dependent neoplasms, steroid hormone receptor-dependent metastasis, a steroid hormone receptor-dependent tumor, a benign steroid hormone receptor-dependent growth or other steroid hormone receptor-dependent abnormal cell proliferation condition responsive to a composition of the present invention, a therapeutically effective amount of a composition of the present invention is effective to ameliorate or prevent one or more signs and/or symptoms of the steroid hormone receptor-dependent proliferative disorder.

A subject treated according to methods and using compositions of the present invention can be mammalian or non-mammalian. A mammalian subject can be any mammal including, but not limited to, a human; a non-human primate; a rodent such as a mouse, rat, or guinea pig; a domesticated pet such as a cat or dog; a horse, cow, pig, sheep, goat, or rabbit. A non-mammalian subject can be any non-mammal including, but not limited to, a bird such as a duck, goose, chicken, or turkey. Subjects can be either gender and can be any age. In aspects of methods including administration of an inventive pharmaceutical composition to a subject, the subject is human. The terms "subject" and "patient" are used interchangeably herein.

Combinations of: 1) one or more compounds of structural formula I or II, a derivative of any thereof; a pharmaceutically acceptable prodrug form of any thereof, and/or a deuterated form of any thereof, and/or a pharmaceutically acceptable salt of any thereof; and 2) one or more additional therapeutic agents are administered according to aspects of the present invention to treat steroid hormone receptor-dependent proliferative disorder.

The term "additional therapeutic agent" is used herein to refer to a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues which is a biologically, physiologically, or pharmacologically active substance (or substances) that acts locally or systemically in a subject.

Additional therapeutic agents included according to aspects of methods and compositions of the present disclosure include, but are not limited to, antibiotics, antivirals, antineoplastic agents, anti-cancer agents, analgesics, antidepressants, antipsychotics, antipyretics, antihistamines, anti-osteoporosis agents, anti-osteonecrosis agents, antiinflammatory agents, anxiolytics, chemotherapeutic agents, diuretics, growth factors, non-steroidal anti-inflammatory agents, and vasoactive agents.

Additional therapeutic agents for treatment of hormone receptor (AR)-dependent prostate cancer, included according to aspects of methods and compositions of the present invention include, but are not limited to, agents for chemical castration of a subject having hormone receptor (AR)-dependent prostate cancer. Agents for chemical castration of a subject having hormone receptor (AR)-dependent prostate cancer include an analog of the luteinizing hormone releasing hormone (LHRH) and/or an androgen antagonist, such as bicalutamide. Castration resistant hormone receptor (AR)-dependent prostate cancer (CRPC) is typically treated with an androgen synthesis inhibitor (abiraterone) and a high affinity androgen antagonist (enzalutamide). Abiraterone and enzalutamide are ineffective against prostate tumors that depend on splice variants of AR which do not bind or require androgen and hence cannot bind these drugs.

Compositions of the present invention are effective to treat benign prostate hyperplasia, either alone, or in combination with an additional therapeutic agent.

Compositions of the present invention are effective in the spectrum of prostate cancer, including early stage prostate cancer, CRPC and enzalutamide resistant and abiraterone resistant CRPC. Compositions of the present invention are effective against AR splice variants. Compositions of the present invention are or in various combinations with castration, chemical castration, abiraterone and AR antagonists such as bicalutamide and enzalutamide, with or without other anti-cancer drugs mentioned herein, and/or an additional therapeutic agent.

Steroid hormone receptor-dependent breast cancer is commonly treated using the partial ER antagonist, tamoxifen and less commonly the partial ER antagonist toremifene. In advanced stages a pure ER antagonist (an ER downregulator) such as fulvestrant may be used. In postmenopausal women, it is also commonly treated with an aromatase inhibitor (inhibitor of estrogen synthesis) such as anastrozole or letrozole. Pre-menopausal women may be treated with LHRH agents to suppress estrogen production in the ovary. Additional hormone therapies that are sometimes used, include megestrol (a drug with actions similar to progesterone) or fluoxymesterone, an anabolic steroid that reduces estrogen. An additional therapeutic agent may also be used.

Compositions of the present invention are effective in both early and advanced stage breast cancer, either individually or in various combinations with the hormonal therapies listed above, and/or an additional therapeutic agent.

Compositions of the present invention are effective in both early and advanced stage bladder cancer, either individually or in various combinations with the hormonal therapies listed above, and/or an additional therapeutic agent.

Compositions, commercial packages and methods of treatment of hormone receptor (AR)-dependent prostate cancer are provided which include a composition according to the present invention and one or more of: an agent for chemical castration such as an analog of the luteinizing hormone releasing hormone (LHRH) and/or an androgen antagonist, such as bicalutamide; an androgen synthesis inhibitor such as abiraterone; and a high affinity androgen antagonist such as enzalutamide. One or more additional therapeutic agents is optionally included.

Compositions, commercial packages and methods of treatment of steroid hormone receptor-dependent breast cancer are provided which include a composition according to the present invention and one or more of: the partial estrogen receptor (ER) antagonist, tamoxifen and/or the partial ER antagonist toremifene; an ER antagonist; an ER downregulator, such as fulvestrant; an aromatase inhibitor (inhibitor of estrogen synthesis) such as anastrozole or letrozole; an LHRH agent to suppress estrogen production in the ovary; megestrol (a drug with actions similar to progesterone); or fluoxymesterone, an anabolic steroid that reduces estrogen. One or more additional therapeutic agents is optionally included.

According to aspects of the present invention, combination therapies include: (1) administration of a pharmaceutical composition that includes a pharmaceutical combination composition including two or more of: a compound of structural formula I and/or II, a derivative of any thereof; a pharmaceutically acceptable prodrug form of any thereof, and/or a deuterated form of any thereof, and/or a pharmaceutically acceptable salt of any thereof, formulated together in a single pharmaceutical composition; and/or (2) co-administration of two or more of: a compound of structural formula I and/or II, a derivative of any thereof, a pharmaceutically acceptable prodrug form of any thereof, and/or a deuterated form of any thereof, and/or a pharmaceutically acceptable salt of any thereof, formulated together in a single pharmaceutical composition, wherein the two or more have not been formulated in the same composition. When using separate formulations the two or more compounds, derivatives, pharmaceutically acceptable esters, carbamates, or ethers of any thereof, and/or a deuterated form of any thereof, and/or pharmaceutically acceptable salts of any thereof, may be administered during a course of treatment at the same time, intermittent times, staggered times, prior to, subsequent to, or combinations thereof.

According to aspects of the present invention, combination therapies include: (1) administration of a pharmaceutical composition that includes a) and b) wherein a) is: at least one of: a compound of structural formula I and/or II, a derivative of any thereof, a pharmaceutically acceptable prodrug form of any thereof, and/or a deuterated form of any thereof, and/or a pharmaceutically acceptable salt of any thereof; and wherein b) is: a therapeutic agent, wherein a) and b) are formulated together in a single pharmaceutical composition; and/or (2) co-administration of a) and b). When using separate formulations a) and b) may be administered during a course of treatment at the same time, intermittent times, staggered times, prior to, subsequent to, or combinations thereof.

Combination treatments can allow for reduced effective dosage and increased therapeutic index compared to treatment with a single active agent.

The term "course of treatment" refers to a period of time over which a subject is treated for a specified condition. The course of treatment may be a single administration extending minutes, hours, days or months (such as continuous intravenous administration for example) or may include multiple administrations of a pharmaceutical composition with intervening periods between each administration, wherein the intervening period may extend minutes, hours, days or months. In general, a course of treatment extends minutes, hours, days or months, even years, until the desired beneficial effect is achieved, e.g. amelioration of signs or symptoms of steroid hormone receptor-dependent proliferative disorder.

An additional therapeutic agent is an anti-cancer agent according to aspects of the present invention.

Anti-cancer agents are described, for example, in L. Brunton et al., Goodman & Gilman's The Pharmacological Basis of Therapeutics, McGraw-Hill Education, 13th Ed., 2018.

Anti-cancer agents illustratively include acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bevacizumab, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflomithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, and zorubicin.

Anti-cancer agents illustratively include immune checkpoint inhibitors.

The term "immune checkpoint inhibitor" refers to a substance having activity to specifically inhibit immune checkpoint activity, including inhibition of T cells expressing PD-1 to suppress immune reaction to cancer cells. An immune checkpoint inhibitor can be a PD-1 inhibitor, a PD-1 ligand (PD-L1) inhibitor, or a CTLA4 inhibitor.

PD-L1 inhibitors are anti-PD-L1 antibodies such as, but not limited to, atezolizumab, avelumab, and durvalumab; and an antigen-binding fragment of any one of the foregoing. siRNA or a CRISPR/Cas knockdown construct directed to PD-L1 can be used to inhibit PD-L1.

CTLA4 inhibitors are anti-CTLA4 antibodies such as, but not limited to ipilimumab and an antigen-binding fragment thereof. siRNA or a CRISPR/Cas knockdown construct directed to CTLA4 can be used to inhibit CTLA4.

PD-1 inhibitors are anti-PD-1 antibodies such as, but not limited to, nivolumab, and pembrolizumab; and an antigen-binding fragment of any one of the foregoing. siRNA or a CRISPR/Cas knockdown construct directed to PDL1 can be used to inhibit PD-1.

According to aspects of the present invention, one or more correlative biomarkers of therapeutic activity of: one or more of: a compound of structural formula I and/or II, a derivative of any thereof, a pharmaceutically acceptable prodrug form of any thereof, and/or a deuterated form of any thereof, and/or a pharmaceutically acceptable salt of any thereof, formulated in a single pharmaceutical composition; and/or (2) co-administration of two or more of: a compound of structural formula I and/or II, a derivative of any thereof, a pharmaceutically acceptable prodrug form of any thereof, and/or a deuterated form of any thereof, and/or a pharmaceutically acceptable salt of any thereof, formulated together in a single pharmaceutical composition, administered to treat cancer proliferative disorder in a subject are assayed to assess treatment of the proliferative disorder in the subject. Thus, for example, the inhibition of tumor growth is a correlative biomarker of therapeutic activity of treatment administered as a combination treatment of the present invention to treat cancer in a subject in need thereof. Inhibition of tumor growth is measured according to standard methodologies, for example as described herein.

Optionally, a method of treating cancer in a subject in need thereof further includes an adjunct anti-cancer treatment. An adjunct anti-cancer treatment can be a radiation treatment of a subject or an affected area of a subject's body.

The dosage of any one or more of: a compound of structural formula I and/or II, a derivative of any thereof, a pharmaceutically acceptable prodrug form of any thereof, and/or a pharmaceutically acceptable salt of any thereof, formulated together in a single pharmaceutical composition, as well as any optional additional therapeutic agent will vary based on factors such as, but not limited to, the route of administration; the age, health, sex, and weight of the subject to whom the composition is to be administered; the nature and extent of the subject's symptoms, if any, and the effect desired. Dosage may be adjusted depending on whether treatment is to be acute or continuing. One of skill in the art can determine a pharmaceutically effective amount in view of these and other considerations typical in medical practice.

In general it is contemplated that a daily dosage of any one or more of: a compound of structural formula I and/or II, a derivative of any thereof, a pharmaceutically acceptable prodrug form of any thereof, and/or a deuterated form of any thereof, and/or a pharmaceutically acceptable salt of any thereof, and any optional additional therapeutic agent, is in the range of about 0.001 to 250 milligrams per kilogram of a subject's body weight. A daily dose may be administered as two or more divided doses to obtain the desired effect. A pharmaceutical composition including any one or more of: a compound of structural formula I and/or II, a derivative of any thereof, a pharmaceutically acceptable prodrug form of any thereof, and/or a deuterated form of any thereof, and/or a pharmaceutically acceptable salt of any thereof, and any optional additional therapeutic agent, may also be formulated for sustained release to obtain desired results.

In particular aspects of inventive methods, the amount of the adjunct anti-cancer treatment and/or anti-cancer agent administered is less than an amount of the adjunct anti-cancer treatment and/or anti-cancer agent necessary to achieve a therapeutic effect if administered without one or more of: a compound of structural formula I and/or II, a derivative of any thereof, a pharmaceutically acceptable prodrug form of any thereof, and/or a deuterated form of any thereof, and/or a pharmaceutically acceptable salt of any thereof. Thus, in particular aspects of the present invention, the amount of an anti-cancer treatment and/or agent administered is at least 5%, at least 10%, at least 15%, at least 20%, at least 25%, at least 30%, at least 35%, at least 40%, at least 50%, at least 55%, at least 60%, at least 65%, at least 70%, at least 75%, at least 80%, at least 85%, or at least 90%, less than an amount of the adjunct anti-cancer treatment and/or agent necessary to achieve a therapeutic effect when administered without a combination treatment of the present invention additionally including administration of one or more of: a compound of structural formula I and/or II, a derivative of any thereof, a pharmaceutically acceptable prodrug form of any thereof, and/or a deuterated form of any thereof, and/or a pharmaceutically acceptable salt of any thereof.

Methods of the present invention include administration of a pharmaceutical composition of the present invention by a route of administration including, but not limited to, oral, rectal, nasal, pulmonary, epidural, ocular, otic, intraarterial, intracardiac, intracerebroventricular, intradermal, intravenous, intramuscular, intraperitoneal, intraosseous, intrathecal, intravesical, subcutaneous, topical, transdermal, and transmucosal, such as by sublingual, buccal, vaginal, and inhalational, routes of administration.

Combination Pharmaceutical Compositions

A combination pharmaceutical composition including two or more of a compound of structural formula I and/or II, a derivative of any thereof, a pharmaceutically acceptable prodrug form of any thereof, and/or a deuterated form of any thereof, and/or a pharmaceutically acceptable salt of any thereof, according to the invention generally includes about 0.1-99% w/v of each and a pharmaceutically acceptable carrier.

A pharmaceutical composition of the present invention may be in any dosage form suitable for administration to a subject, illustratively including solid, semi-solid and liquid dosage forms such as tablets, capsules, powders, granules, suppositories, pills, solutions, suspensions, ointments, lotions, creams, gels, pastes, sprays and aerosols. Liposomes and emulsions are well-known types of pharmaceutical formulations that can be used to deliver a pharmaceutical agent, particularly a hydrophobic pharmaceutical agent. Pharmaceutical compositions of the present invention generally include a pharmaceutically acceptable carrier such as an excipient, diluent and/or vehicle. Delayed release formulations of compositions and delayed release systems, such as semipermeable matrices of solid hydrophobic polymers can be used.

A pharmaceutical formulation of a composition of the present invention can include a pharmaceutically acceptable carrier. The term "pharmaceutically acceptable carrier" refers to a carrier which is suitable for use in a subject without undue toxicity or irritation to the subject and which is compatible with other ingredients included in a pharmaceutical composition.

Pharmaceutically acceptable carriers, methods for making pharmaceutical compositions and various dosage forms, as well as modes of administration are well-known in the art, for example as detailed in Pharmaceutical Dosage Forms: Tablets, eds. H. A. Lieberman et al., New York: Marcel Dekker, Inc., 1989; and in L. V. Allen, Jr. et al., Ansel's Pharmaceutical Dosage Forms and Drug Delivery Systems, 8th Ed., Philadelphia, Pa.: Lippincott, Williams & Wilkins, 2004; A. R. Gennaro, Remington: The Science and Practice of Pharmacy, Lippincott Williams & Wilkins, 21st ed., 2005, particularly chapter 89; and J. G. Hardman et al., Goodman & Gilman's The Pharmacological Basis of Therapeutics, McGraw-Hill Professional, 10th ed., 2001.

A solid dosage form for administration or for suspension in a liquid prior to administration illustratively includes capsules, tablets, powders, and granules. In such solid dosage forms, one or more active agents, is admixed with at least one carrier illustratively including a buffer such as, for example, sodium citrate or an alkali metal phosphate illustratively including sodium phosphates, potassium phosphates and calcium phosphates; a filler such as, for example, starch, lactose, sucrose, glucose, mannitol, and silicic acid; a binder such as, for example, carboxymethylcellulose, alignates, gelatin, polyvinylpyrrolidone, sucrose, and acacia; a humectant such as, for example, glycerol; a disintegrating agent such as, for example, agar-agar, calcium carbonate, plant starches such as potato or tapioca starch, alginic acid, certain complex silicates, and sodium carbonate; a solution retarder such as, for example, paraffin; an absorption accelerator such as, for example, a quaternary ammonium compound; a wetting agent such as, for example, cetyl alcohol, glycerol monostearate, and a glycol; an adsorbent such as, for example, kaolin and bentonite; a lubricant such as, for example, talc, calcium stearate, magnesium stearate, a solid polyethylene glycol or sodium lauryl sulfate; a preservative such as an antibacterial agent and an antifungal agent, including for example, sorbic acid, gentamycin and phenol; and a stabilizer such as, for example, sucrose, EDTA, EGTA, and an antioxidant.

Solid dosage forms optionally include a coating such as an enteric coating. The enteric coating is typically a polymeric material. Preferred enteric coating materials have the characteristics of being bioerodible, gradually hydrolyzable and/or gradually water-soluble polymers. The amount of coating material applied to a solid dosage generally dictates the time interval between ingestion and drug release. A coating is applied having a thickness such that the entire coating does not dissolve in the gastrointestinal fluids at pH below 3 associated with stomach acids, yet dissolves above pH 3 in the small intestine environment. It is expected that any anionic polymer exhibiting a pH-dependent solubility profile is readily used as an enteric coating in the practice of the present invention to achieve delivery of the active agent to the lower gastrointestinal tract. The selection of the specific enteric coating material depends on properties such as resistance to disintegration in the stomach; impermeability to gastric fluids and active agent diffusion while in the stomach; ability to dissipate at the target intestine site; physical and chemical stability during storage; non-toxicity; and ease of application.

Suitable enteric coating materials illustratively include cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonium methylacrylate, ethyl acrylate, methyl methacrylate and/or ethyl; vinyl polymers and copolymers such as polyvinyl pyrrolidone, polyvinyl acetate, polyvinylacetate phthalate, vinylacetate crotonic acid copolymer, and ethylene-vinyl acetate copolymers; shellac; and combinations thereof. A particular enteric coating material includes acrylic acid polymers and copolymers described for example U.S. Pat. No. 6,136,345.

The enteric coating optionally contains a plasticizer to prevent the formation of pores and cracks that allow the penetration of the gastric fluids into the solid dosage form. Suitable plasticizers illustratively include, triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, a coating composed of an anionic carboxylic acrylic polymer typically contains approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g. hydroxypropylcellulose, acids or bases) to solubilize or disperse the coating material, and to improve coating performance and the coated product.

Liquid dosage forms for oral administration include one or more active agents and a pharmaceutically acceptable carrier formulated as an emulsion, solution, suspension, syrup, or elixir. A liquid dosage form of a composition of the present invention may include a colorant, a stabilizer, a wetting agent, an emulsifying agent, a suspending agent, a sweetener, a flavoring, or a perfuming agent.

For example, a composition for parenteral administration may be formulated as an injectable liquid. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of a desirable particle size in the case of dispersions, and/or by the use of a surfactant, such as sodium lauryl sulfate. A stabilizer is optionally included such as, for example, sucrose, EDTA, EGTA, and an antioxidant.

For topical administration, a composition can be formulated for administration to the skin such as for local effect, and/or as a "patch" formulation for transdermal delivery. Pharmaceutical formulations suitable for topical administration include, for example, ointments, lotions, creams, gels, pastes, sprays and powders. Ointments, lotions, creams, gels and pastes can include, in addition to one or more active agents, a base such as an absorption base, water-removable base, water-soluble base or oleaginous base and excipients such as a thickening agent, a gelling agent, a colorant, a stabilizer, an emulsifying agent, a suspending agent, a sweetener, a flavoring, or a perfuming agent.

Transdermal formulations can include percutaneous absorption enhancers such as acetone, azone, dimethyl acetamide, dimethyl formamide, dimethyl sulfoxide, ethanol, oleic acid, polyethylene glycol, propylene glycol and sodium lauryl sulfate. Ionotophoresis and/or sonophoresis can be used to enhance transdermal delivery.

Powders and sprays for topical administration of one or more active agents can include excipients such as talc, lactose and one or more silicic acids. Sprays can include a pharmaceutical propellant such as a fluorinated hydrocarbon propellant, carbon dioxide, or a suitable gas. Alternatively, a spray can be delivered from a pump-style spray device which does not require a propellant. A spray device delivers a metered dose of a composition contained therein, for example, using a valve for regulation of a delivered amount.

Ophthalmic formulations of one or more active agents can include ingredients such as a preservative, a buffer and a thickening agent.

Suitable surface-active agents useful as a pharmaceutically acceptable carrier or excipient in the pharmaceutical compositions of the present invention include non-ionic, cationic and/or anionic surfactants having good emulsifying, dispersing and/or wetting properties. Suitable anionic surfactants include both water-soluble soaps and water-soluble synthetic surface-active agents. Suitable soaps are alkaline or alkaline-earth metal salts, non-substituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, non-substituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphtalenesulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidylcholine, dipalmitoylphoshatidyl-choline and their mixtures.

Suitable non-ionic surfactants useful as pharmaceutically acceptable carriers or excipients in the pharmaceutical compositions of the present invention include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants useful as pharmaceutically acceptable carriers or excipients in the pharmaceutical compositions of the present invention include quaternary ammonium salts, preferably halides, having 4 hydrocarbon radicals optionally substituted with halo, phenyl, substituted phenyl or hydroxy; for instance quaternary ammonium salts containing as N-substituent at least one $C_8$-$C_{22}$ alkyl radical (e.g. cetyl, lauryl, palmityl, myristyl, oleyl and the like) and, as further sub-stituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual " (MC Publishing Crop., Ridgewood, New Jersey, 1981), "Tensid-Taschenbuch", 2nd ed. (Hanser Verlag, Vienna, 1981) and "Encyclopaedia of Surfactants (Chemical Publishing Co., New York, 1981).

Structure-forming, thickening or gel-forming agents may be included into the pharmaceutical compositions and combined preparations of the invention. Suitable such agents are in particular highly dispersed silicic acid, such as the product commercially available under the trade name Aerosil; bentonites; tetraalkyl ammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antisettle).

In particular aspects, a pharmaceutically acceptable carrier is a particulate carrier such as lipid particles including liposomes, micelles, unilamellar or mulitlamellar vesicles; polymer particles such as hydrogel particles, polyglycolic acid particles or polylactic acid particles; inorganic particles such as calcium phosphate particles such as described in for example U.S. Pat. No. 5,648,097; and inorganic/organic particulate carriers such as described for example in U.S. Pat. No. 6,630,486.

A particulate pharmaceutically acceptable carrier can be selected from among a lipid particle; a polymer particle; an inorganic particle; and an inorganic/organic particle. A mixture of particle types can also be included as a particulate pharmaceutically acceptable carrier.

A particulate carrier is typically formulated such that particles have an average particle size in the range of about 1 nm-10 microns. In particular aspects, a particulate carrier is formulated such that particles have an average particle size in the range of about 1 nm-100 nm.

Detailed information concerning customary ingredients, equipment and processes for preparing dosage forms is found in Pharmaceutical Dosage Forms: Tablets, eds. H. A. Lieberman et al., New York: Marcel Dekker, Inc., 1989; and in L. V. Allen, Jr. et al., Ansel's Pharmaceutical Dosage Forms and Drug Delivery Systems, 8th Ed., Philadelphia, Pa.: Lippincott, Williams & Wilkins, 2004; A. R. Gennaro, Remington: The Science and Practice of Pharmacy, Lippincott Williams & Wilkins, 21st ed., 2005, particularly chapter 89; and J. G. Hardman et al., Goodman & Gilman's The Pharmacological Basis of Therapeutics, McGraw-Hill Professional, 10th ed., 2001.

Commercial packages according to aspects of the present invention include pharmaceutical compositions for use in treatment of a proliferative disorder in a subject including one or more of: a compound of structural formula I and/or II, a derivative of any thereof, a pharmaceutically acceptable prodrug form of any thereof, and/or a deuterated form of any thereof, and/or a pharmaceutically acceptable salt of any thereof.

Commercial packages according to aspects of the present invention include pharmaceutical compositions for use in treatment of a proliferative disorder in a subject including two or more of: a compound of structural formula I and/or II, a derivative of any thereof, a pharmaceutically acceptable prodrug form of any thereof, and/or a deuterated form of any thereof, and/or a pharmaceutically acceptable salt of any thereof, wherein the two or more are formulated in combination or separately.

Instructions for administering pharmaceutical compositions for use in treatment of a proliferative disorder in a subject including any of: a compound of structural formula I and/or II, a derivative of any thereof, a pharmaceutically acceptable prodrug form of any thereof, and/or a deuterated form of any thereof, and/or a pharmaceutically acceptable salt of any thereof, are included in commercial packages according to aspects of the invention. One or more ancillary components is optionally included in commercial packages of the present invention, such as a buffer or diluent.

Synthetic Method

According to methods of synthesis of compounds of the present disclosure, 4-quinolones are synthesized from flavones.

A method of synthesizing a 4-quinolone compound are provided according to aspects of the present disclosure which include contacting a flavone with a strong acid in a ratio of molar equivalents in the range of 1:2 to 1:100 in a closed system at a temperature in the range of 0° C. to 60° C. for a time period in the range of 2 hours to 10 days, producing a precipitate containing a corresponding flavylium salt. The strong acid can be any strong acid. According to aspects of the present disclosure, the strong acid is sulfuric acid. According to aspects of the present disclosure, the strong acid is not perchloric acid.

The flavylium salt is reacted with an amine, wherein the flavylium salt and amine are present a ratio of molar equivalents in the range of 1:3 to 1:5, in an aprotic solvent for a second time period in the range of 2 hours to 2 days, at ambient temperature, typically in the range of 10° C. to 30° C. producing a mixture including a 4-quinolone compound in the aprotic solvent. The 4-quinolone compound is then purified from the mixture.

According to aspects of the present disclosure, purifying the 4-quinolone compound from the mixture of 4-quinolone compound and aprotic solvent includes at least one of: 1) precipitation from an aprotic solvent such as hexane, acetone, ethyl acetate and mixtures in various proportions; 2) recrystallization with a protic solvent such as ethanol or isopropanol; and 3) using preparative plate chromatography method or column chromatography methods with material such as alumina (neutral or basic). Purified 4-quinolone compound is produced by methods according to the present disclosure at purities of 90-98%, with yields in the range of 10-90%.

According to aspects of the present disclosure, methods of synthesizing a 4-quinolone compound do not require protection of hydroxyl groups of the flavone, and therefore, optionally, such hydroxyl groups are not protected in methods of synthesizing a 4-quinolone compound according to aspects of the present disclosure.

Embodiments of inventive compositions and methods are illustrated in the following examples. These examples are provided for illustrative purposes and are not considered limitations on the scope of inventive compositions and methods.

EXAMPLES

Chemical Synthesis

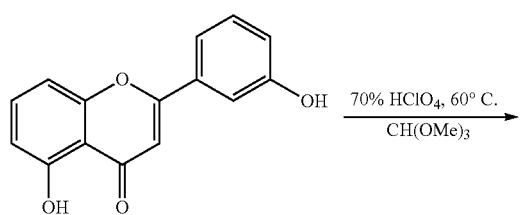

Scheme I

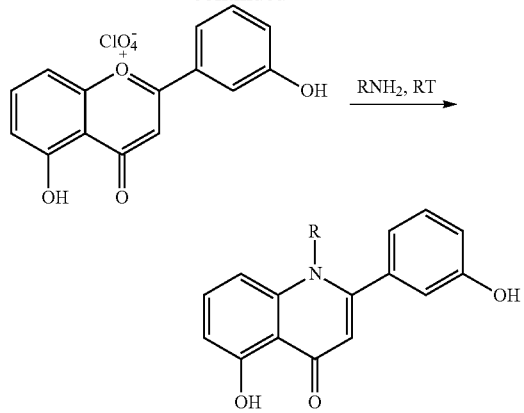

Scheme II

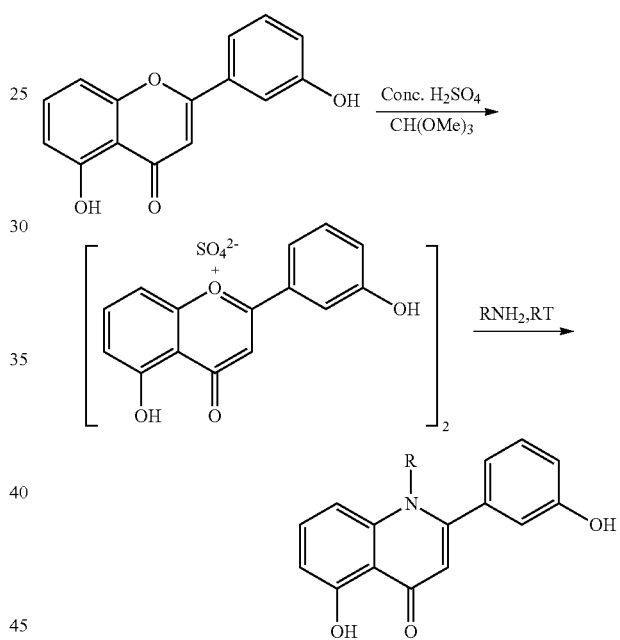

Chemical synthesis of compounds of structural formulas I and II was carried out per the Schemes I and II shown above using the corresponding procedures I and II described below.

Procedure I for Chemical Synthesis Using Scheme I

Step 1

0.254 g of 3'5 Dihydroxyflavone was suspended in 20 mL of trimethyl orthoformate. Then 0.2 mL of perchloric acid[1] (70%) was added slowly, with evolution of gas. The mixture was stirred for 2 hours at room temperature. The mixture was further stirred at 60° C. for 4 hours. The mixture was allowed to come to room temperature and 5 mL of ethyl acetate was added. The solids were filtered off, washed with 5 mL ethyl acetate and dried in air for 12 hours. The crude solid was used in the next step without purification.

Step 2

The intermediate from step 1 (0.040 mg) was weighed in a flask and suspended in 2 mL of neat amine (2,2,2 trifluoroethylamine)[2] when the color changed to orange. The mixture was stirred overnight. Progress of the reaction was monitored using solvent (Dichloromethane: Methanol 10:1). The solvents were evaporated and the crude solid[3] was purified by precipitation using acetone:hexane (10 mL:2 mL). The precipitated product was filtered, dried and spectral analysis was carried out. NMR (Nuclear Magnetic Resonance, $^1$H, $^{13}$C and $^{19}$F) and MS (Mass spectrometry) confirmed the structure of the pure product.

The equivalents of perchloric acid used can be 0.2-0.6 mL/mmoL of flavone.

The amine used as a reagent/solvent varies based on the R group on nitrogen. For example, ethyl amine was used when the R group is ethyl. The amine can be added in THF at 3 to 5 equivalents. However, when not used as solvent the conversion to product is not complete.

When the R group did not contain fluorine, the crude products were recrystallized from hot anhydrous ethanol.

Procedure I for Chemical Synthesis Using Scheme II

Step 1

1 mmol of flavone is suspended in 25 mL of trimethyl orthoformate or triethyl orthoformate. Then 1 mL of concentrated sulfuric acid (98%) is added slowly at room temperature, with evolution of gas 1. The mixture is stirred for 8-10 days at room temperature in a closed system attached to a bubbler. 20 mL of ethyl acetate is added to the mixture at room temperature. The solids are filtered off, washed with 5 mL ethyl acetate and dried in air for 2 hours. The crude solid is used in the next step without purification. The sulfate salts must be used immediately in the next step as residual methanol and moisture from the reaction cause the salts to break down to the starting flavone compound.

Step 2

The intermediate from step 1 (0.5 mmol) is weighed in a flask and suspended in 2 mL of neat amine when the color changes to orange[2]. The mixture is stirred overnight. The progress of the reaction is monitored by analytical thin layer chromatography using as solvent, dichloromethane: methanol (10:1). The solvent is evaporated and the crude solid is purified by precipitation using 12 mL acetone: hexane (5:1 ratio)[3]. The precipitated product is filtered off dried and spectral analysis is carried out. NMR (Nuclear Magnetic Resonance, $^1$H, $^{13}$C and $^{19}$F) and MS (Mass spectrometry) are used to confirm the structure of the pure product.

The temperature of the reaction reported in the literature, when perchloric acid is used, is 60° C. Perchloric acid needs to be heated very carefully to prevent drying to less than 30% water. As reported in the literature on the use of perchloric acid, during the reaction the perchloric acid could dry due to removal of water in situ. Human error in handling concentrated perchloric acid (>70%) could cause dangerous explosions. The synthetic step developed by us, with the use of sulfuric acid, is much safer than the perchloric acid procedure. However, it was found that the sulfuric acid salts decompose to the starting flavone in the presence of protic solvents such as methanol. NMR was used to monitor the conversion of flavone to the intermediate and assess stability of the sulfate salts. It was thus determined that the second synthetic step must be initiated immediately after completion of the first step.

The amine serves as both reactant and solvent and the amine compound used is based on the R group desired on nitrogen. For example, 2,2,2-trifluoroethylamine was used when the R group was trifluoroethyl. THF may be included as a solvent to reduce the amount of amine used; however, in this case the efficiency of conversion to product may be reduced.

When the R1 group does not contain fluorine, the crude products are recrystallized from hot anhydrous ethanol. For fluorinated derivatives, alumina is used for the purification using hexane:isopropanol (4:1 ratio) or dichloromethane: methanol (5:1 ratio).

A series of nine compounds with the basic scaffold of 5-Hydroxy-2-(3-hydroxyphenyl)-1-methylquinolin-4(1H)-one, structural formula II, in which the C ring nitrogen atom is attached to R groups with a range of hybrophobicities and steric features was synthesized as described above using Procedure I or II according to corresponding Schemes I or II.

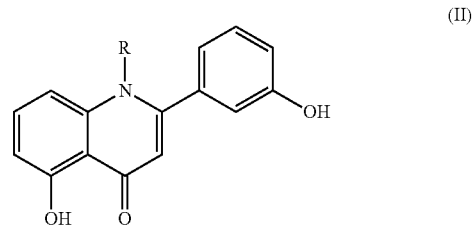

(II)

Particular compounds synthesized included structural formula II where R is a methyl group, also called KCI830 herein, where R is a propargyl group, also called KCI831 herein, where R is an ethyl group, also called KCI832 herein, where R is an n-propyl group, also called KCI833 herein, where R is an isopropyl group, also called KCI834 herein, where R is an isobutyl group, also called KCI835 herein, where R is a tert-butyl group, also called KCI836 herein, where R is a difluro-ethyl group, also called KCI837 herein, or where R is a trifluoro-ethyl group, also called KCI838 herein. All of these compounds were of at least 95% purity based on mass spectrometry, $^1$H NMR, $^{13}$C NMR and $^{19}$F NMR.

Established Cell Lines

22Rv1 cells, LNCaP cells, VCaP cells, DU145 cells, A549 cells, MDA-231 cells and HeLa cells were purchased from ATCC and frozen after less than 5 passages. The cells were therefore not further authenticated or tested for mycoplasma. The cells underwent <10 passages during the studies. The growth media used were as follows. For 22Rv1 cells, RPMI 1640 (phenol red-free), 10% FBS, 1% penicillin/streptomycin, 1% L-glutamine. For VCaP cells, DMEM high glucose (phenol red-free), 10% FBS, 1% penicillin/streptomycin, 1% L-glutamine, 1 nM dihydrotestosterone (DHT). For LNCaP cells, RPMI 1640 (phenol red-free), 10% FBS, 1% penicillin/streptomycin, 1% L-glutamine, 1% sodium pyruvate, 1% HEPES, 0.1 nM R1881. For DU145 cells, DMEM high glucose (phenol red-free), 10% FBS, 1% penicillin/streptomycin, 1% L-glutamine. For MDA-MB-231 cells, DMEM high glucose (phenol red-free), 10% FBS, 1% penicillin/streptomycin, 1% L-glutamine. For A549 cells, RPMI 1640 (phenol red-free), 10% FBS, 1% penicillin/streptomycin, 1% L-glutamine. For HeLa cells. DMEM high glucose (phenol red-free), 10% FBS, 1% penicillin/streptomycin, 1% L-glutamine.

Cell Viability Assay

Cells from monolayer cultures were trypsinized and seeded in 96-well plates coated with poly(d-lysine) at a density of 4000 cells per well (for 22Rv1 cells and LNCaP cells) or 5000 cells per well (for VCaP cells). The media used were the same as the growth media described above for each cell line. The plates were incubated at 37° C. in 5% CO2. Twenty-four hours later, the cells were treated with the indicated compound or dimethylsulfoxide (vehicle). The culture medium was replaced with fresh media containing vehicle or the appropriate concentration of compound at the end of 48 hours during the time course of the assay. Cell viability was determined on Day 0 and at the various time points using the standard 3-(4,5-dimethylthiazol-2-yl)-2,5-diphenyltetrazolium bromide (MTT) assay. The assays ware conducted in replicates of six wells per condition and values plotted as percent of the Day 0 values.

Colony Formation Assay

22Rv1 cells were plated in triplicate at a density of 2000 cells/well in 6-well plates in 48-hour conditioned medium (phenol-red free RPMI1640 10% FBS, 1% penicillin/streptomycin, 1% L-glutamine) obtained from monolayer cultures of the same cells, as previously described. 48 h after plating, the cells were treated with various concentrations of the test compounds in the same media. The test compounds and media were replenished every 48 hours until colonies developed in the control untreated wells (in 10 days). The colonies were then stained with crystal violet and counted.

RNA Isolation, Reverse Transcription, and Quantitative Real Time PCR

Total RNA from cells was isolated using the PureLink RNA Mini Kit (Invitrogen, ThermoFisher Scientific) according to the manufacturer's protocol. Reverse transcription was performed using 30 ng of total RNA and the High Capacity cDNA Reverse Transcription kit (Applied Biosystems, ThermoFisher Scientific) according to the vendor's protocol. cDNA was measured by quantitative real time PCR using the StepOnePlus Real-Time PCR System (Applied Biosystems, Invitrogen) and TaqMan Fast Universal PCR Master Mix (Applied Biosystems, ThermoFisher Scientific). All primers and TaqMan probes were purchased from the Applied Biosystems inventory (ThermoFisher Scientific). All samples were measured in triplicate and normalized to the values for GAPDH.

Hepatic Enzyme Induction

Primary human hepatocytes used were the "Cryo Human Hepatocytes" from Gibco. 24 hours prior to treatment, cells were plated at 350,000 cells/well (700,000 cells/mL) in the following media: Williams E medium (WEM, A1217601), 2.5 mL FBS, 5 µL, 10 mM dexamethasone (from Gibco Thawing/Plating Supplement Pack, CM3000), 1.8 mL thawing/plating cocktail (from Gibco Thawing/Plating Supplement Pack, CM3000). 5 hours after plating, media was replaced with the following media: Williams E medium (WEM, A1217601), 0.5 µL 10 mM dexamethasone (from Gibco Cell Maintenance Supplement Pack, CM4000), 2 mL cell maintenance cocktail (from Gibco Cell Maintenance Supplement Pack, CM4000). Treatment media was same as cell maintenance media listed above. Cells were treated with the control inducers (b-naphthoflavone, phenobarbital, dexamethasone and rifampin) or KCI 830 series compounds (0.5 uM, 5 uM and 50 uM), incubated at 37 degrees in 5% CO2 for 72 h and then harvested for RNA extraction. The mRNAs for the following hepatic enzymes were quantified as described above. Monooxygenases: CYP1A2, CYP2A6, CYP2B6, CYP2C9, CYP2C19, CYP3A4; Sulfotransferases: SULT1A1, SULT2A1; UDP-glucuronyltransferases: UGT1A1, UGT1A4, UGT1A6, UGT1A9, UGT2B4; UDP-glycosyltransferase: UGT2B7.

CYP1A2 Inhibition Assay

A stock solution of KCI838 was be prepared in DMSO at 50 mM and stored at −20° C. Serial dilutions of the stock solution were prepared in acetonitrile:DMSO (9:1) for CYP inhibition testing. The final DMSO content in the reaction mixture was equal in all solutions used within an assay, and was ≤0.2%. KCI838 was be incubated at seven increasing concentrations in with pooled human liver microsomes (Bioreclamation-IVT, Baltimore MD) in the presence of 2 mM NADPH in 100 mM potassium phosphate (pH 7.4) containing 5 mM magnesium chloride and the probe substrate, tacrine (5 uM), in a 200 µL assay (final volume). The selective CYP1A2 inhibitor α-naphthoflavone was screened alongside KCI838 as a positive control. After incubation for 10 min at 37° C. (Table 1), the reactions were terminated by addition of methanol containing internal standard for analytical quantification. The quenched samples were incubated at 4° C. for 10 min and centrifuged at 4° C. for 10 min. The supernatant was removed and the probe substrate metabolite analyzed by LC-MS/MS. A decrease in the formation of the metabolite compared to vehicle control was used to calculate an IC50 value (the test concentration that produces 50% inhibition).

TABLE 1

| Compound | Enzyme | Test Concentration | IC$_{50}$ (µM) |
|---|---|---|---|
| KCI838 | CYP1A2 | 0.1 µM-100 µM | 2.92 |
| a-naphthoflavone (control) | CYP1A2 | 0.001 µM-1 µM | 0.0192 |

UGT1A1 Inhibition Assay

KCI838 was incubated at seven increasing concentrations with human UGT1A1-expressed Supersomes™ (0.25 mg/mL), alamethicin (25 µg/mL) and UDPGA (5 mM) in the presence of the probe substrate estradiol (10 µM) for 30 min at 37° C. The UGT1A1 inhibitor, atazanavir, was screened alongside the test compounds as a positive control. The reactions were terminated by quenching with one volume of methanol containing an analytical internal standard. The samples will be centrifuged at 5000 rpm for 10 min at 4° C. The metabolites were monitored by LC-MS/MS and a decrease in the formation of the metabolite compared to the vehicle control was used to calculate an IC50 value (test compound concentration which produces 50% inhibition).

TABLE 2

| Compound | Enzyme | Test Concentration | IC$_{50}$ (µM) |
|---|---|---|---|
| KCI838 | UGT1A1 | 0.1 µM-100 µM | 35.9 |
| atazanavir (control) | UGT1A1 | 0.006 µM-0.6 µM | 0.792 |

Promoter Inhibition Assays

To measure ELK1-dependent promoter activation by AR, recombinant HeLa cells, which have a stably integrated minimal promoter-luciferase reporter containing five upstream Gal4 elements (Gal4-TATA-Luc) and constitutively express a GAL4-ELK1 fusion protein (in which the Gal4 DNA binding domain is substituted for the ETS DNA binding domain of ELK1), as well as full-length AR, were used. To measure androgen response element (ARE)-driven promoter activation by AR, we used recombinant HeLa cells harboring a minimal promoter-luciferase reporter with an upstream ARE sequence (ARE-TATA-Luc) and also stably expressing full-length AR. The two types of recombinant cells were grown in DMEM supplemented with 5% FBS or 10% FBS, respectively, and 100 units/mL penicillin, 100 µg/mL streptomycin, 2 mM L-glutamine mixture (Invitrogen). The selection antibiotics used in maintenance cultures of the two recombinant cell types were 100 µg/mL Hygromycin (Invitrogen) (to maintain GAL4-ELK1), 100 µg/mL Geneticin (Invitrogen) (to maintain Gal4-TATA-Luc) and 2 µg/mL Puromycin (Sigma-Aldrich) (to maintain AR) and 400 ug/mL Geneticin (Invitrogen) (to maintain ARE-TATA- Luc). The cells were hormone-depleted 24 hours prior to screening in media containing heat-inactivated, charcoal-stripped serum. Cells were then plated in 96-well white flat bottom plates (20,000 cells/well) (Corning product #3917) and incubated for approximately 18 hours prior to treatment. The following day, cells were treated with the appropriate doses of test compounds along with testosterone or dihydrotestosterone (DHT) (final concentration, 1 nM), using 6 replicate wells per dose. Vehicle controls (DMSO, 0.1% v/v) were included. The plates were incubated for 6 hours at 37° C. in 5% CO2. The media was then aspirated and 20 µL of Promega Glo Lysis Buffer (Promega #E2661) was added to each well, and then the plates were incubated at room temperature for 10-15 minutes on an orbital shaker. Luciferase activity was measured for each well using firefly luciferase substrate from the Luciferase Assay System (Promega) in a luminometer (Centro XS3 LB 960, Berthold, Wildbad, Germany).

AR Target Gene Expression Assays

22Rv1 cells were grown in RPMI supplemented with 10% FBS and 100 units/mL penicillin, 100 µg/mL streptomycin, 2 mM L-glutamine mixture (Invitrogen). The day before treatment, cells were plated in poly-D lysine coated plates (100,000 cells/well) (Corning #354461) in phenol red-free growth media. The following day, cells were treated with 10 µM of each compound or DMSO vehicle (0.1% v/v). Cells were incubated for 72 hours at 37° C. in 5% CO2, with treated media replenished at 48 hours. At 72 hours, total RNA from cells was isolated using the PureLink RNA Mini Kit (Ambion, Invitrogen) according to the manufacturer's protocol. Reverse transcription was performed using 250 ng of total RNA and the High Capacity cDNA Reverse Transcription Kit (Applied Biosystems, Invitrogen) according to the manufacturer's protocol. cDNA was measured by quantitative real time PCR using the StepOnePlus Real-Time PCR System (Applied Biosystems, Invitrogen) and TaqMan Fast Universal PCR Master Mix (Applied Biosystems, Invitrogen). All primers and TaqMan probes were purchased from the Applied Biosystems inventory (Invitrogen). Samples were measured in triplicate and normalized to the values for GAPDH.

BRET Assay for Inhibition of In Situ Binding of AR to ELK1 by KCI838

HEK293T cells were transfected with Rluc-AR alone, and alongside Turbo-Elk at a 4:1 ratio of ELK1:AR using Mirus LT1 reagent. The 4:1 ratio was determined to be the optimal ratio for the inhibition assay after testing different ratios of Turbo-Elk:Rluc-AR. 24 hours later, cells were treated with DMSO (vehicle control) or KCI838 (0.4 uM and 10 uM) and left for 24 hours. They were then trypsinized and seeded in 96 well white-bottomed plates at 100,000 per well (in quadriplicate) in media lacking phenol red (with DMSO or drug as required), left for 2 hours to settle, and then treated with 25 uM coelenterazine and luminescence read at 535 and 635 nm on a Clariostar instrument. BRET readings were calculated as 635/535 ratio minus 635/535 ratio for Rluc-AR only transfected controls. Cell lysates were probed by western blot for AR or ELK1, probing for GAPDH as the loading control. Cell viability in the presence of KCI838 was ensured by treating HEK293 cells for an extended period (3 days) with the compound or vehicle control and measuring viability using trypan blue staining.

Generation of Recombinant 22Rv1 Cells Overexpressing AR

AR expressing lentiviral expression plasmid pCDH-CMV-MCS-EF1-puro (System BioSciences) or the plasmid vector alone (control), was packaged in 293FT cells. Virus-containing media was harvested at 48 and 72 hours after packaging and stored at −80° C. 48 hours before infection, 22Rv1 cells were plated at 30-50% confluence in 10 cm dishes in phenol-red free medium supplemented with 10% heat-inactivated FBS and 2 mM L-glutamine. On the day of infection, cells were infected with the lentivirus with polybrene (8 µg/mL) for a duration of 5 hours. The virus was then replaced with fresh medium containing 10% FBS and 100 units/mL penicillin, 100 µg/mL streptomycin, and 2 mM L-glutamine mixture. Cells were placed under puromycin selection for at least 4 passages, at a previously optimized concentration of 0.4 ug/mL puromycin to select for the pools of transduced cells.

Statistical Methods

In all the graphs, the error bars represent standard deviation. Statistical analysis was performed using two-sample t-test or one-way ANOVA with post-hoc LSD (Least Square Differences).

Results

Compounds of structural formulas I and II were screened for growth inhibitory activity in monolayers of the enzalutamide-resistant 22Rv1 CRPC cells, comparing both the time course of growth inhibition using 3 compound doses (2.5 uM, 5 uM and 10 uM), results shown in FIGS. 1A to 1J). Whereas enzalutamide did not inhibit cell growth. See FIG. 1A, demonstrating inhibitory activity, see FIGS. 1B-1J. Compound 1 (called KCI838 herein) showed the earliest onset of growth inhibition among all the compounds, with virtually complete growth inhibition observed at all concentrations tested, see FIG. 1J.

The dose-dependence of cumulative growth inhibition at the end of 4 days of treatment was tested for compounds of structural formulas I and II in the dose range of 0.625 uM-10 uM and results are shown in FIGS. 2A-2I. KCI838 showed the most effective dose response for growth inhibition, see FIG. 2I.

KCI838 Inhibits Colony Formation in Enzalutamide Resistant CRPC Cells

Figure 3A:
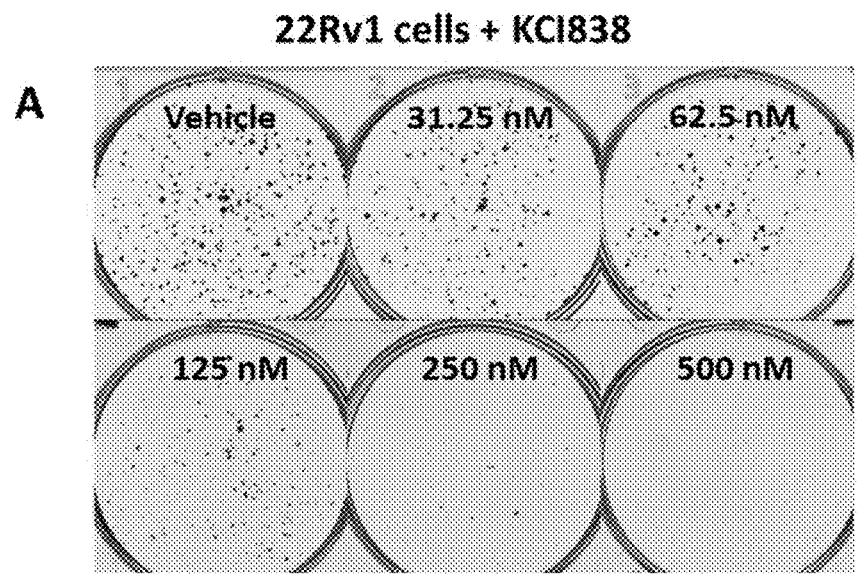
FIG. 3A is an image showing results of tests indicating that KCI838 inhibits colony formation in enzalutamide resistant 22Rv1 cells.
Figure 3B:
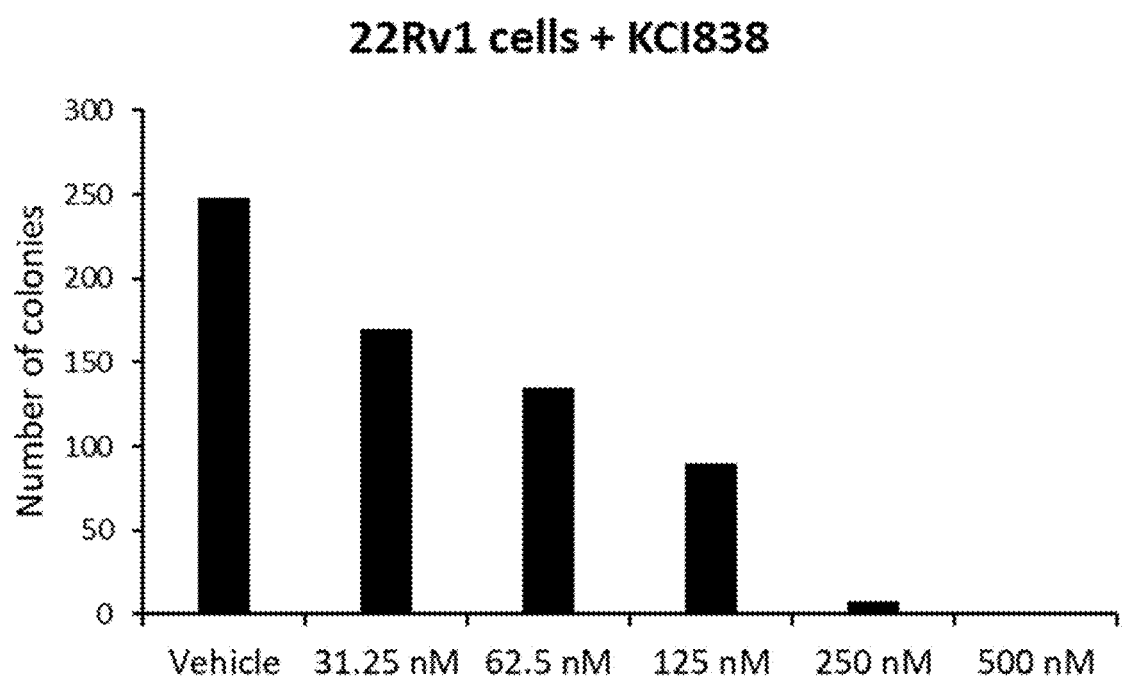
FIG. 3B is a graph showing results of tests indicating that KCI838 inhibits colony formation in enzalutamide resistant 22Rv1 cells.
Figure 3C:
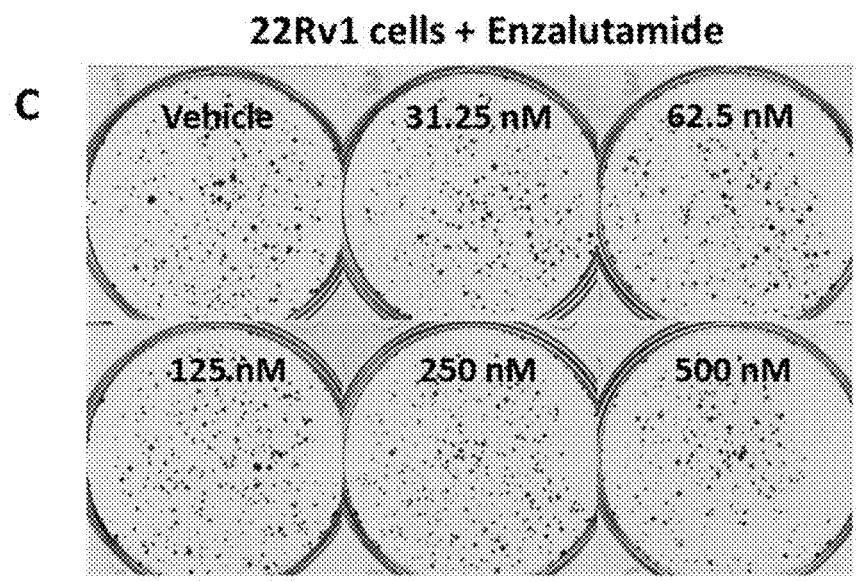
FIG. 3C is an image showing results of tests assessing the effect of enzalutamide on colony formation in enzalutamide resistant 22Rv1 cells.
Figure 3D:
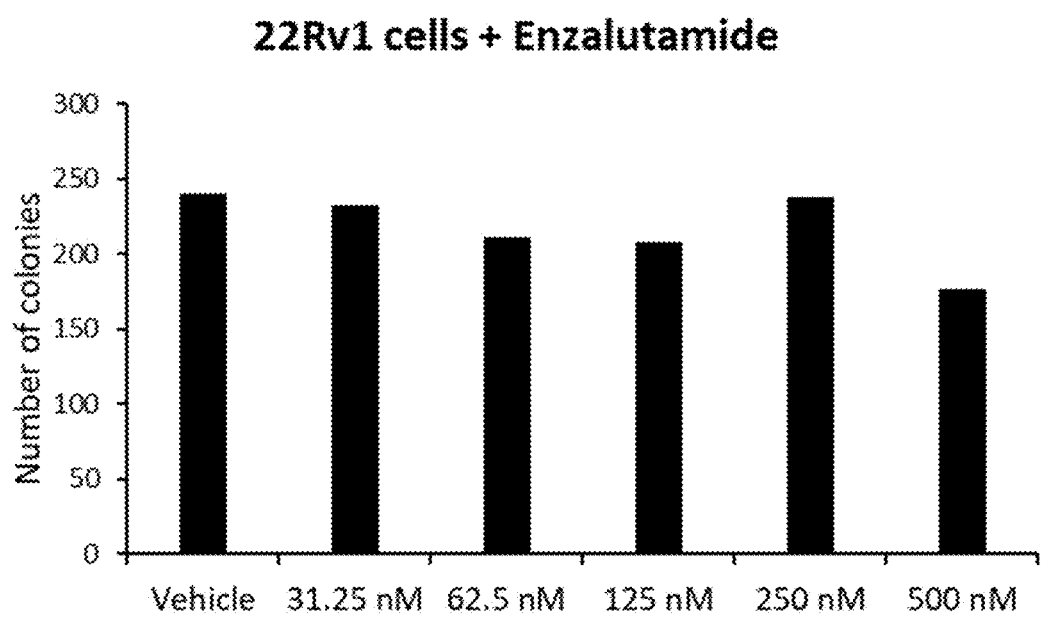
FIG. 3D is a graph showing results of tests assessing the effect of enzalutamide on colony formation in enzalutamide resistant 22Rv1 cells.

In 22Rv1 CRPC cells, KCI 838 inhibited colony formation in the nanomolar dose range, see FIG. 3A, with the colony counts showing an IC50 of ~60 nM, see FIG. 3B. In contrast, enzalutamide had no effect on colony formation in the same dose range, see FIG. 3C and FIG. 3D).

Figure 4A:
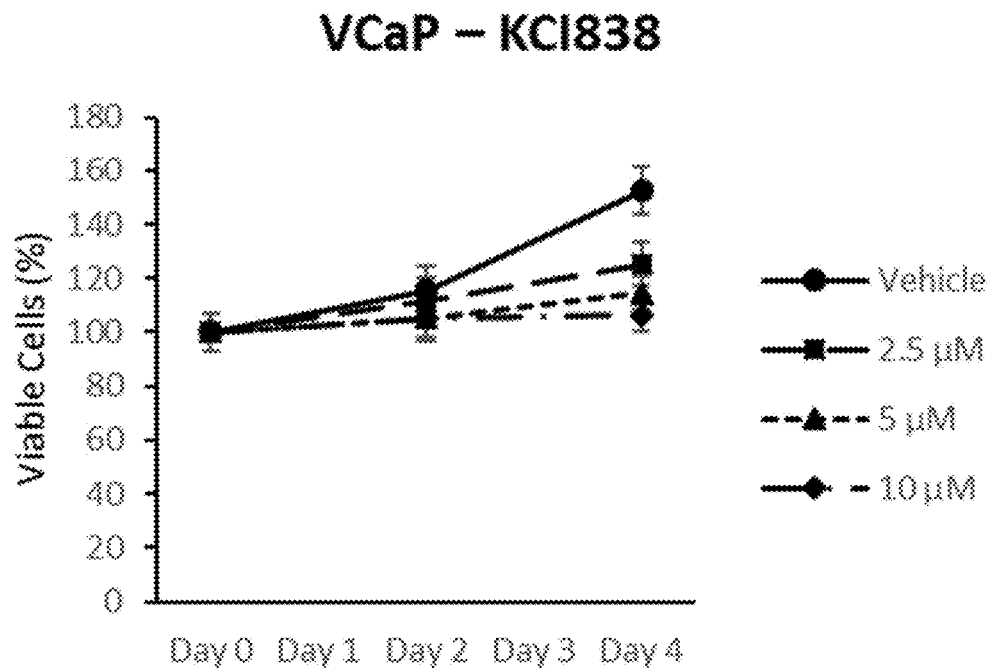
FIG. 4A is a graph showing results of tests assessing the effect of KCI838 on VCaP cells.
Figure 4B:
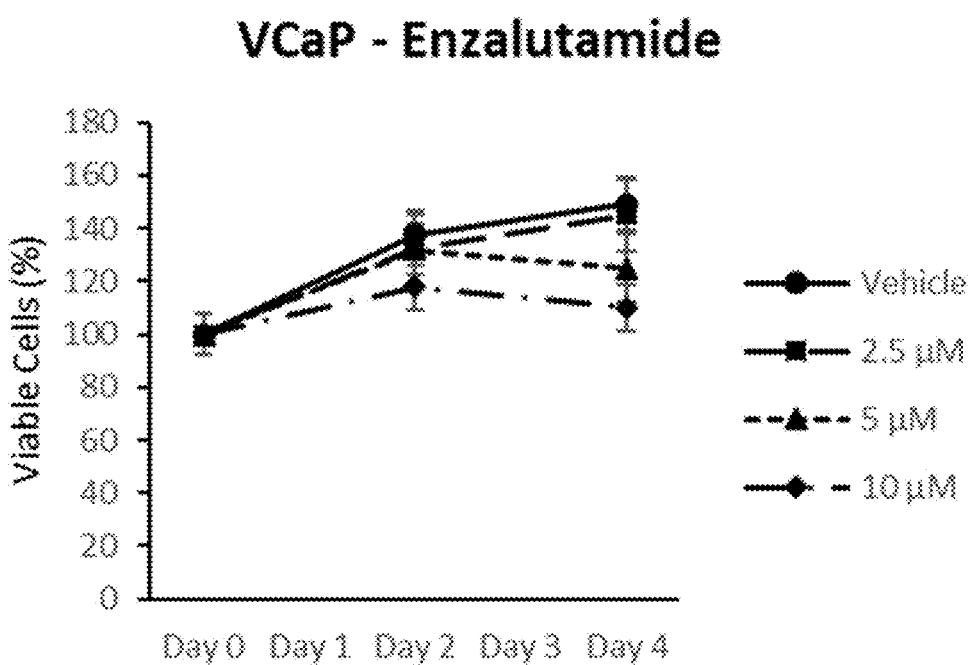
FIG. 4B is a graph showing results of tests assessing the effect of enzalutamide on VCaP cells.
Figure 4C:
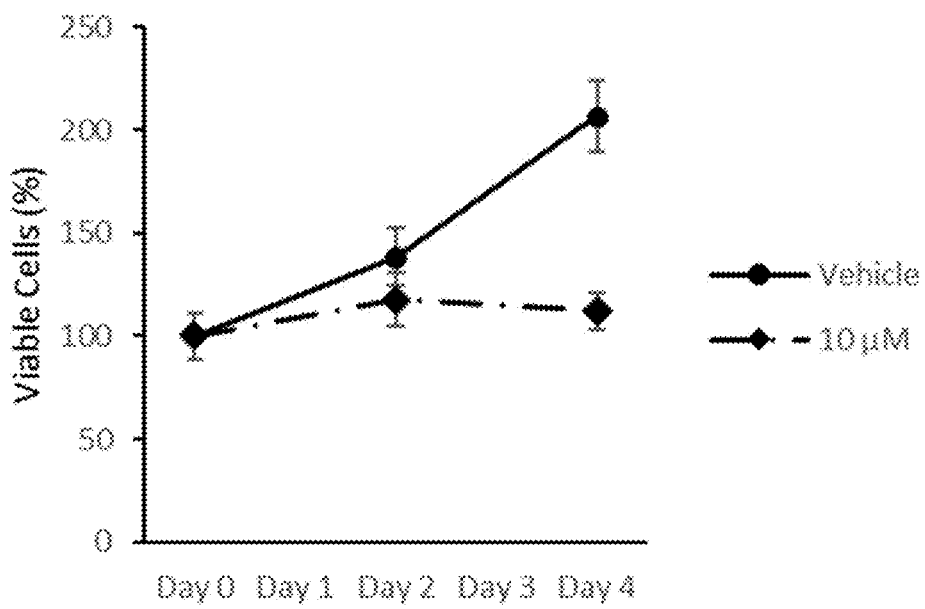
FIG. 4C is a graph showing results of tests assessing the effect of KCI838 on LNCaP cells.
Figure 4D:
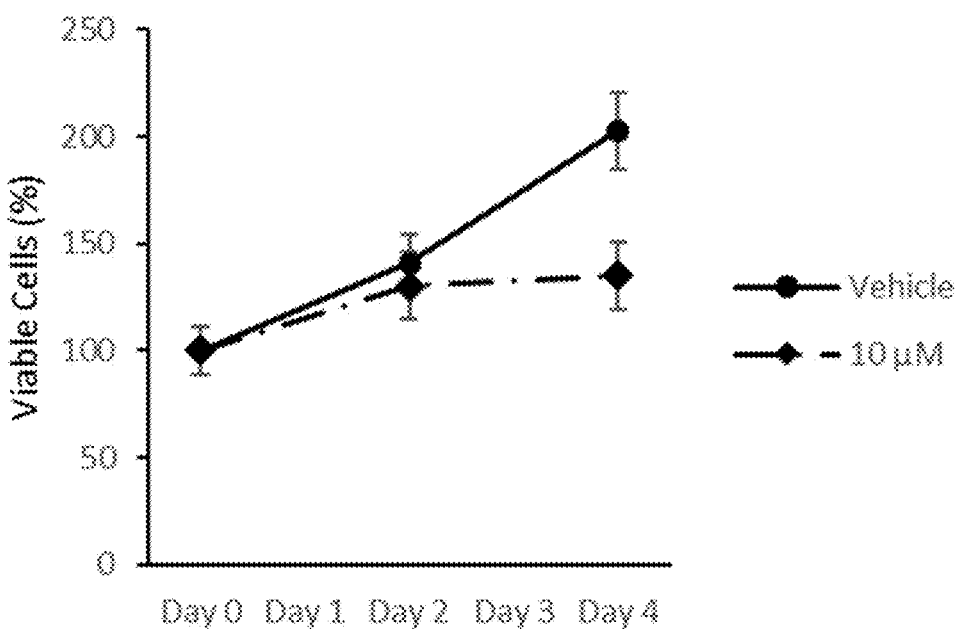
FIG. 4D is a graph showing results of tests assessing the effect of enzalutamide on LNCaP cells.
Figure 5A:
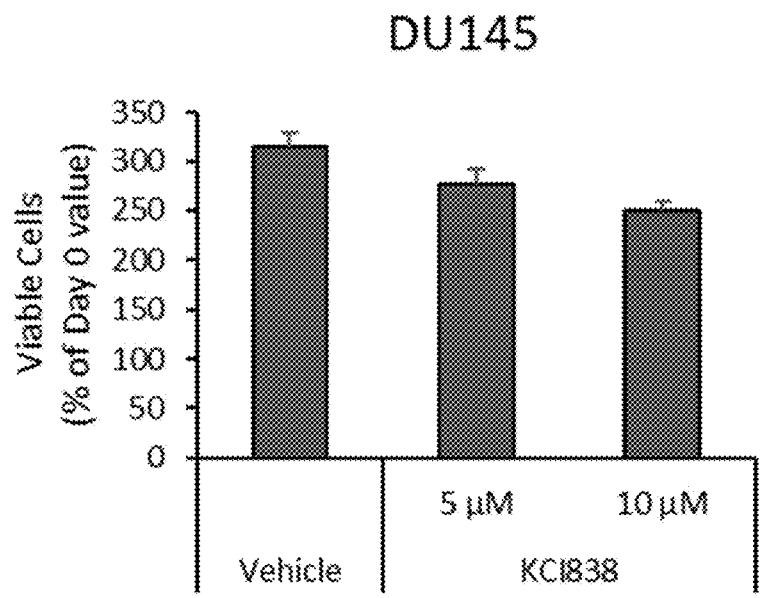
FIG. 5A is a graph showing that growth inhibition by KCI838 is selective for androgen receptor-dependent cells, illustrated by lack of significant effect on on DU145 cells.
Figure 5B:
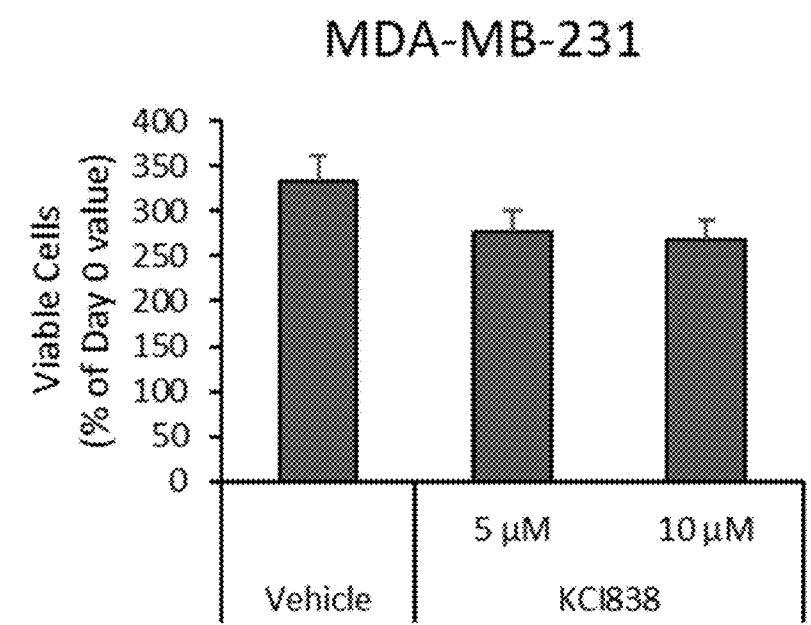
FIG. 5B is a graph showing that growth inhibition by KCI838 is selective for androgen receptor-dependent cells, illustrated by lack of significant effect on MDA-MB-231 cells.
Figure 5C:
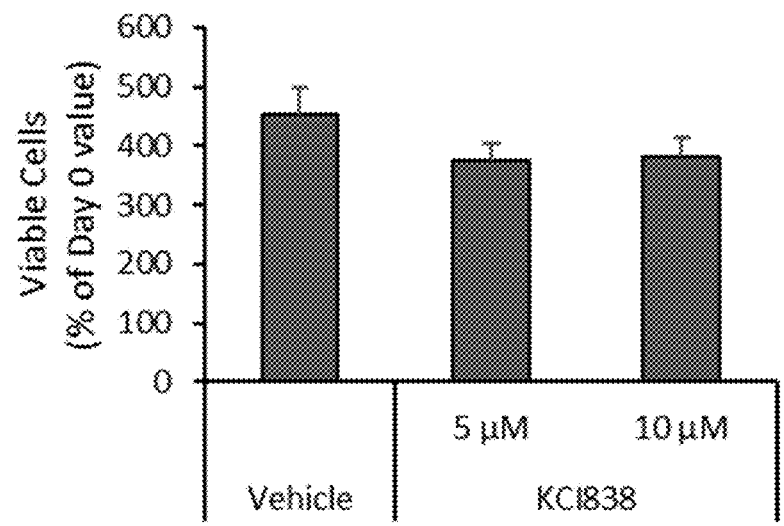
FIG. 5C is a graph showing that growth inhibition by KCI838 is selective for androgen receptor-dependent cells, illustrated by lack of significant effect on A549cells.
Figure 5D:
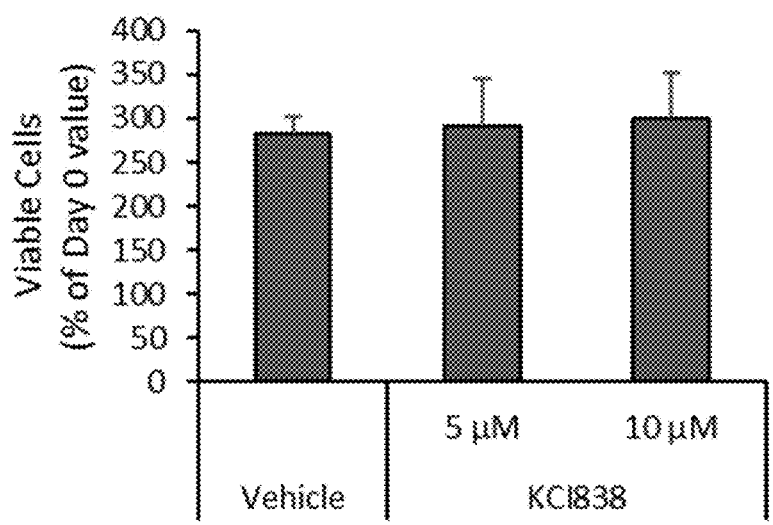
FIG. 5D is a graph showing that growth inhibition by KCI838 is selective for androgen receptor-dependent cells, illustrated by lack of effect on HeLa cells.
Figure 6A:
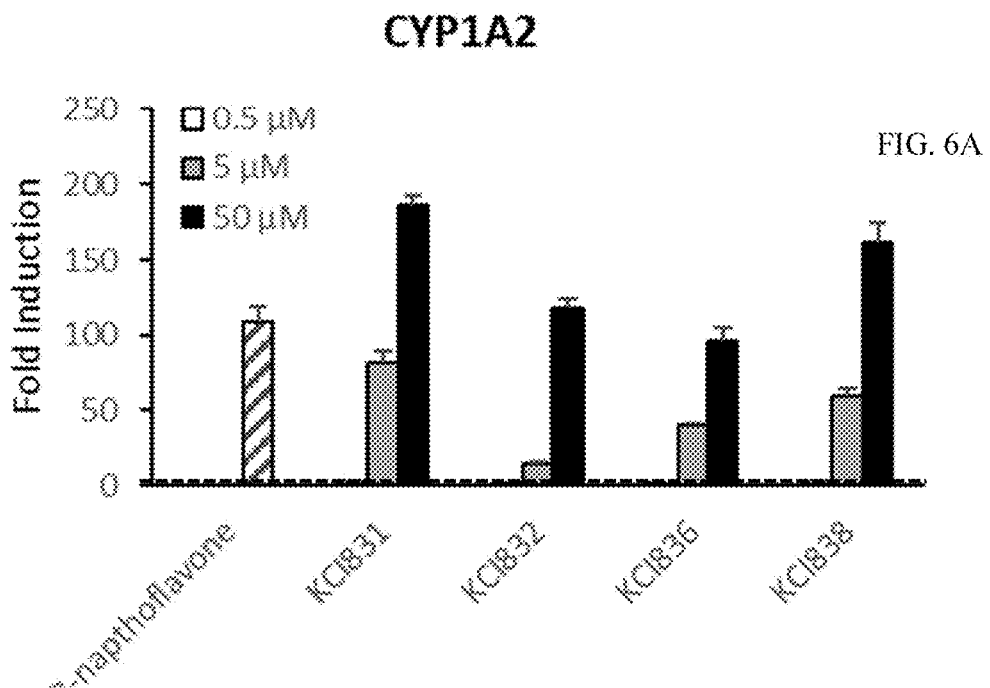
FIGS. 6A, 6B, 6C, 6D, 6E, and 6F, are graphs showing results of assays demonstrating that compounds according to aspects of the present disclosure are relatively poor inducers of drug metabolizing enzymes.
Figure 6B:
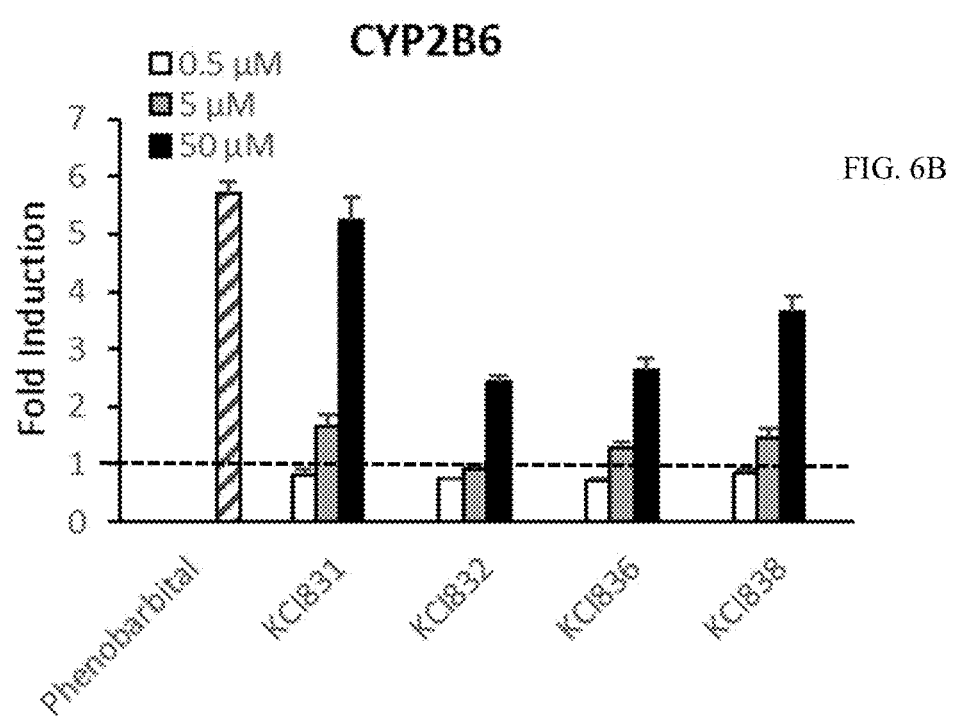
Figure 6C:
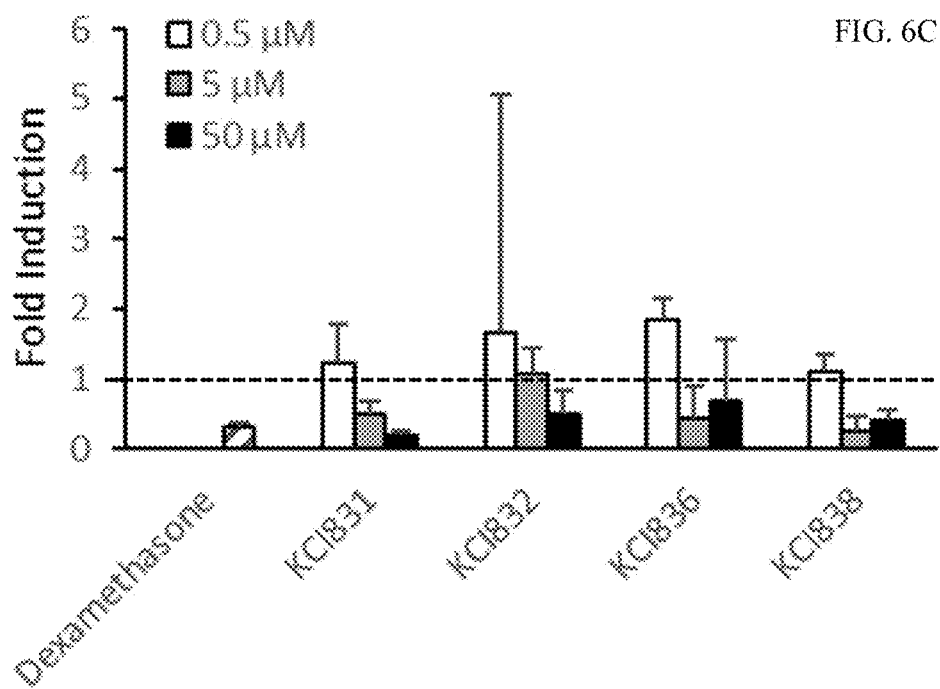
Figure 6D:
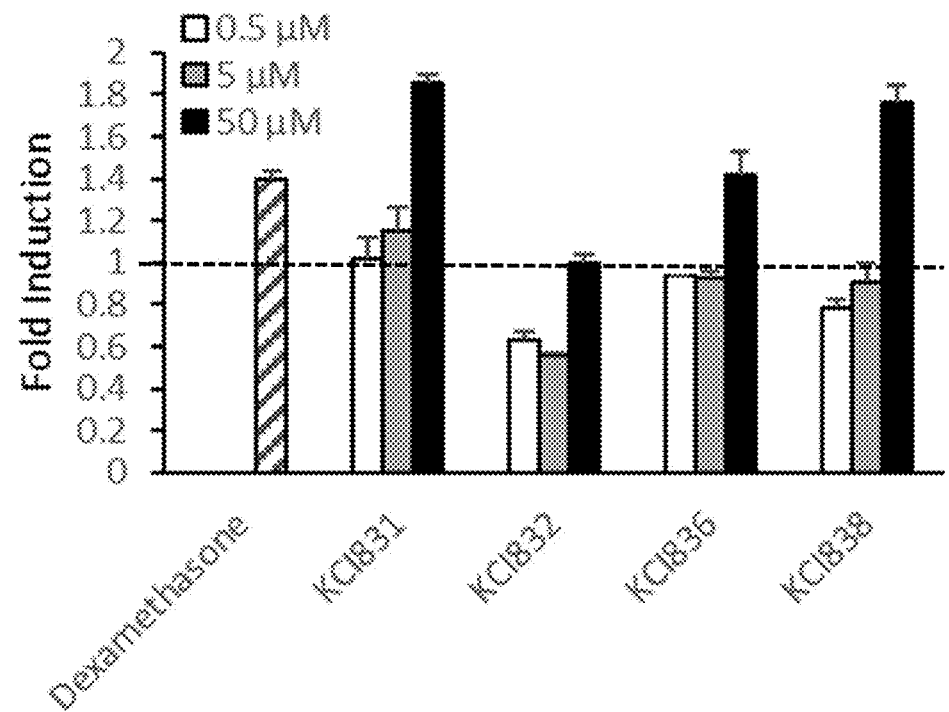
Figure 6E:
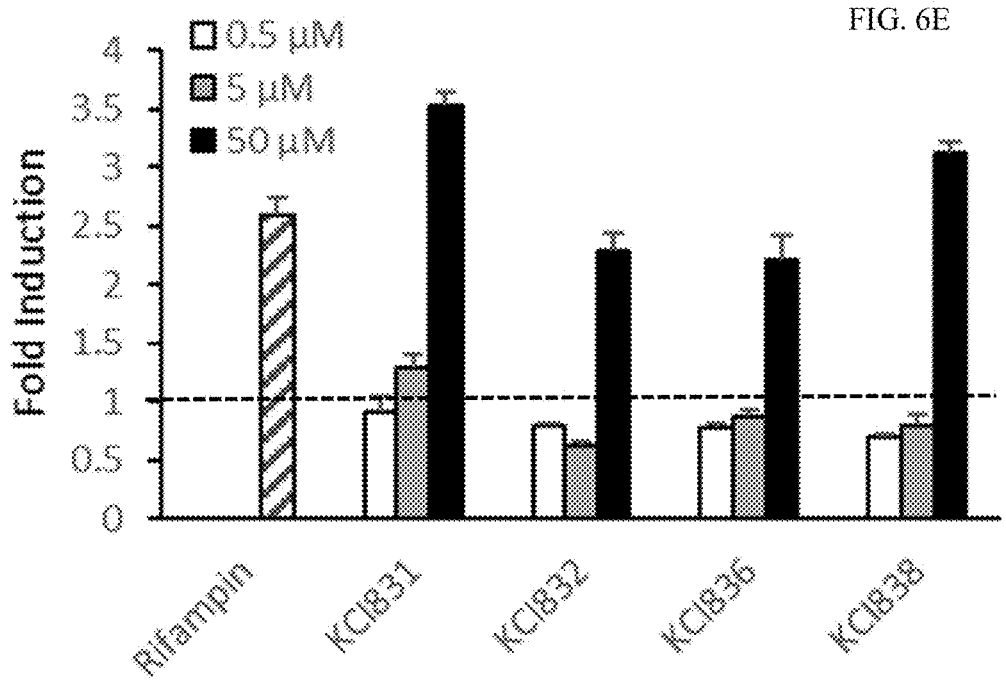
Figure 6F:
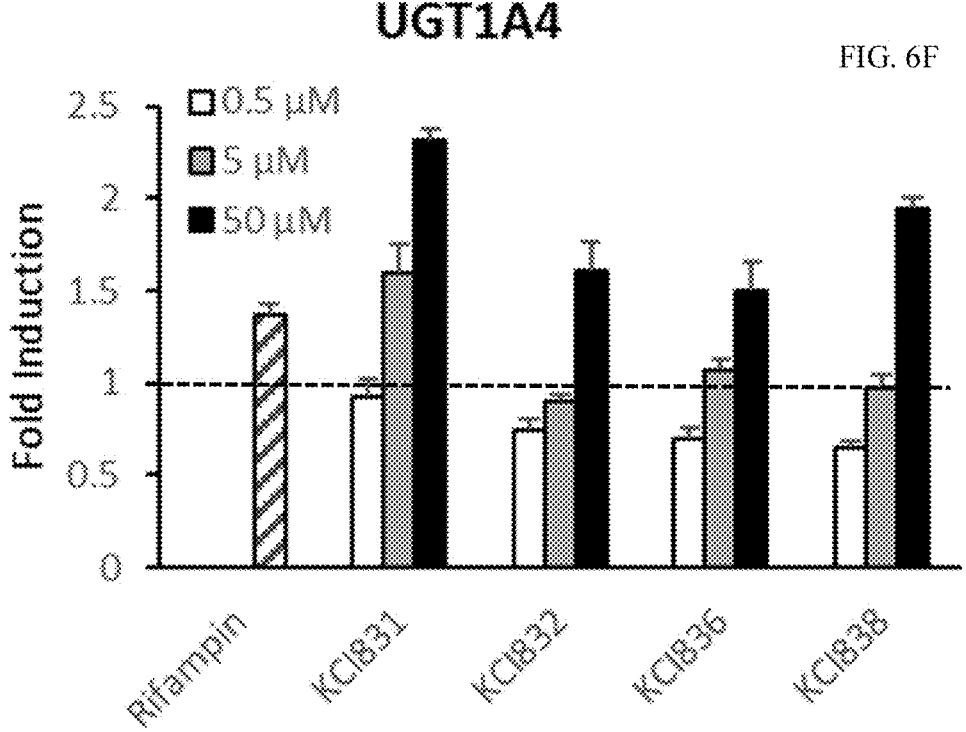

KCI838 Inhibits Growth in Other AR-Dependent PCa Cell Lines Better than Enzalutamide When tested in the dose range of 2.5 uM-10 uM, both KCI838 and enzalutamide inhibited monolayer growth of the androgen-dependent VCaP PCa cell line in a dose-dependent manner, see FIGS. 4A and 4B, respectively. Inhibition of monolayer growth in the androgen-dependent LNCaP PCa cells was compared between KCI838 and enzalutamide, at a dose of 10 uM. KCI838 showed more effective growth inhibition than enzalutamide in LNCaP cells, see FIG. 4C and FIG. 4D, respectively.

KCI838 is Inactive in AR-Negative Cell Lines

The effect of KCI838 on monolayer growth was tested in four AR-negative cancer cell lines and results are shown in FIGS. 5A-5D). KCI 838 did not significantly affect growth of the AR-negative cell lines including DU145 PCa cells, FIG. 5A, MDA-MB-231 breast cancer cells, FIG. 5B, A549 lung cancer cells, FIG. 5C, and HeLa cervical cancer cells, FIG. 5D.

KCI830 Series Compounds are Poor Inducers and Substrates for Major Human Hepatic Enzymes that Metabolize Drug Molecules FIGS. 6A, 6B, 6C, 6D, 6E, and 6F show induction of major hepatic enzymes by four selected compounds of the present disclosure, KCI831, KCI832, KCI836 and KCI838 when primary human hepatocytes were exposed to the compound for 72 hours. Among monooxygenases, KCI831, KCI836 and KCI838 were unable to induce CYP1A2 at the 0.5 uM dose although they induce the enzyme at higher doses. Perhaps more important, the quinolone scaffold in the KCI830 series compounds is known to be an inhibitor rather than a substrate for CYP1A2. Likewise, the compounds were relatively poor inducers of the monooxygenase CYP2B6 for which again the quinolone scaffold of these compounds may not serve as a substrate. Other monooxygenases were not induced by any of the compounds. The major UDP-glucuronyl transferases (that glucuronylate drugs) UGT1A1 and UGT1A4 were not induced significantly by KCI832, KCI836 and KCI838 at doses of 0.5 uM and 5 uM while KCI831 showed modest induction (1.2-1.5 fold) at these doses; significant induction of UGT1A1 and UGT1A4 was only observed at a dose of 50 uM of the compounds. Induction of sulfotransferases or glycosyltransferase by the compounds was modest or absent, see FIGS. 6C and 6D.

KCI838 Interacts Poorly with CYP1A2 and UGT1A1

Figure 7A:
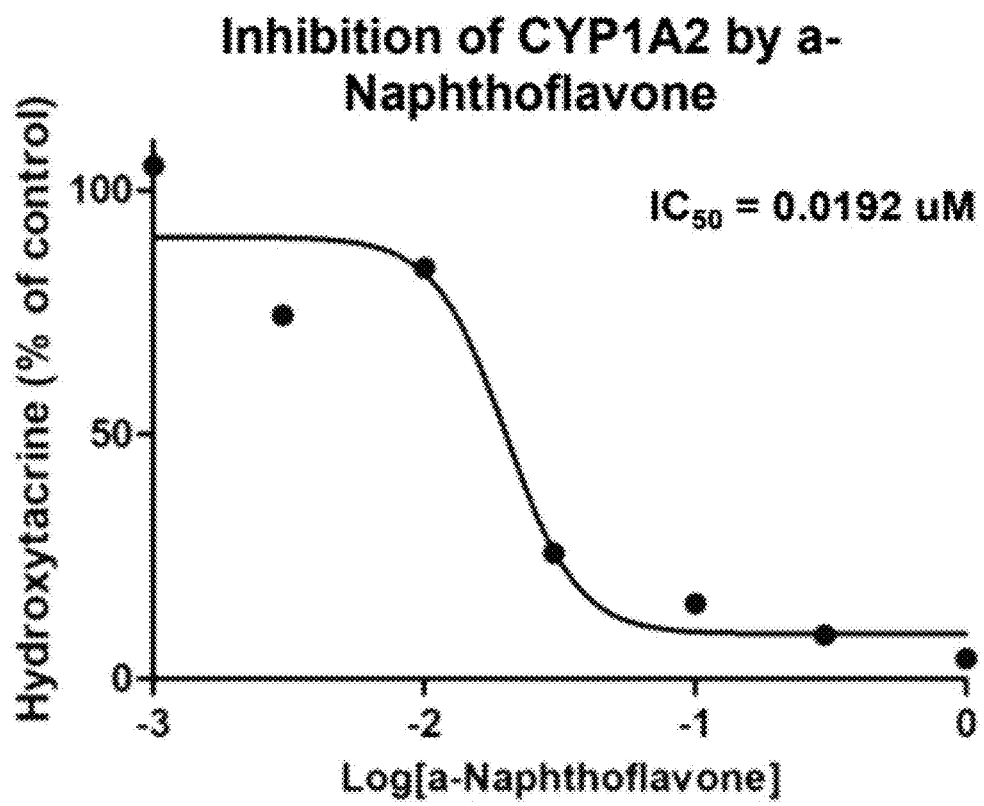
FIGS. 7A and 7B together show that KCI838 interacts relatively weakly with CYP1A2.
Figure 7B:
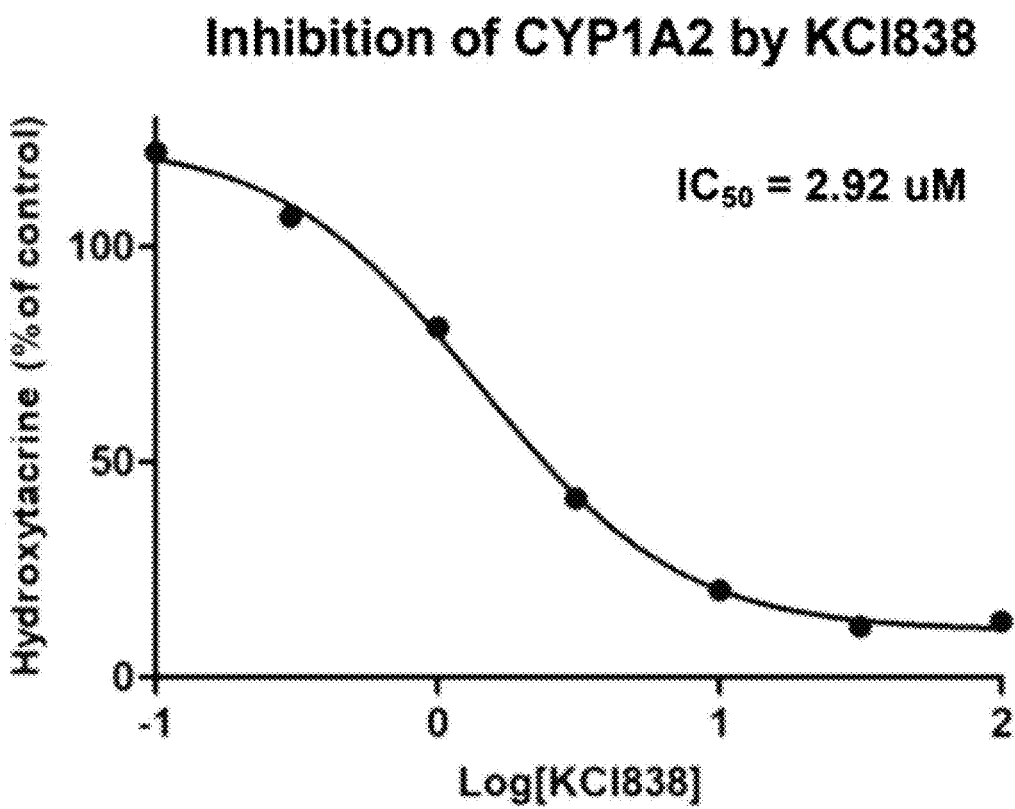
Figure 8A:
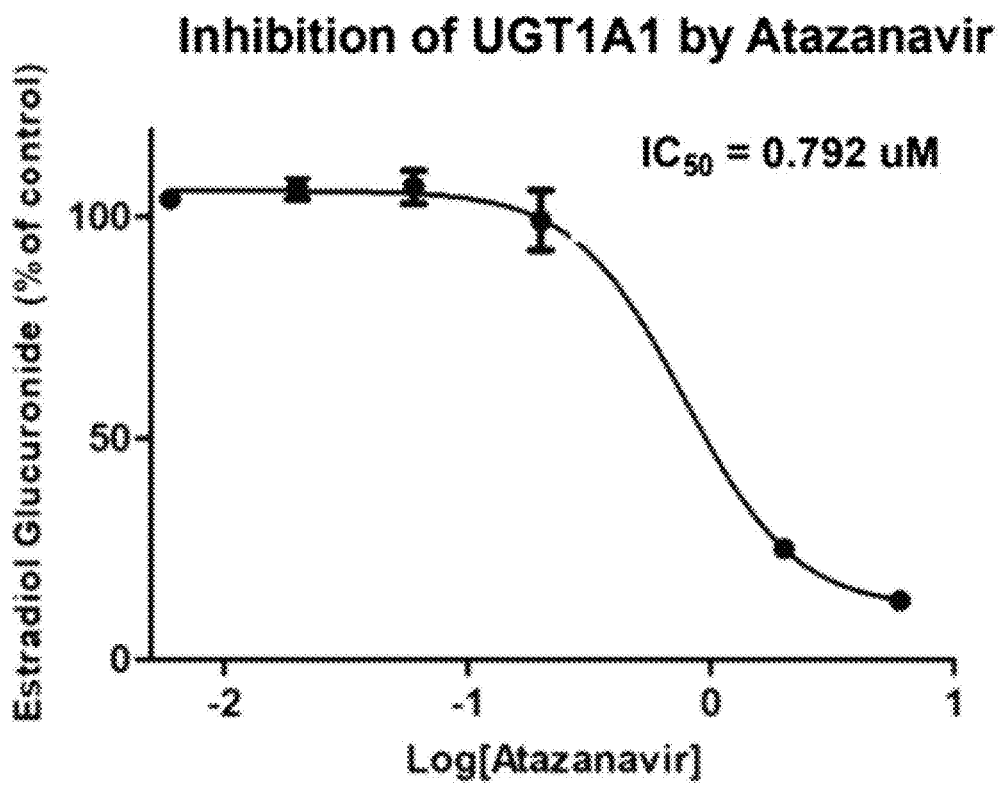
FIGS. 8A and 8B together show that KCI838 is a relatively weak substrate for glucuronylation.
Figure 8B:
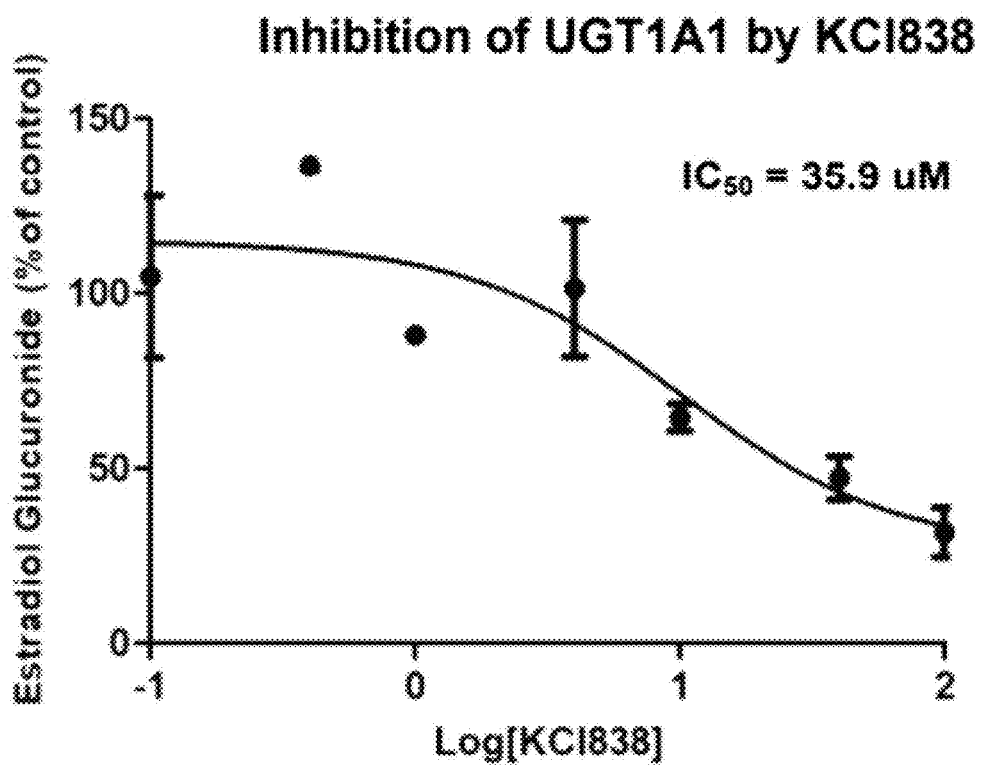

The interaction of KCI838 to interact with the major human liver monooxygenase CYP1A2, see FIGS. 7A and 7B, and the major human UDP-glucuronyl transferase UGT1A1, see FIGS. 8A and 8B, (i.e., the ability of the compound to serve as inhibitor or substrate for the enzymes) was examined by determining the IC50 values of the compound in standard enzymatic activity assays using the specific substrates described. The IC50 value of KCI838 was relatively high for CYP1A2 compared with the control inhibitor (2.92 uM vs. 0.0192 uM). The IC50 value of KCI838 was also relatively high for UGT1A1 compared with the control inhibitor (35.9 uM vs. 0.792 uM), see FIGS. 8A and 8B.

In Vivo Activity

KCI838 was repeatedly administered by intraperitoneal injection to two groups of 6-week old male BalbC mice at doses of 200 mg/Kg and 100 mg/Kg. The mice showed no apparent signs of toxicity. The mice initially showed a small amount of dose-dependent weight loss (~4% and 2%, respectively at 200 mg/Kg and 100 mg/Kg) indicating drug activity.

ELK1-Dependent Transcriptional Activation by AR is Selectively Inhibited by KCI838

Figure 9C:
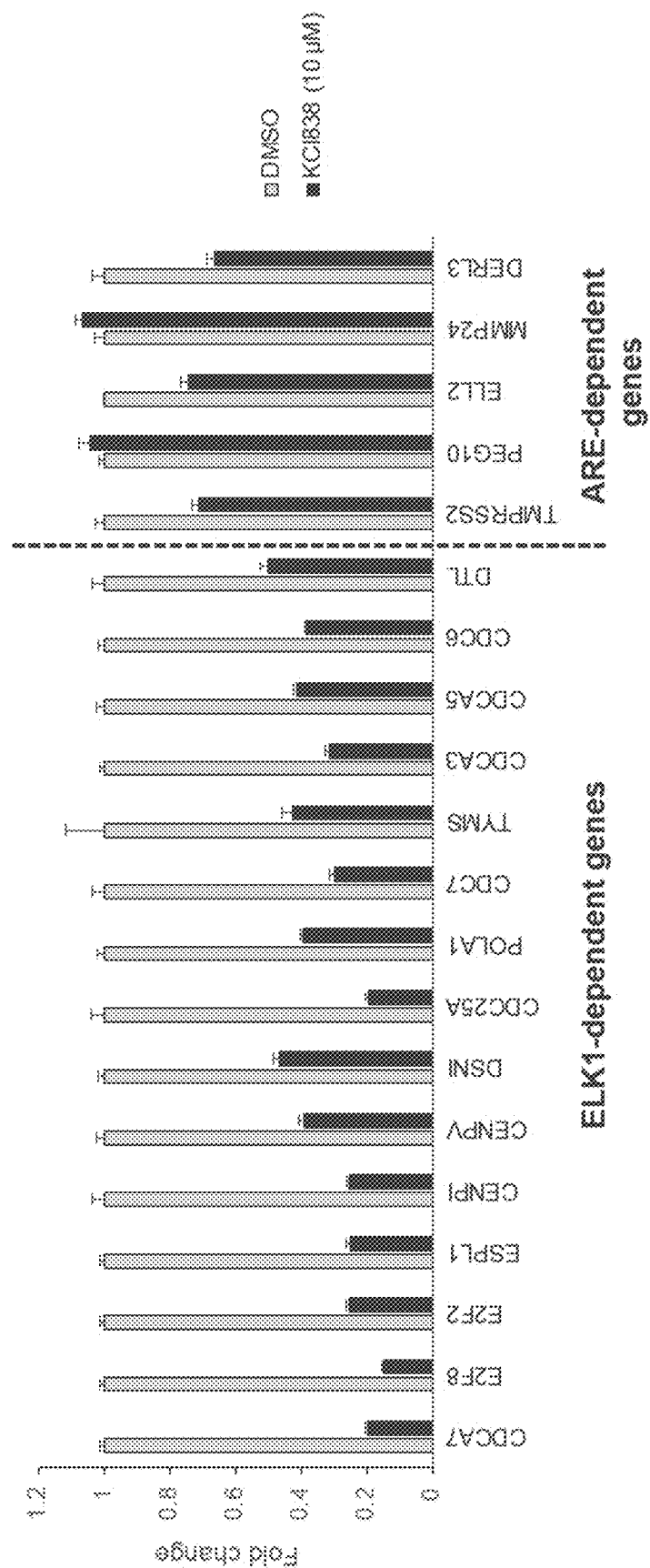
FIG. 9C is a graph showing that KCI838 inhibits ELK1-dependent gene activation by AR selectively compared with ARE-dependent gene activation.

The ability of KCI838 to selectively disrupt functional interactions between AR and ELK1 is illustrated in FIGS. 9A, 9B, and 9C.

Recombinant HeLa cells harboring a Gal4 containing minimal promoter-luciferase reporter construct (Gal4-TATA-Luc) and stably expressing ectopic GAL4-ELK1 fusion protein as well as ectopic AR were used in a first test. These recombinant HeLa cells harboring the Gal4-Elk1-TATA-Luc promoter-reporter and constitutively expressing AR and the GAL4-ELK1 fusion protein were plated in phenol red-free media. The following day, they were treated for 6 hours with the indicated doses of KCI838 and 10 nM DHT, see FIG. 9A. Promoter activity was measured as reporter luciferase activity. The results show that promoter activation by dihydrotestosterone was inhibited by KCI838 in a dose-dependent manner, see FIG. 9A.

In a further test, recombinant HeLa cells harboring the ARE-TATA-Luc promoter-reporter and constitutively expressing AR were plated in phenol red-free media. The following day, they were treated for 6 hours with the indicated doses of KCI838 and 10 nM testosterone, see FIG. 9B. Promoter activity was measured as reporter luciferase activity. Results show that in recombinant HeLa cells harboring a classical androgen response element (ARE)-driven promoter (ARE-TATA-Luc) and stably expressing ectopic AR, KCI838 was unable to inhibit promoter activation by dihydrotestosterone, see FIG. 9B.

In a further test, 22Rv1 cells were treated for 72 hours with vehicle or 10 uM KCI838. Total RNA was recovered from the cells and quantitative RT-PCR was used to measure mRNAs of the genes indicated in FIG. 9C. The control vehicle value was normalized to 100 percent for each gene. P-value *=<0.05,  <0.01, * <0.01. The results show that when the 22Rv1 PCa cells were treated with KCI838, KCI838 selectively inhibited the expression of known ELK1-dependent endogenous target genes of AR, compared with classical ARE-driven gene targets of AR, see FIG. 9C.

FIG. 9A is a graph showing that in recombinant HeLa cells harboring a Gal4 containing minimal promoter-luciferase reporter construct (Gal4-TATA-Luc) and stably expressing ectopic GAL4-ELK1 fusion protein as well as ectopic AR, promoter activation by dihydrotestosterone was inhibited by KCI838 in a dose-dependent manner.

FIG. 9B is a graph showing that in recombinant HeLa cells harboring a classical androgen response element (ARE)-driven promoter (ARE-TATA-Luc) and stably expressing ectopic AR, KCI838 was unable to inhibit promoter activation by dihydrotestosterone.

FIG. 9C is a graph showing that when 22Rv1 PCa cells were treated with KCI838, the compound selectively inhibited the expression of known ELK1-dependent endogenous target genes of AR, compared with classical ARE-driven gene targets of AR.

The results shown in FIGS. 9A, 9B, and 9C indicate that KCI838 is functionally selective in its actions for ELK1-dependent gene activation by AR.

KCI838 Selectively Blocks the Association of ELK1 and AR In Situ

The ability of KCI838 to disrupt the binding of AR to ELK1 in situ was directly tested using a BRET assay.

Figure 10A:
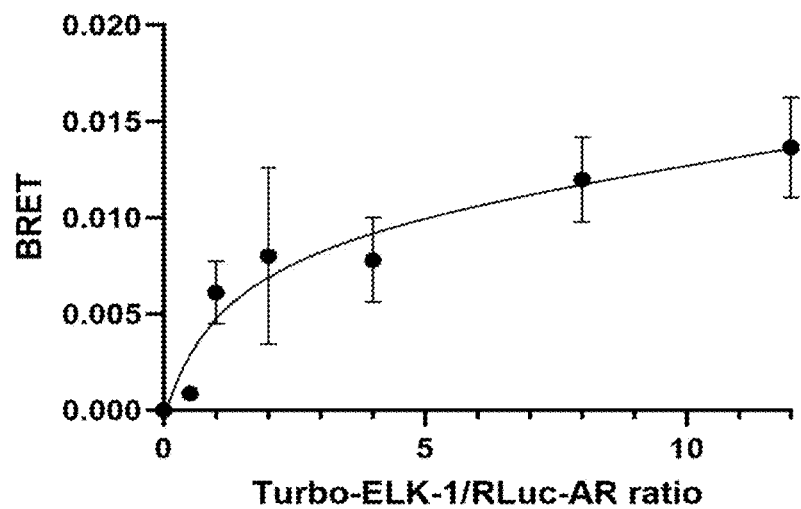
FIG. 10A is a graph showing that ELK1 binds to AR in situ.

For this assay, the BRET signal saturation curve was established in transfected HEK293T cells as a function of the ratio of Turbo-ELK1 to Rluc-AR, ranging from a ratio of 0.5 to 12 as shown in FIG. 10A. Protein expression was confirmed by Western blot, see FIG. 10B.

Based on this data, an ELK1: AR ratio of 4 was used for testing the effect of KCI838. HEK293T cells were transfected with Rluc-AR alone, and alongside Turbo-Elk. 24 hours later, cells were treated with KCI838 at the indicated doses. The following day, the cells were reseeded and allowed to settle for two hours before the BRET assay was performed. Results are shown in FIGS. 10C and 10D. KCI838 strongly inhibited the BRET signal for binding of AR to ELK1 at the two doses tested (60% and 95% inhibition at 0.4 μM and 10 μM respectively, of KCI838), see FIG. 10C. Protein expression in the transfected cells in FIG. 10C was confirmed by western blot, see FIG. 10D.

To ensure that KCI838 was not toxic to the HEK293 cells, viability of the cells was tested following extended (3 days) treatment with, vehicle, 0.4 μM, or 10 μM KCI838. Viable cells were counted after three days and the data was plotted as percent of untreated cells. The cells were found to be virtually completely viable as shown by the results in FIG. 10E.

FIG. 10A is a graph showing that the BRET signal saturation curve was established in transfected HEK293T cells as a function of the ratio of Turbo-ELK1 to Rluc-AR, ranging from a ratio of 0.5 to 12.

Figure 10B:
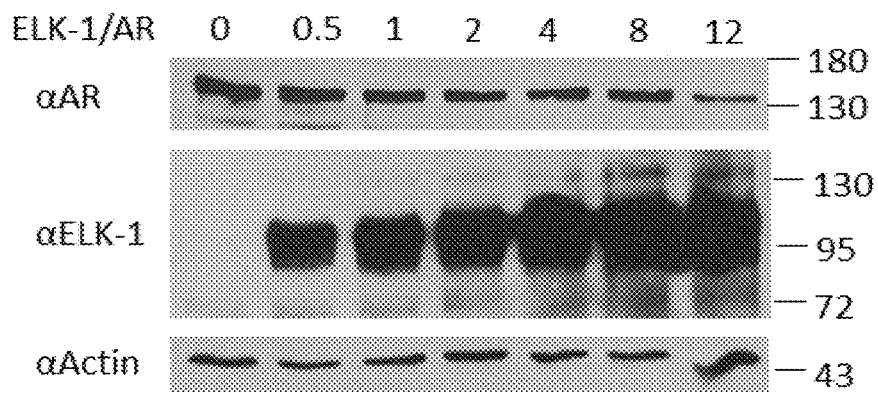
FIG. 10B is an image of a Western blot showing protein expression corresponding to the graph of FIG. 10A.
Figure 10C:
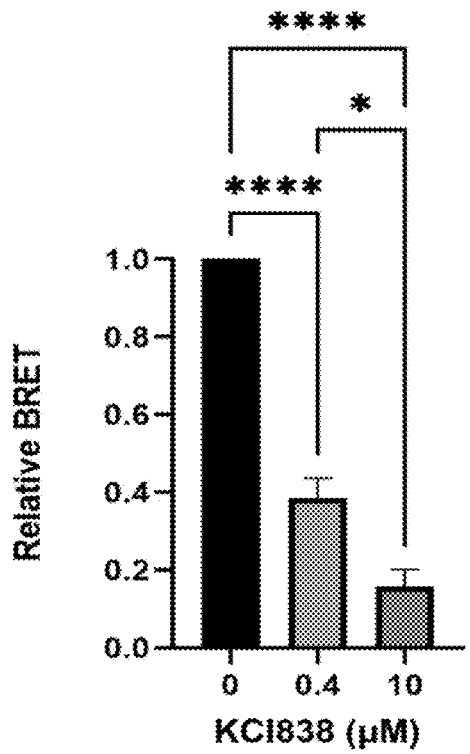
FIG. 10C is a graph showing that KCI838 blocks ELK1 binding to AR in situ.
Figure 10D:
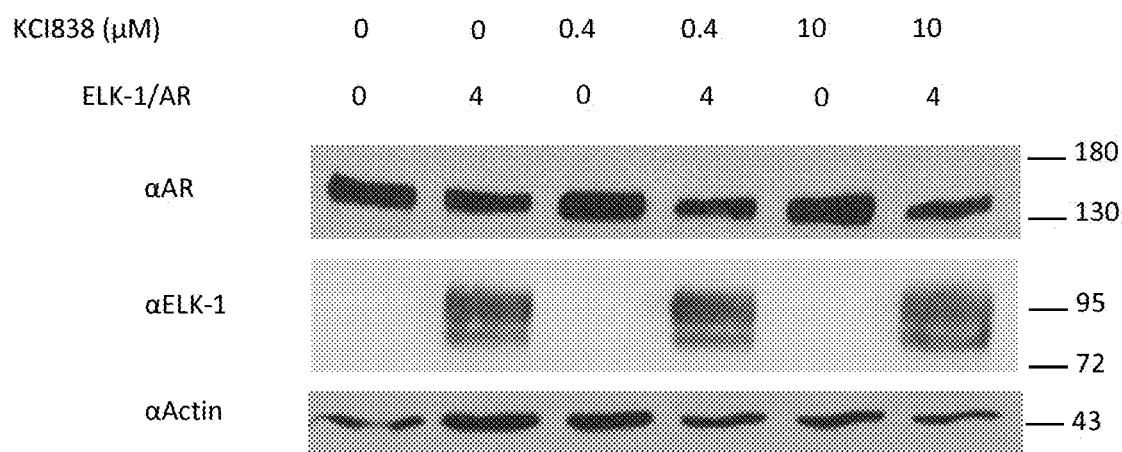
FIG. 10D is an image of a Western blot showing protein expression corresponding to the graph of FIG. 10C.

FIG. 10B is an image of a Western blot showing protein expression corresponding to the graph of FIG. 10A.

FIG. 10C is a graph showing that KCI838 strongly inhibited the BRET signal for binding of AR to ELK1 at the two doses tested (60% and 95% inhibition at 0.4 μM and 10 μM respectively, of KCI838.

FIG. 10D is an image of a Western blot showing protein expression corresponding to the graph of FIG. 10C.

Figure 10E:
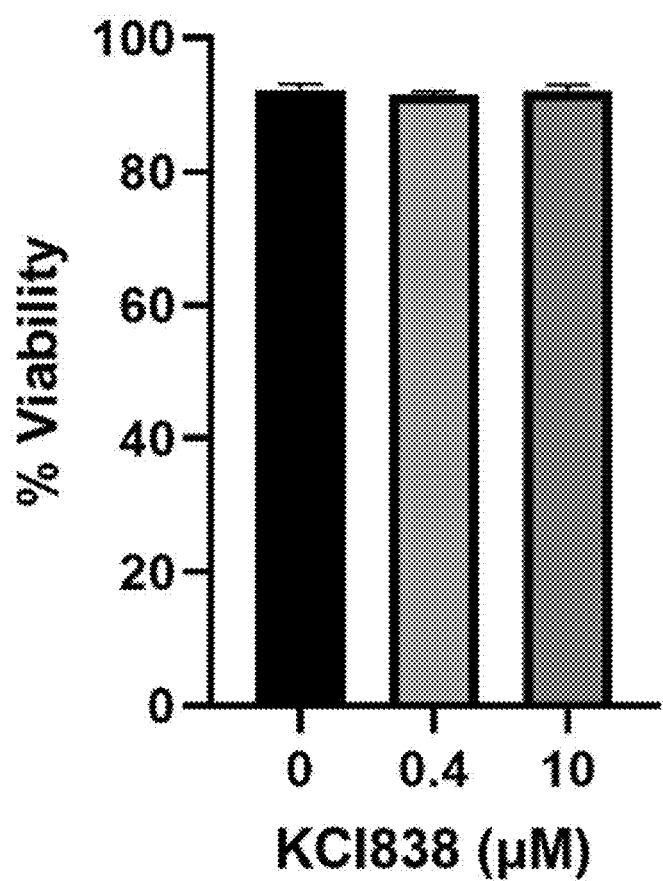
FIG. 10E is a graph showing that that KCI838 was not toxic to the HEK293 cells, viability of the cells was tested following extended (3 days) treatment with, vehicle, 0.4 µM, or 10 µM KCI838.

FIG. 10E is a graph showing that that KCI838 was not toxic to the HEK293 cells, viability of the cells was tested following extended (3 days) treatment with, vehicle, 0.4 μM, or 10 μM KCI838.

The results of FIGS. 10A, 10B, 10C, 10D, and 10E provide direct evidence that KCI838 blocks the binding of AR and ELK1 in situ.

The Growth Inhibitory Effect of KCI838 is Mediated by AR

To rule out the possibility of any off-target effects of KCI838 as mediating its growth inhibitory activity, recombinant 22Rv1 cells were generated in which total cellular AR was increased by lentiviral transduction and antibiotic selection of the pool of AR overexpressing cells. Control parental cells transduced with the vector alone were also generated, followed by similar selection.

Firstly, expression of ectopic wild-type AR was forced in 22Rv1 cells by lentiviral transduction and antibiotic selection. Levels of AR in control (vector transduced) cells vs. the cells overexpressing AR were measured on a Western blot and quantification by densitometry.

Figure 11A:
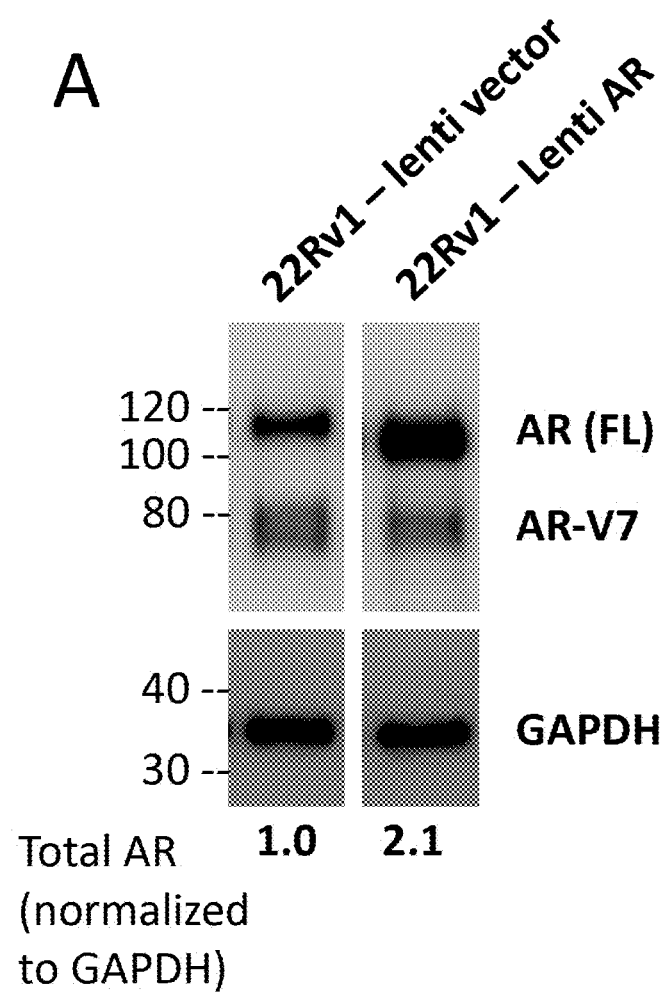
FIGS. 11A, 11B, 11C, 11D, and 11E show dependence on AR to mediate the growth inhibitory effect of KCI838 in 22Rv1 prostate cancer cells.

The AR transduced cells (22Rv1-Lenti AR) showed a 2.1-fold increase in total AR as measured by western blot compared with the control vector transduced cells (22Rv1-Lenti vector) as shown in FIG. 11A.

If AR is the mediator of the growth inhibitory effect of KCI838, then it would be predicted that for a 2-fold increase in AR expression, there should be no inhibition of growth in the AR overexpressing cells at a KCI838 concentration corresponding to the IC50 value for the control cells; this is because the total free AR at 50 percent occupancy by inhibitor in the 2× AR overexpressing cells should equal the total free AR in the untreated control cells. Moreover, the IC50 value of the compound in the AR overexpressing cells should increase and correspond to the IC75 value for the control cells.

To test this, the KCI838 dose responses for inhibition of colony formation were compared between the control and AR overexpressing cells, treating with DHT in both cases to ensure efficient nuclear localization of the ectopic AR. The 22Rv1 cells transduced with the control vector (FIG. 11B) or wild-type AR (FIG. 11C) were seeded in triplicate six well plates in phenol red-free conditioned media. 48 hours later, treatment with KCI838 at the indicated doses was initiated. KCI838 was replenished every 48 hours. Seven days later, colonies were fixed and stained with crystal violet.

Figure 11B:
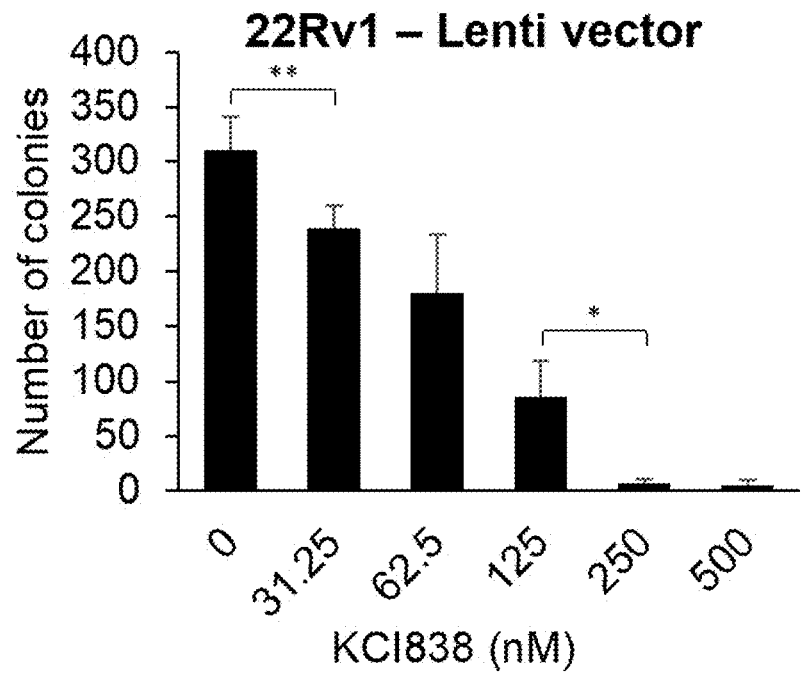
Figure 11C:
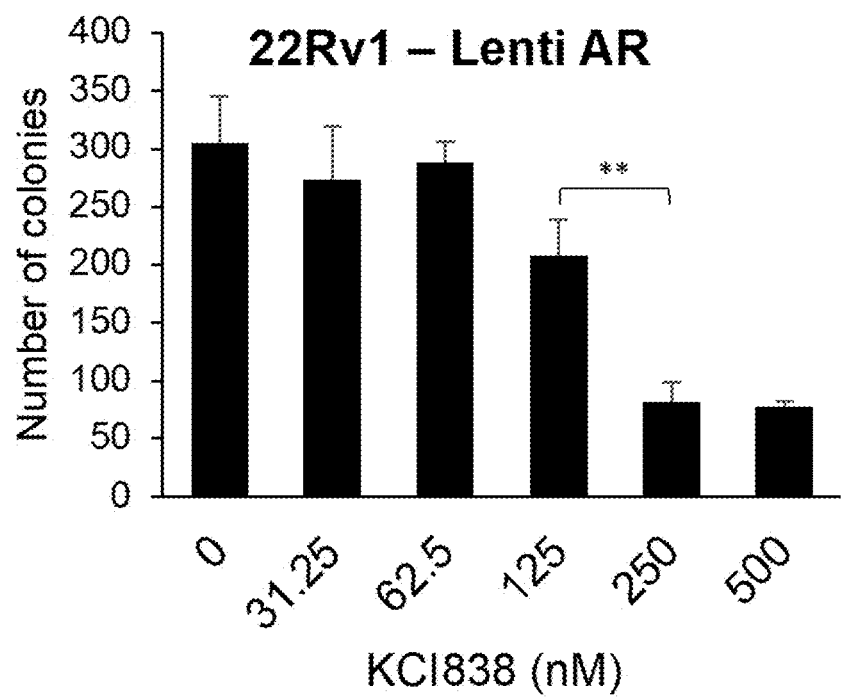
Figure 11D:
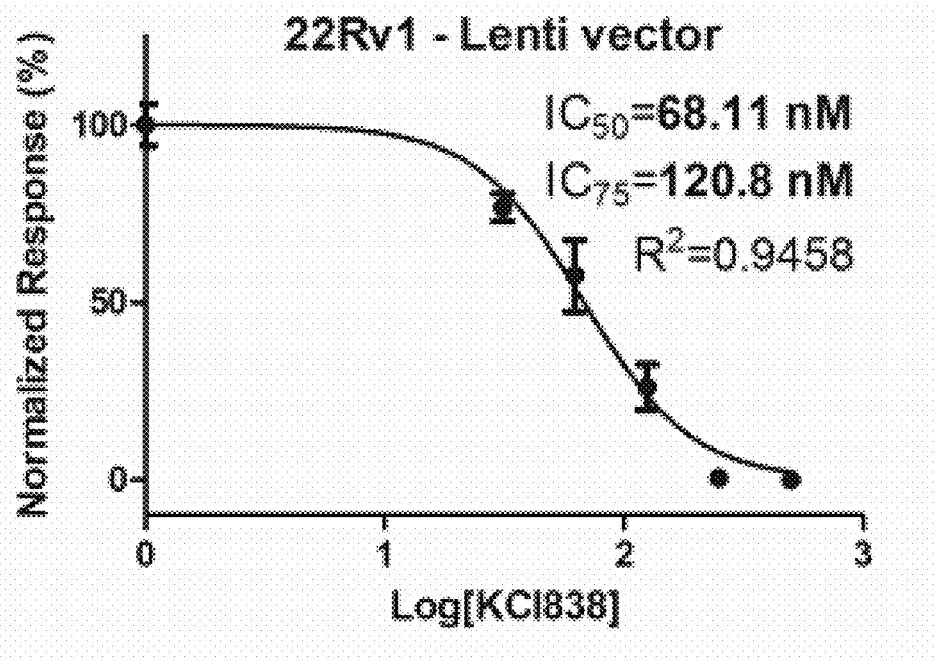
Figure 11E:
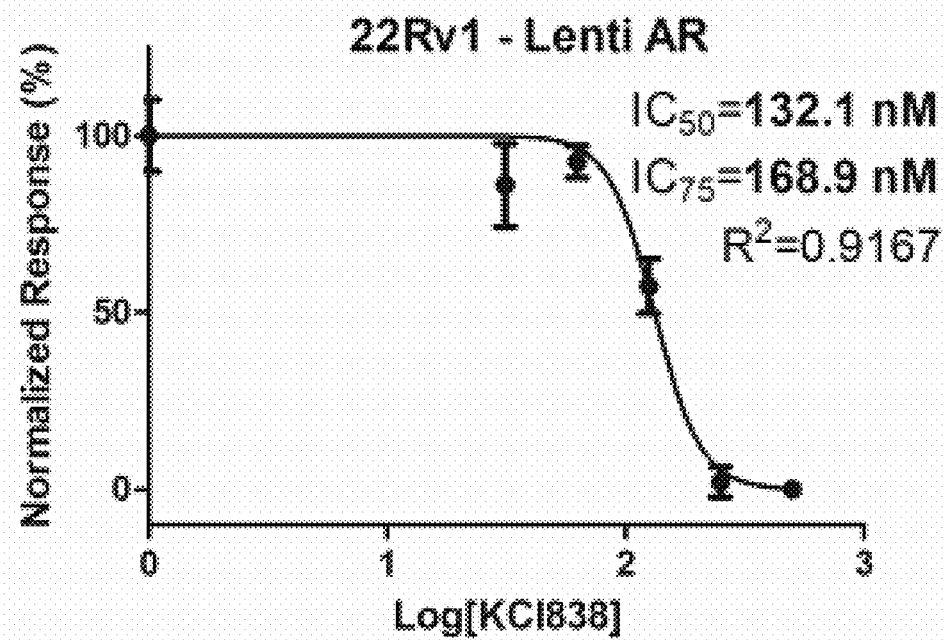

FIGS. 11D and 11E show nonlinear regression plots of colony counts corresponding to FIGS. 11B and 11C, respectively. P-value=* <0.05, ** <0.01 As seen in FIG. 11D, the IC50 and IC75 values were 68 nM and 121 nM, respectively, for the control cells. In the case of the AR overexpressing cells, there was no inhibition at 68 nM and the IC50 value increased to 132 nM, close to the IC75 value observed in the control cells, as shown in FIG. 11E.

FIG. 11A is an image of a Western blot demonstrating that AR transduced cells (22Rv1-Lenti AR) showed a 2.1-fold increase in total AR as measured by western blot compared with the control vector transduced cells (22Rv1-Lenti vector).

FIG. 11B is a graph showing KCI838 dose responses for inhibition of colony formation in control cells.

FIG. 11C is a graph showing KCI838 dose responses for inhibition of colony formation in AR overexpressing cells.

FIG. 11D is a graph showing that the IC50 and IC75 values were 68 nM and 121 nM, respectively, for the control cells.

FIG. 11E is a graph showing that for AR overexpressing cells there was no inhibition at 68 nM and the IC50 value increased to 132 nM, close to the IC75 value observed in the control cells in FIG. 11D.

FIGS. 11A, 11B, 11C, 11D, and 11E demonstrate a shift in KCI838 dose response as a result of AR overexpression in 22Rv1 cells. These results clearly implicate AR as the principal or only target for the observed physiological activity of KCI838 in prostate cancer cells.

Activity of KCI838 in Prostate Cancer Cells

KCI838 Inhibits Growth of Hormone-Refractory Prostate Cancer Model Cells that are Entirely Dependent on AR Spice Variants.

CWR22Rv1-AR-EK is a CRISPR-derived cell line that does not express wtAR and is exclusively dependent on splice variants of AR (AR-Vs) for growth. This model cell line thus mimics aggressively growing advanced prostate cancer tumor cells that are insensitive to current treatments such as testosterone suppression and androgen antagonists that cannot affect AR-Vs. Since KCI838 disrupts interaction of ELK1 with wtAR as well as AR-Vs, the effect of KCI838 on the growth of CWR22Rv1-AR-EK cells was tested. For this test, the cells were seeded in phenol red-free growth media. 24 hours later, the cells were treated with KCI838, FIG. 12A, or enzalutamide, FIG. 12B, at the indicated concentrations. Cells were grown for three or four days with replenishment of the drug at 48 hours. Cell viability was measured using the MTT assay.

Figure 12A:
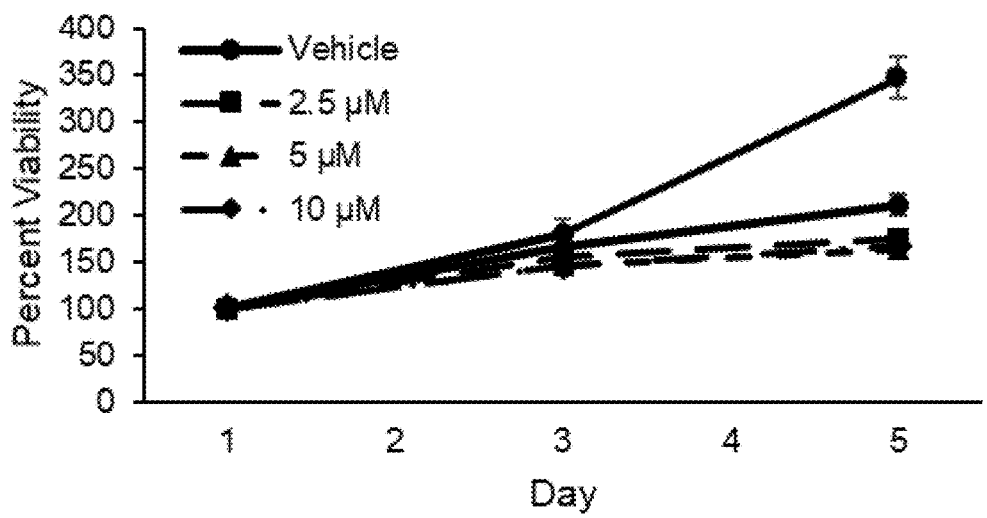
FIG. 12A is a graph showing a time course of growth inhibition by KCI838 in CWR22Rv1-AR-EK cells.
Figure 12B:
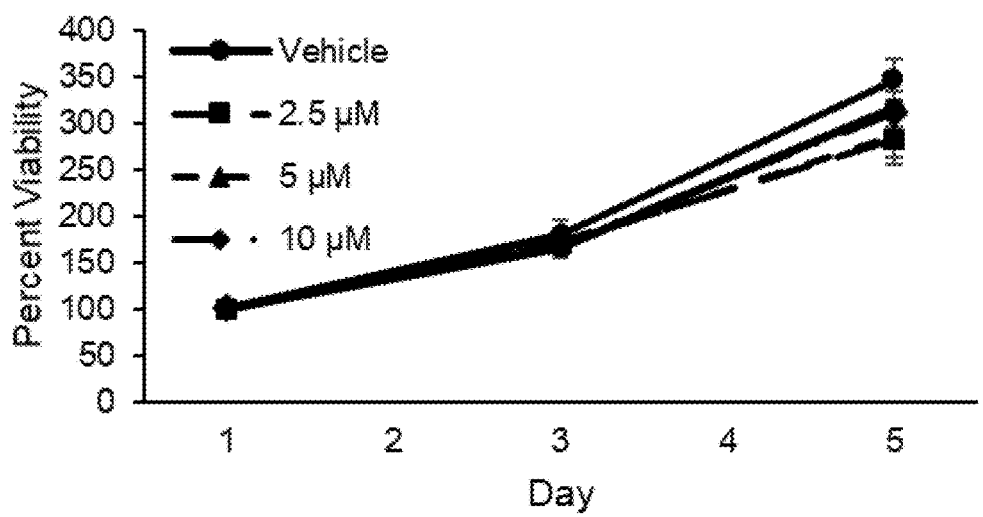
FIG. 12B is a graph showing a time course of growth inhibition by enzalutamide in CWR22Rv1-AR-EK cells.

FIG. 12A shows a time course of growth inhibition by KCI838 in CWR22Rv1-AR-EK cells. FIG. 12B shows a time course of growth inhibition by enzalutamide in CWR22Rv1-AR-EK cells.

FIG. 12A shows that KCI838 is a potent inhibitor of growth of CWR22Rv1-AR-EK cells. In contrast, FIG. 12B shows that CWR22Rv1-AR-EK cells were insensitive to enzalutamide.

KCI838 is Active in Normal Primary AR-Positive Prostate Epithelial Cells that Serve as a Model for Benign Prostatic Hyperplasia (BPH)

Growth of HPrEC Cells is Inhibited by KCI838

HPrEC cells are normal human primary prostate epithelial cells. In benign prostatic hyperplasia (BPH), normal prostate epithelial cells are believed to play a crucial role in the growth of stromal cells, at least in many cases, via paracrine signaling initiated by activation of AR in the epithelial cells. Many cases of BPH largely or entirely comprise epithelial cells. Indeed, BPH is known to respond to 5-alpha reductase inhibitors that decrease testosterone levels and elicit response in about half the patient population. However 5-alpha reductase inhibitors induce expression of AR-V7 that then causes resistance to the drug. Therefore, drugs that not only target AR but also AR-V7 and inhibit growth of normal prostate epithelial cells are therapeutics for BPH. As KCI838 is active against both AR and AR-V7, the ability of KCI838 to inhibit the growth of HPrEC cells was tested in this example.

For this, total RNA was extracted from 22Rv1 cells and HPrEC cells and AR mRNA was quantified by using a TaqMan probe that recognizes both wtAR and AR-V7. The relative mRNA levels are plotted as shown in FIG. 13A, demonstrating that there is comparable expression of AR mRNA in HPrEC cells relative to the malignant 22Rv1 cells.

For Western blot analysis, a lysate of HPrEC cells and different amounts (1×, 0.5× and 0.25×) of lysate from 22Rv1 cells were probed with an antibody to AR; both wtAR and AR-V7 bands are visible. GAPDH was used as the loading control. Results of western blot analysis, FIG. 13B, showed that AR protein expression in HPrEC cells was significant although it was less than in the malignant cells, as observed in prostate tissues. Notably, HPrEC cells also expressed AR-V7, similar to 22Rv1 cells, see FIG. 13B.

Growth of HPrEC cells was monitored by the MTT assay following treatment with vehicle or the indicated doses of KCI838. KCI838 inhibited the growth of HPrEC cells in a dose-dependent manner as shown in FIG. 13C.

Figure 13A:
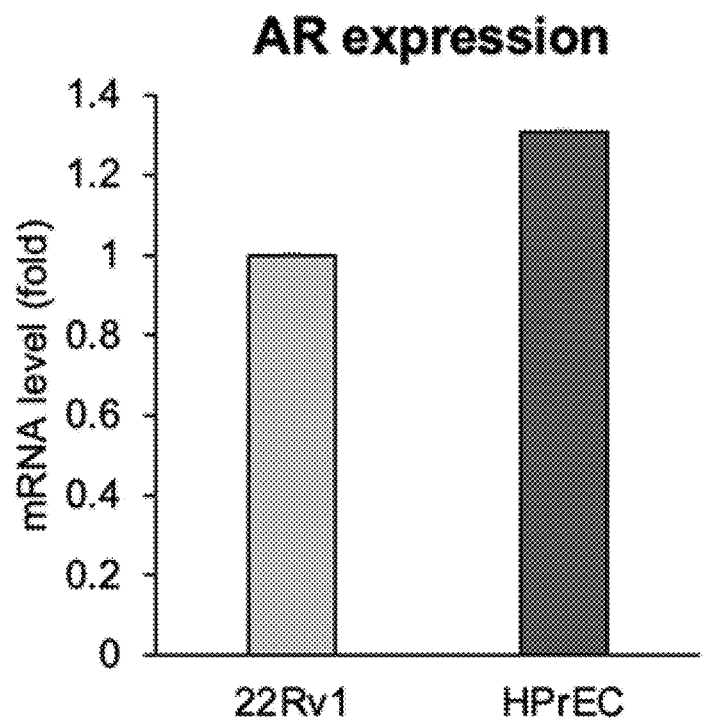
FIG. 13A is a graph showing that there is comparable expression of AR mRNA in HPrEC cells relative to the malignant 22Rv1 cells.
Figure 13B:
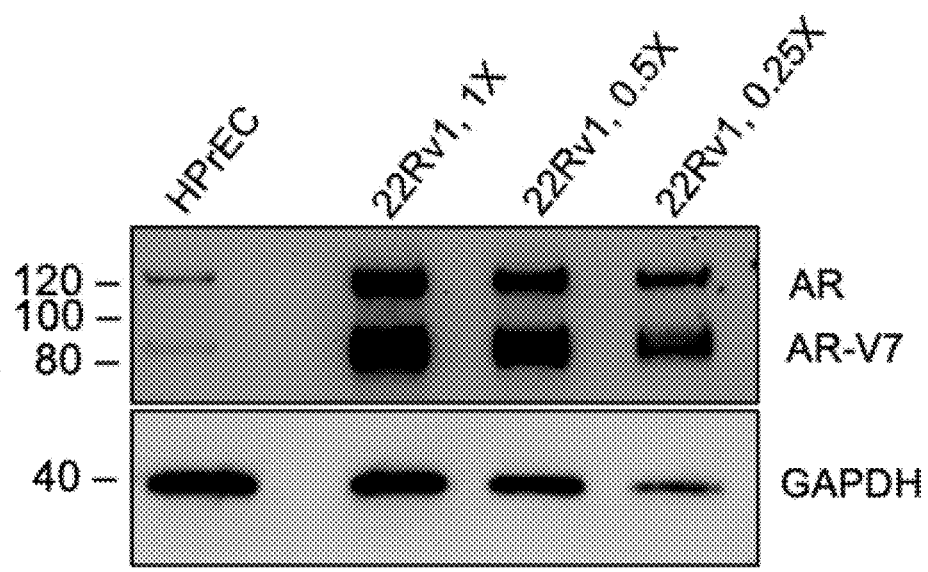
FIG. 13B is an image of a Western blot showing that HPrEC cells expressed both full-length AR and AR-V7, similar to 22Rv1 cells but at characteristically lower levels.
Figure 13C:
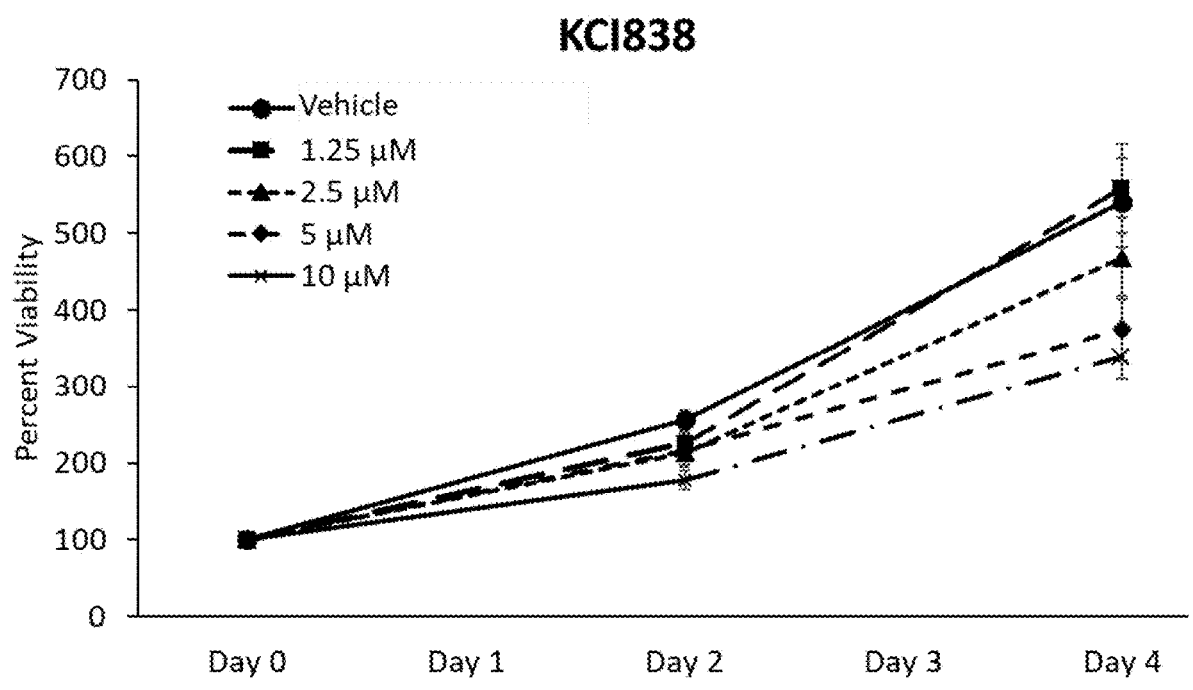
FIG. 13C is a graph showing results of treatment with vehicle or the indicated doses of KCI838 on growth of HPrEC cells monitored by the MTT assay.

FIGS. 13A, 13B, and 13C show that KCI838 is active in primary basal-like prostate epithelial cells expressing a low level of AR and that KCI838 is an effective inhibitor of normal prostate epithelial cells expressing AR-V7, indicating that KCI838 is useful for the treatment of BPH including cases that are resistant to currently used anti-androgens.

Synthesis of a Bioavailable Prodrug Form of KCI838

In this example, a lysine ester trihydrochloride of KCI838 is synthesized. Shown below is the chemical structure of the lysine ester trihydrochloride of KCI838 in which the ester bond is at the 3' position in the B ring.

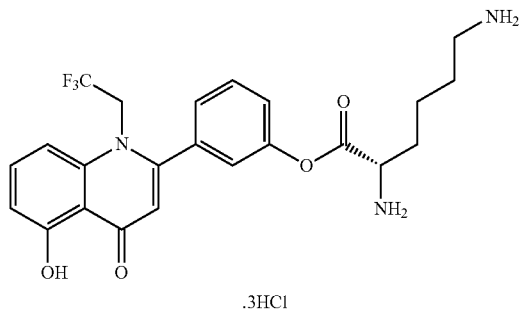 [SMILES: NCCCC[C@H](N)C(=O)Oc1cccc(-c2cc(=O)c3c(O)cccc3n2CC(F)(F)F)c1]

KCI838 Lysine Ester Prodrug

Figure 14:
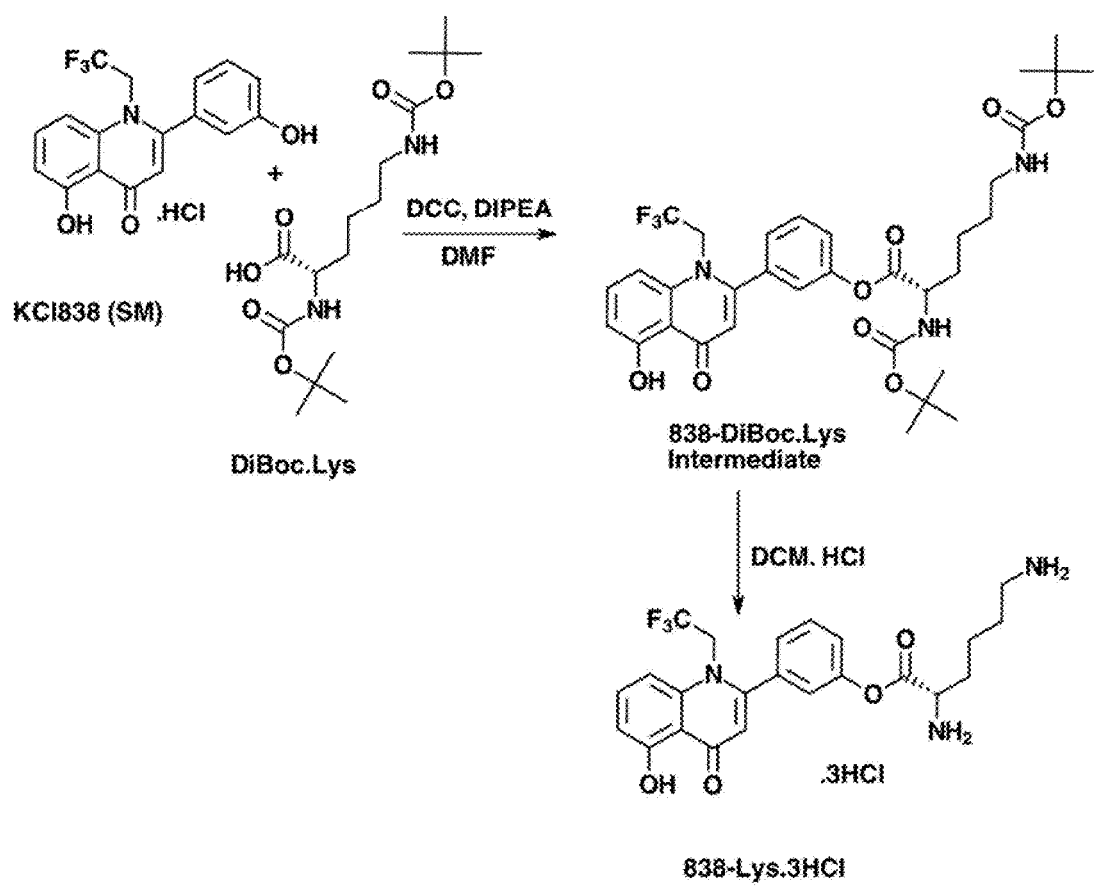
FIG. 14 is a drawing illustrating a synthetic scheme for preparing KCI838 lysine ester prodrug.

FIG. 14 shows a synthetic scheme for KCI838 Lysine Ester.3HCl, a prodrug of Structure I or II.

Synthesis Procedure:

Step 1: Synthesis of DiBoc-Lysine intermediate: 1 mmol of dicylococarbodimimide (DCC) and 1.1 mmol of Diboc-Lysine was weighed in round bottom flask. To this mixture 5 mL of dry DMF followed by 3 mmol of Diisopropylethylamine (DIPEA) was added. After activation of acid for 30 min, 1 mmol of KCI838 was added and the reaction mixture was stirred for 24 hours at room temperature (RT). After completion (TLC:Hexane:EtOAC 1:1) the crude reaction mixture was purified using silica gel column chromatography.

Step 2: Deprotection of Boc groups: The purified intermediate KCI838-DiBoc.Lys (1 mmol) was weighed in a round bottom flask followed by addition of 8 mL of dry dichloromethane and 2 mL of 1.25 M methanolic HCl solution dropwise. The reaction mixture was stirred at RT for 2 hours. Then solvents were evaporated and the pure KCI838Lys.3HCl salt was obtained by precipitation using DCM:hexanes mixture.

1H NMR, 19F NMR, and mass spectroscopy of both the DiBoc-Lysine intermediate and the final product demonstrate the successful synthesis.

Mapping of the Binding Site for the KCI838 Class of Drugs in AR

KCI838 and its Analogs Disrupt Association of the Amino-Terminal Domain of the Androgen Receptor with ELK1 by Modulating the Adjacent DNA Binding Domain Identification of the binding site for KCI838 and its analogs in AR will enable molecular modeling and design of next generation drugs targeting this site. The mode of interaction of the compounds with AR was investigated using systematic mutagenesis, coupled with ELK1 coactivation assays and testing polypeptide binding. In the full-length AR, deletion of neither ELK1 binding segment affected sensitivity of residual ELK1 coactivation to to the analog. Although the amino-terminal domain (NTD) is sufficient for association of AR with ELK1, interaction of the isolated NTD with ELK1 was insensitive to the analog. In contrast, coactivation of ELK1 by the AR-V7 splice variant, comprising the NTD and the DNA binding domain (DBD), showed sensitivity. Short deletions and point mutations within the DBD in a segment adjacent to the NTD spanning amino acids 558-595 interfered with coactivation of ELK1, and residual ELK1 coactivation by the mutants was insensitive to the analog. In a GST pull-down assay, the analog inhibited binding of ELK1 to an AR polypeptide that included the two ELK1 binding segments and the DBD but did not affect ELK1 binding to a similar AR segment that lacked the sequence downstream of residue 566. Raman spectroscopy detected a conformational change induced by the binding of the analog to the AR DBD. The data point to a putative KCI838 binding pocket within the crystal structure of the DBD and indicate that either mutations or binding of KCI807 at this site will induce conformational changes that disrupt ELK1 binding to the NTD. Analysis showed that the drug-interacting region (amino acids 558-594) is virtually the entire fold of AR-DBD excepting the alpha helix on the C-terminal end of the DBD.

Figure 15:
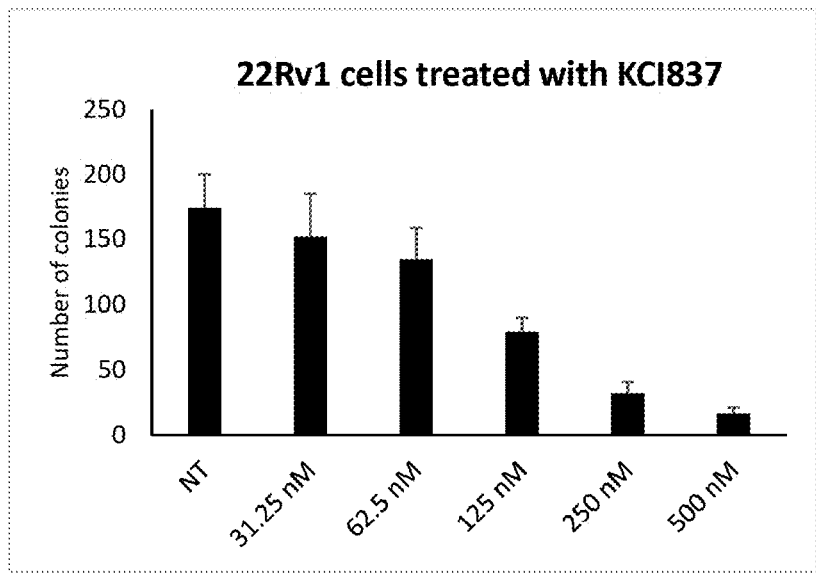
FIG. 15 is a graph showing that KCI837 inhibits colony formation in enzalutamide-resistant 22Rv1 prostate cancer cells.

KCI837 Inhibits Colony Formation in Enzalutamide-Resistant 22Rv1 Prostate Cancer Cells The ability of KCI837 to inhibit colony formation in castration and enzalutamide resistant prostate cancer cells was tested. 22Rv1 cells were seeded in triplicate six well plates in phenol red-free conditioned media. 48 hours later, treatment with KCI837 at the indicated doses was initiated. KCI837 was replenished every 48 hours. Seven days later, colonies were fixed and stained with crystal violet. Colony counts are plotted. Results are shown in FIG. 15, demonstrating that KCI837 inhibited colony formation in 22Rv1 cells in a dose-dependent manner with a calculated IC50 value of 98.6 nM.

Figure 16:
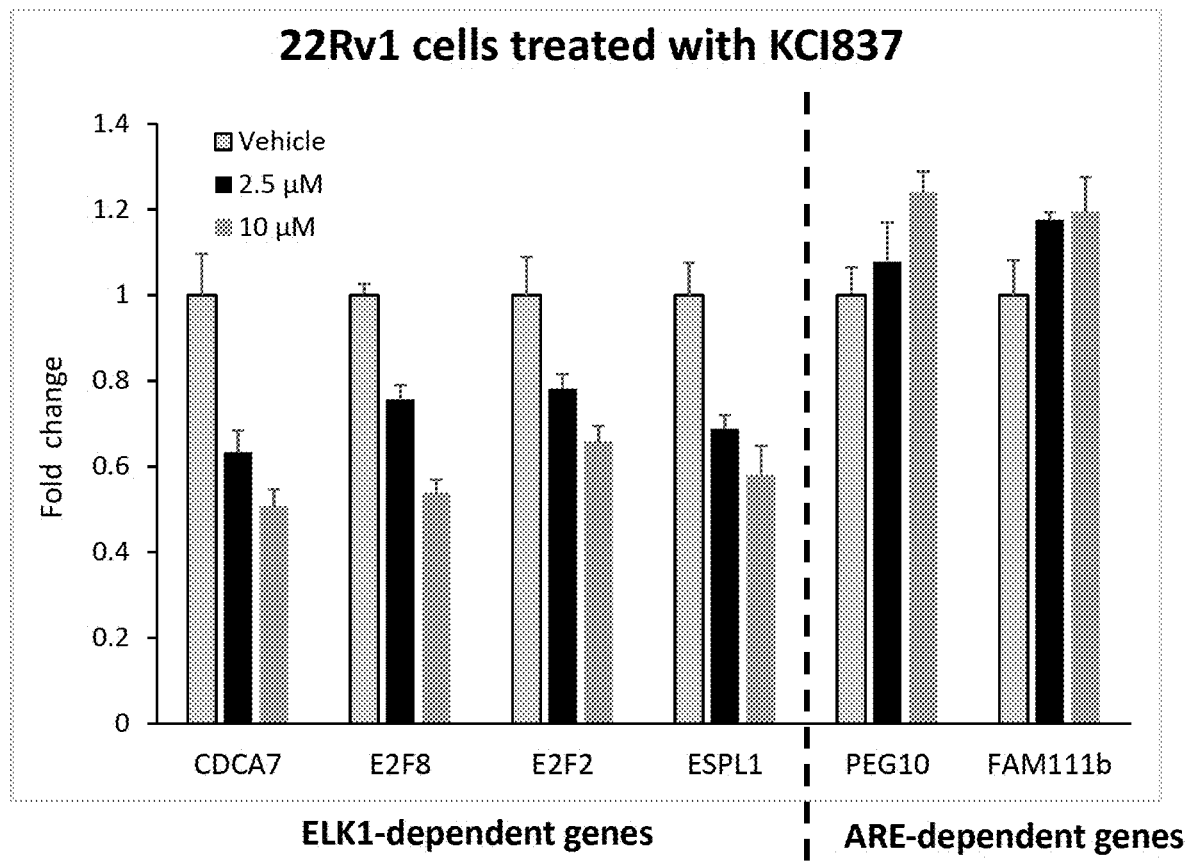
FIG. 16 is a graph showing that the inhibitory activity of KCI837 is selective for ELK1-dependent gene activation by AR.

The Inhibitory Activity of KCI837 is Selective for ELK1-Dependent Gene Activation by AR The target gene selectivity of KCI837 was examined by treating 22Rv1 PCa cells with KCI837 and measuring its effect on the expression of mRNAs of representative AR target genes that either required ELK1 for activation by AR or were activated by AR independent of ELK1 (ARE-dependent genes). 22Rv1 cells were treated for 72 hours with vehicle, 2.5 uM KCI837 or 10 uM KCI837. Total RNA was recovered from the cells and quantitative RT-PCR was used to measure mRNAs of the genes indicated. The control vehicle value was normalized to 100 percent for each gene. Results are shown in FIG. 16 which demonstrates that KCI837 selectively inhibited the expression of known ELK1-dependent endogenous target genes of AR, compared with classical ARE-driven gene targets of AR. These results indicate that KCI837 is functionally selective in its actions for ELK1-dependent gene activation by AR.

Item List

Item 1. A pharmaceutical composition, comprising a compound having chemical structural formula I:

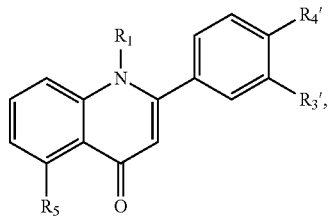

where $R_1$ is selected from the group consisting of: an alkyl group, a heteroalkyl group, an aryl group, a heteroaryl group, an alkenyl group, a heteroalkenyl group, an alkynyl group, a heteroalkynyl group, a cycloalkyl group, a hetercycloalkyl group, an alkylcycloalkyl group, a heteroalkyl cycloalkyl group, an aralkyl group, a heteroaralkyl group, an alkoxy group, a polar group, an ester and a charged group; a pharmaceutically acceptable hydrolysable, or enzymatically cleavable, prodrug form thereof; and/or a pharmaceutically acceptable salt thereof; where $R_4'$ is H or an alkoxy group; where both $R_5$ and $R_3'$ are OH, or where one or both of the OH groups is optionally modified as a pharmaceutically acceptable hydrolysable, or enzymatically cleavable, prodrug form thereof; and/or a deuterated form thereof; and/or a pharmaceutically acceptable salt thereof; and a pharmaceutically acceptable carrier.

Item 2. The pharmaceutical composition of item 1, wherein the pharmaceutically acceptable hydrolysable, or enzymatically cleavable, prodrug form thereof comprises an ester, a carbamate, or an ether.

Item 3. The pharmaceutical composition of item 1 or item 2, wherein $R_1$ is substituted with one or more halogen atoms.

Item 4. The pharmaceutical composition of item 3, wherein $R_1$ is substituted with one or more of: fluorine, chlorine, bromine, and iodine.

Item 5 The pharmaceutical composition of any of items 1 to 4, where one or both of $R_5$ and $R_3'$ of structure I is a pharmaceutically acceptable ester of an amino acid or dipeptide.

Item 6. The pharmaceutical composition of any of items 1 to 5, comprising a compound having structural formula II:

(II)

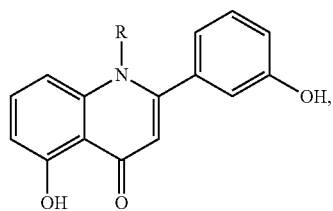

where R is methyl, propargyl, ethyl, propyl, isopropyl, isobutyl, tert-butyl, difluoroethyl, or trifluoroethyl; a derivative thereof, and/or a pharmaceutically acceptable hydrolysable, or enzymatically cleavable, prodrug form thereof, and/or a pharmaceutically acceptable salt thereof; and/or a deuterated form thereof; and a pharmaceutically acceptable carrier.

Item 7. The pharmaceutical composition of item 6, where R is trifluoroethyl.

Item 8. The pharmaceutical composition of item 6 or item 7, where one or both OH groups is a pharmaceutically acceptable ester of an amino acid or dipeptide.

Item 9. The pharmaceutical composition of any of items 1 to 8, comprising a compound having structural formula:

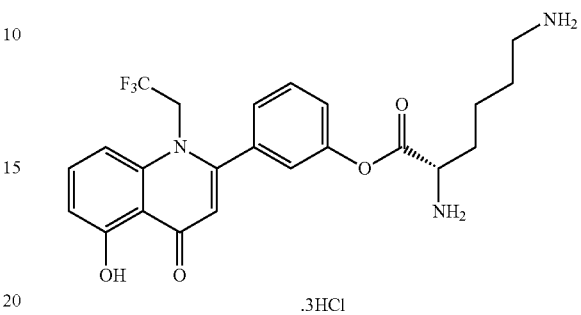

.3HCl

Item 10. The pharmaceutical composition of any of items 1 to 9, further comprising an additional therapeutic agent.

Item 11. A method of treating a steroid hormone receptor-dependent proliferative disorder in a subject in need thereof, comprising: administering a therapeutically effective dose of a pharmaceutical composition according to any of items 1 to 10 to the subject in need thereof.

Item 12. The method of item 11, wherein the subject has an androgen receptor-dependent cancer.

Item 13. The method of item 12, wherein the androgen receptor-dependent cancer is an androgen receptor-dependent prostate cancer or androgen receptor-dependent breast cancer.

Item 14. The method of item 11, wherein the subject has an estrogen receptor-dependent cancer.

Item 15. The method of item 14, wherein the estrogen receptor-dependent cancer is an estrogen receptor-dependent breast cancer.

Item 16. The method of item 11, wherein the subject has a steroid hormone receptor-dependent bladder cancer.

Item 17. The method of claim 11, wherein the subject has a benign prostate hyperplasia Item 18. The method of treatment of any one of items 11 to 16, further comprising an adjunct anti-cancer treatment.

Item 19. The method of any one of items 11 to 18, further comprising administration of an additional therapeutic agent.

Item 20. A compound having chemical structural formula I:

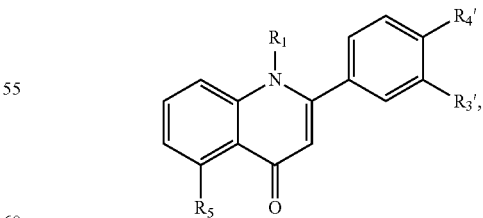

where $R_1$ is selected from the group consisting of: an alkyl group, a heteroalkyl group, an aryl group, a heteroaryl group, an alkenyl group, a heteroalkenyl group, an alkynyl group, a heteroalkynyl group, a cycloalkyl group, a hetercycloalkyl group, an alkylcycloalkyl group, a heteroalkyl cycloalkyl group, an aralkyl group, a heteroaralkyl group, an alkoxy group, a polar group, an ester and a charged group; a pharmaceutically acceptable hydrolysable, or enzymatically cleavable, prodrug form thereof; and/or a pharmaceutically acceptable salt thereof; where $R_4'$ is H or an alkoxy group; and where both $R_5$ and $R_3'$ are OH, or where one or both of the OH groups is optionally modified as a pharmaceutically acceptable hydrolysable, or enzymatically cleavable, prodrug form thereof; and/or a deuterated form thereof; and/or a pharmaceutically acceptable salt thereof.

Item 21. The compound of item 20, wherein the pharmaceutically acceptable hydrolysable, or enzymatically cleavable, prodrug form thereof comprises an ester, a carbamate, or an ether.

Item 22. The compound of item 20 or item 21, wherein $R_1$ is substituted with one or more halogen atoms.

Item 23. The compound of item 22, wherein $R_1$ is substituted with one or more of: fluorine, chlorine, bromine, and iodine.

Item 24. The compound of any of items 20 to 23, comprising a compound having structural formula II:

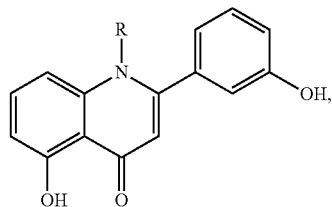

(II)

where R is methyl, propargyl, ethyl, propyl, isopropyl, isobutyl, tert-butyl, difluoroethyl, or trifluoroethyl; a derivative thereof, and/or a pharmaceutically acceptable hydrolysable, or enzymatically cleavable, prodrug form thereof; and/or a deuterated form thereof; and/or a pharmaceutically acceptable salt thereof.

Item 25. A commercial package comprising a pharmaceutical composition according to any of items 1 to 10 and/or a compound according to any of items 20 to 24.

Item 26. A method of synthesizing a 4-quinolone compound, comprising: contacting a flavone with a strong acid in a ratio of molar equivalents in the range of 1:2 to 1:100 in a closed system at a temperature in the range of 0° C. to 60° C. for a time period in the range of 2 hours to 10 days, producing a precipitate containing a corresponding flavylium salt; reacting the flavylium salt with an amine, wherein the flavylium salt and amine are present a ratio of molar equivalents in the range of 1:3 to 1:5, in an aprotic solvent for a second time period in the range of 2 hours to 2 days, producing a mixture comprising a 4-quinolone compound in the aprotic solvent; and purifying the 4-quinolone compound from the mixture.

Item 27. The method of synthesizing a 4-quinolone compound of item 26, wherein purifying the 4-quinolone compound from the mixture comprises at least one of: a) precipitation from an aprotic solvent such as hexane, acetone, ethyl acetate and mixtures in various proportions; b) recrystallization with a protic solvent such as ethanol or isopropanol; and c) using preparative plate chromatography method or column chromatography methods with material such as alumina (neutral or basic), producing purified 4-quinolone compound at purities of 90-98%, with yields in the range of 10-90%.

Item 28. The method of synthesizing a 4-quinolone compound of item 26 or 27, wherein hydroxyl groups of the flavone are not protected.

Item 29. The method of synthesizing a 4-quinolone compound of any of items 26 to 28, wherein the strong acid is not perchloric acid.

Item 30. A pharmaceutical composition or compound substantially as described herein.

Item 31. A method of treatment of a steroid hormone receptor-dependent proliferative disorder in a subject in need thereof substantially as described herein.

Item 32. The pharmaceutical composition of item 5 or item 8 wherein the amino acid is selected from the group consisting of: glycine, alanine, valine, leucine, isoleucine, tryptophan, phenylalanine and lysine.

Item 33. The pharmaceutical composition of item 5 or item 8 wherein the dipeptide is selected from the group consisting of: phenylalanine-glycine, valine-glycine, valine-alanine, serine-glutamic acid and proline-isoleucine.

Item 34. The compound of item 21, where one or both of $R_5$ and $R_3'$ of structure I is a pharmaceutically acceptable ester of an amino acid or dipeptide.

Item 35. The compound of item 24, where one or both OH groups is a pharmaceutically acceptable ester of an amino acid or dipeptide.

Item 36. The compound of item 34 or item 35 wherein the amino acid is selected from the group consisting of: glycine, alanine, valine, leucine, isoleucine, tryptophan, phenylalanine and lysine.

Item 37. The compound of item 34 or item 35 wherein the dipeptide is selected from the group consisting of: phenylalanine-glycine, valine-glycine, valine-alanine, serine-glutamic acid and proline-isoleucine.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A pharmaceutical composition, comprising a compound having chemical structural formula I:

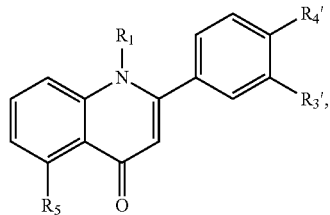

where $R_1$ is selected from the group consisting of: an alkyl group, a heteroalkyl group, an aryl group, a heteroaryl group, an alkenyl group, a heteroalkenyl group, an alkynyl group, a heteroalkynyl group, a cycloalkyl group, a heterocycloalkyl group, an alkylcycloalkyl group, a heteroalkyl cycloalkyl group, an aralkyl group, a heteroaralkyl group, an alkoxy group, a polar group, an ester and a charged group; a pharmaceutically acceptable hydrolysable, or enzymatically cleavable, prodrug form thereof; and/or a pharmaceutically acceptable salt thereof;

where $R_4'$ is H or an alkoxy group;

where both $R_5$ and $R_3'$ are OH, or where one or both OH groups is optionally modified as a pharmaceutically acceptable hydrolysable, or enzymatically cleavable, prodrug form thereof; and/or a deuterated form thereof; and/or a pharmaceutically acceptable salt thereof;

and a pharmaceutical acceptable carrier.

2. The pharmaceutical composition of claim 1, wherein the pharmaceutically acceptable hydrolysable, or enzymatically cleavable, prodrug form thereof comprises an ester, a carbamate, or an ether at one or more of $R_1$, $R_5$ and $R_3'$.

3. The pharmaceutical composition of claim 1, wherein $R_1$ is substituted with one or more halogen atoms.

4. The pharmaceutical composition of claim 3, wherein $R_1$ is substituted with one or more of: fluorine, chlorine, bromine, and iodine.

5. The pharmaceutical composition of claim 1, comprising a compound having structural formula II:

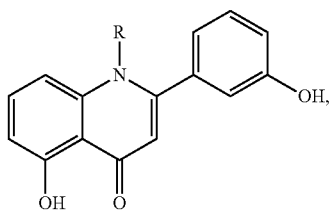

(II)

where R is methyl, propargyl, ethyl, propyl, isopropyl, isobutyl, tert-butyl, difluoroethyl, or trifluoroethyl; and/or a pharmaceutically acceptable hydrolysable, or enzymatically cleavable, prodrug form thereof, and/or a pharmaceutically acceptable salt thereof; and/or a deuterated foam thereof; and a pharmaceutically acceptable carrier.

6. The pharmaceutical composition of claim 5, where R is trifluoroethyl.

7. The pharmaceutical composition of claim 1, further comprising an additional therapeutic agent.

8. The pharmaceutical composition of claim 1, where one or both of $R_5$ and $R_3'$ of structure I is a pharmaceutically acceptable ester of an amino acid or dipeptide.

9. The pharmaceutical composition of claim 5, where one or both OH groups is a pharmaceutically acceptable ester of an amino acid or dipeptide.

10. The pharmaceutical composition of claim 1, comprising a compound having structural formula:

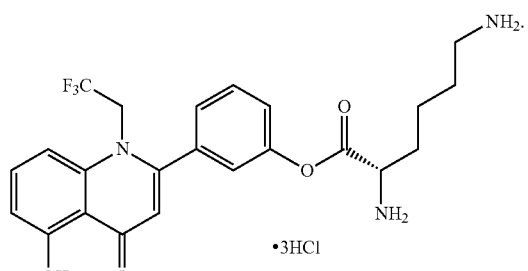

11. A method of treating a steroid hormone receptor-dependent proliferative disorder in a subject in need thereof, comprising: administering a therapeutically effective dose of a pharmaceutical composition according to claim 1 to the subject in need thereof.

12. The method of claim 11, wherein the subject has an androgen receptor-dependent cancer.

13. The method of claim 12, wherein the androgen receptor-dependent cancer is an androgen receptor-dependent prostate cancer or androgen receptor-dependent breast cancer.

14. The method of claim 11, wherein the subject has an estrogen receptor-dependent cancer.

15. The method of claim 14, wherein the estrogen receptor-dependent cancer is an estrogen receptor-dependent breast cancer.

16. The method of claim 11, wherein the subject has a steroid hormone receptor-dependent bladder cancer.

17. The method of treatment of claim 11, wherein the subject has a benign prostate hyperplasia.

18. The method of claim 11 further comprising administration of an additional therapeutic agent and/or adjunct anti-cancer treatment.

19. A commercial package comprising a pharmaceutical composition according to claim 1.

20. A method of synthesizing a 4-quinolone compound, comprising:

contacting a flavone with a strong acid in a ratio of molar equivalents in the range of 1:2 to 1:100 in a closed system at a temperature in the range of 0° C. to 60° C. for a time period in the range of 2 hours to 10 days, producing a precipitate containing a corresponding flavylium salt;

reacting the flavylium salt with an amine, wherein the flavylium salt and amine are present a ratio of molar equivalents in the range of 1:3 to 1:5, in an aprotic solvent for a second time period in the range of 2 hours to 2 days, producing a mixture comprising a 4-quinolone compound in the aprotic solvent; and purifying the 4-quinolone compound from the mixture.

* * * * *